US008158810B2

(12) United States Patent
Zablocki et al.

(10) Patent No.: US 8,158,810 B2
(45) Date of Patent: Apr. 17, 2012

(54) ALDH-2 INHIBITORS IN THE TREATMENT OF ADDICTION

(75) Inventors: Jeff Zablocki, Los Altos, CA (US); Matthew Abelman, Mountain View, CA (US); Michael Organ, Burlington (CA); Yaroslav Bilokin, Toronto (CA); Elfatih Elzein, Fremont, CA (US); Tetsuya Kobayashi, Sunnyvale, CA (US); Rao Kalla, Sunnyvale, CA (US); Thao Perry, San Jose, CA (US); Xiaofen Li, Mountain View, CA (US); Robert Jiang, Milpitas, CA (US); Ivan Diamond, Berkeley, CA (US); Lina Yao, San Francisco, CA (US); Peidong Fan, San Francisco, CA (US); Maria Pia Arolfo, Pleasanton, CA (US); Zhan Jiang, San Francisco, CA (US); Wing Ming Keung, Wayland, MA (US); Guoxin Tao, Brighton, MA (US)

(73) Assignees: Gilead Sciences, Inc., Foster City, CA (US); The Endowment For Research in Human Biology, Inc., Boston, MA (US)

( * ) Notice: Subject to any disclaimer, the term of this patent is extended or adjusted under 35 U.S.C. 154(b) by 521 days.

(21) Appl. No.: 12/371,398

(22) Filed: Feb. 13, 2009

(65) Prior Publication Data
US 2009/0209533 A1 Aug. 20, 2009

Related U.S. Application Data

(63) Continuation-in-part of application No. 12/019,034, filed on Jan. 24, 2008, which is a continuation-in-part of application No. 11/829,836, filed on Jul. 27, 2007, now abandoned.

(60) Provisional application No. 60/846,428, filed on Sep. 21, 2006, provisional application No. 60/834,083, filed on Jul. 27, 2006.

(51) Int. Cl.
*A61K 31/35* (2006.01)
*C07D 307/77* (2006.01)

(52) U.S. Cl. .......................... 549/403; 514/456
(58) Field of Classification Search .................. 549/403
See application file for complete search history.

(56) References Cited

U.S. PATENT DOCUMENTS

| | | | |
|---|---|---|---|
| 3,907,830 A | 9/1975 | Feuer et al. | |
| 4,166,862 A | 9/1979 | Feuer et al. | |
| 4,376,123 A | 3/1983 | Hausberg et al. | |
| 4,780,478 A | 10/1988 | Hausberg et al. | |
| 4,960,908 A | 10/1990 | Ito et al. | |
| 5,204,369 A | 4/1993 | Vallee et al. | |
| 5,624,910 A | 4/1997 | Vallee et al. | |
| 5,639,785 A * | 6/1997 | Kung | 514/456 |
| 5,679,806 A | 10/1997 | Zheng et al. | |
| 5,783,189 A | 7/1998 | Pei et al. | |
| 5,886,028 A | 3/1999 | Vallee et al. | |
| 6,121,010 A | 9/2000 | Vallee et al. | |
| 6,255,497 B1 | 7/2001 | Vallee et al. | |
| 7,368,434 B2 | 5/2008 | Keung et al. | |
| 2003/0229065 A1 | 12/2003 | Levy et al. | |
| 2008/0032995 A1 | 2/2008 | Zablocki et al. | |
| 2008/0207610 A1 | 8/2008 | Zablocki et al. | |
| 2008/0249116 A1 | 10/2008 | Zablocki et al. | |
| 2009/0124672 A1 | 5/2009 | Diamond et al. | |

FOREIGN PATENT DOCUMENTS

| | | | |
|---|---|---|---|
| CN | 1106790 | * | 7/1994 |
| EP | 0031885 A1 | | 7/1981 |
| FR | 2190411 A1 | | 2/1974 |
| WO | WO-91/15483 A1 | | 10/1991 |
| WO | WO-93/00896 A1 | | 1/1993 |
| WO | WO 03/051864 | * | 6/2003 |
| WO | WO-2004/002470 A1 | | 1/2004 |
| WO | WO 2005/033288 | * | 4/2005 |
| WO | WO-2006/002422 A2 | | 1/2006 |

OTHER PUBLICATIONS

Barz, W. et al. (1970) "The Degradation of Formononetin and Daidzein in Cicer Arietinum and *Phaseolus aureus*" *Phytochemistry* (Oxford), 9(8):1735-1744.
Deidrich, D. (1977) "Preparation and Physical Properties of Some Desoxybenzoins and Isoflavones" *J. Chem & Engineering Data* 22(4):448-451.
Dewick, P.M., (1977) "Biosynthesis of Pterocarpan Phyto Alexins in Trifolium-Pratense" *Phytochemistry* (Oxford) 16(1):93-98.
International Search Report for PCT/US2007/074665, International Filing Date Jul. 27, 2007, mailed Feb. 14, 2008.
Dorwald (2005) "Side Reactions in Organic Synthesis: A Guide to Successful Synthesis Design" *Weinheim: Wiley-VHC Verlag GmbH & Co. KGaA* Preface IX.
International Search Report for PCT/US2008/051862, International Filing Date Jan. 21, 2008, mailed Jan. 14, 2009.
Jagdish et al. (1980) "Chromatographic Separation of Synthetic Isoflavones on Stannic Molybdate Papers" *Journal of Liquid Chromatography* 3(7):1095-1104.
Jordan, V.C. (2003) "Tamoxifen: A Most Unlikely Pioneering Medicine" *Nature Reviews: Drug Discovery* 2:205-213.

(Continued)

*Primary Examiner* — Janet L. Andres
*Assistant Examiner* — John Mabry
(74) *Attorney, Agent, or Firm* — J. Elin Hartrum; Francis O. Ginah

(57) ABSTRACT

Disclosed are novel isoflavone derivatives having the structure of Formula I

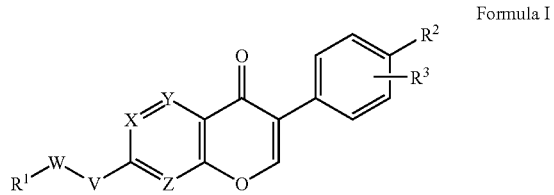

which are useful as ALDH-2 inhibitors for treating mammals for dependence upon drugs of addiction, for example addiction to dopamine-producing agent such as cocaine, morphine, amphetamines, nicotine, and alcohol.

11 Claims, 1 Drawing Sheet

OTHER PUBLICATIONS

Keung, W. et al. (1993) "Daidzin and Daidzein Suppress Free-Choice Ethanol Intake by Syrian Golden Hampsters" *Proc. Natl. Acad. Sci. USA* 90: 10008-10012.

Keung, W. et al. (1997) "Daidzin Inhibits Mitochondrial Aldehyde Dehydrogenase and Suppresses Ethanol Intake of Syrian Golden Hampsters" *Proc. National Academy of Science*, USA 94:1675-1679.

Kinoshita, T. et al. (1990) "One-Step Conversion of Flavanones: A New Facile Biomimetic Synthesis of Isoflavones" *Tetrahedron Letters 1990 United Kingdom* 31(50):7355-7356.

Lei, Y. et al. (2001) "Synthesis and Preliminary Studies on Bioactivities of 7-Hydroxy-4'-methylisoflavone" CA 137:185330.

Lin et al. (1996) "Isoflavonoid Compounds Extracted from *Pueraria iobata* Suppress Alcohol Preference in a Pharmacogenetic Rat Model of Alcoholism" *Alcoholism: Clinical and Experimental Research* 20:659-663.

Nilsson and Tottmar, (1987) "Biogenic Aldehydes in Brain: On Their Preparation and Reactions with Rat Brain Tissue" *Journal of Neurochemistry* 48:1566-1572.

Rooke N. et al. (2000) "The Mitochondrial Monoamine Oxidase-Aldehyde Dehydrogenase Pathway: A Potential Site of Action of Daidzin" *Journal of Medicinal Chemistry* 43: 4169-4179.

Shao, GX et al. (1981) "Studies on the Synthesis and Structure-antihypoxia Activity Relations of Daidzein, an Active Principle of *Puerarla pseudohiruta*, and its Derivatives" CA 94:174809.

Strejan et al. (1984) "Suppression of Chronic-Relapsing Experimental Allergic Encephalomyelitis in Strain-13 Guinea Pigs by Administration of Liposome-Associated Myelin Basic Protein" *Journal of Neuroimmunology* 7:27-41.

Tseng, T. et al. (1986) Synthesis of Daidzein Derivatives; CA 104:206988.

Zhou, G. et al. (2000) "Preparation and Bioactivities of Formonetin Derivatives" CA134:266171.

* cited by examiner

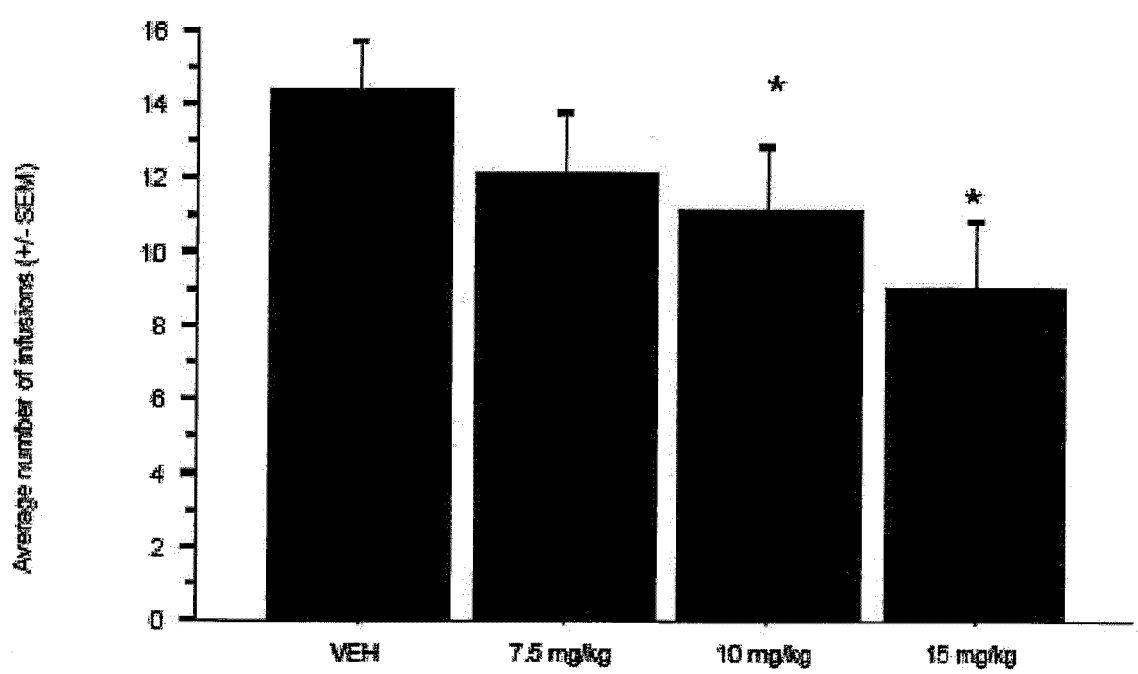
*, p<0.05 compared to VEH treated rats

ALDH-2 INHIBITORS IN THE TREATMENT OF ADDICTION

This application is a continuation in part of U.S. patent application Ser. No. 12/019,034, filed Jan. 24, 2008, which is a continuation in part of U.S. patent application Ser. No. 11/829,836, filed Jul. 27, 2007, which claims priority to U.S. Provisional Patent Application Ser. No. 60/846,428, filed Sep. 21, 2006, and U.S. Provisional Patent Application Ser. No. 60/834,083, filed Jul. 27, 2006, the entirety of which are incorporated herein by reference.

FIELD OF THE INVENTION

The present invention relates to novel ALDH-2 inhibitors, and to their use in treating mammals for dependence upon drugs of addiction, for example addiction to dopamine-producing agent such as cocaine, opiates, amphetamines, nicotine, and alcohol. ALDH-2 inhibitors have also been shown to be effective in treating obesity. The invention also relates to methods for the preparation of such compounds, and to pharmaceutical compositions containing them.

BACKGROUND

Today, dependence upon drugs of addiction causes major health problems worldwide. For example, alcohol abuse and alcohol dependency can cause liver, pancreatic and kidney disease, heart disease, including dilated cardiomyopathy, polyneuropathy, internal bleeding, brain deterioration, alcohol poisoning, increased incidence of many types of cancer, insomnia, depression, anxiety, and even suicide. Heavy alcohol consumption by a pregnant mother can also lead to fetal alcohol syndrome, which is an incurable condition. Additionally, alcohol abuse and alcohol dependence are major contributing factors for head injuries, motor vehicle accidents, violence and assaults, and other neurological and other medical problems.

Addiction to nicotine is estimated by the National Institute on Drug Abuse to kill nearly 500,000 Americans every year. This total represents about 1 in 6 of all deaths in the U.S. caused by any means, and is more than the total of deaths caused by use of alcohol, cocaine, heroin, suicide, car accidents, fire and AIDS combined. Cigarette smoking is the most popular method of using nicotine, but there are smokeless tobacco products; for example, snuff, chewing tobacco.

Nicotine addiction is linked to disease states such as leukemia, cataracts, pneumonia, and is the cause of about one-third of all cancer deaths, the foremost of which is lung cancer. In addition to cancer, cigarette smoking also causes lung diseases, such as bronchitis and emphysema, exacerbates asthma symptoms, and is the cause of chronic obstructive pulmonary diseases in general. It is also well known that cigarette smoking increases the risk of cardiovascular diseases, including stroke, heart attack, vascular disease, aneurysm, and the like.

Another major health problem is caused by cocaine abuse. Physical effects of cocaine use include constricted blood vessels, dilated pupils, and increased temperature, heart rate, and blood pressure. A user of cocaine can experience acute cardiovascular or cerebrovascular emergencies, such as a heart attack or stroke, potentially resulting in sudden death. Other complications associated with cocaine use include disturbances in heart rhythm, chest pain and respiratory failure, seizures and headaches, and gastrointestinal complications such as abdominal pain and nausea. Because cocaine has a tendency to decrease appetite, many chronic users can become malnourished. Repeated use of cocaine may lead to a state of increasing irritability, restlessness, and paranoia. This can result in a period of full-blown paranoid psychosis, in which the user loses touch with reality and experiences auditory hallucinations.

Moreover, it is well known that the concurrent abuse of nicotine, cocaine, and alcohol is common. It has been found that the combination of cocaine and alcohol exerts more cardiovascular toxicity than either drug alone in humans.

Historically, treating chemical dependence largely involved attempts to persuade patients to discontinue use of the substance voluntarily (behavioral therapy). However, cocaine, morphine, amphetamines, nicotine, and alcohol, and other types of dopamine-producing agents are highly addictive substances, and dependence upon such drugs can be harder to break and is significantly more damaging than dependence on most other addictive substances. In particular, alcohol, cocaine, and heroin dependence are typically seen to be chronic relapsing disorders.

There has been some moderate success in providing effective treatments for tobacco addiction by the use of nicotine replacement therapy, such as nicotine gum or the nicotine transdermal patch. Additionally, antidepressants and antihypertensive drugs have been tried, with modest success. Attempts have also been made to treat tobacco addiction by persuading patients to discontinue the use of tobacco voluntarily (behavioral therapy), but this method has not proved to be very successful. Accordingly, it is clearly desirable to find a treatment for tobacco addiction that reduces or prevents the craving for nicotine that does not involve nicotine replacement therapy or the use of antidepressants and antihypertensive drugs.

Accordingly, there has been much interest in the scientific community in attempting to find substances that could be employed to ameliorate dependency on addictive agents. Two compounds that have previously been employed for the treatment of alcohol abuse are known as disulfiram (Antabuse™) and cyanamide. Additionally, it has been recently proposed that disulfiram can be used for the treatment of cocaine dependency (for example, see Bonet et al., Journal of Substance Abuse Treatment, 26 (2004), 225-232).

More recently it has been shown that a compound known as daidzein is effective in suppressing ethanol intake. Daidzein is the major active component obtained from extracts of *Radix puerariae*, a traditional Chinese medication that suppresses ethanol intake in Syrian golden hamsters. See Keung, W. M. and Vallee, B. L. (1993) Proc. Natl. Acad. Sci. USA 90, 10008-10012 and Keung, W. M., Klyosov, A. A., and Vallee, B. L. (1997) Proc. Natl. Acad. Sci. USA 94, 1675-1679, and U.S. Pat. Nos. 5,624,910 and 6,121,010.

It has been shown that daidzein is an isoflavone of the formula:

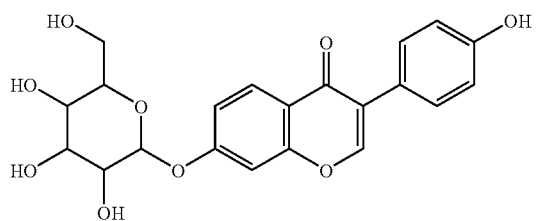

Removal of the sugar provides a compound known as daidzein, which has also been shown to be effective in suppressing ethanol uptake, but with decreased potency.

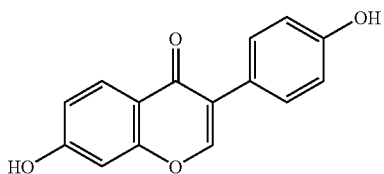

U.S. Pat. Nos. 5,624,910 and 6,121,010 disclosed ether derivatives of daidzein, which were shown to be effective in treating ethanol dependency. Daidzein and its analogs were shown to be potent and selective inhibitors of human mitochondrial aldehyde dehydrogenase (ALDH-2), which is an enzyme involved in the major enzymatic pathway responsible for ethanol metabolism in humans. It was also found that daidzein analogues that inhibit ALDH-2 but also inhibit the monoamine oxidase (MAO) pathway were the least effective antidipsotropic activity.

It has now surprisingly been found that ALDH-2 inhibitors are also useful for the treatment of other addictive agents such as cocaine, heroin, and nicotine, and in particular, ameliorate the tendency of abusers to relapse.

SUMMARY OF THE INVENTION

Accordingly, in a first aspect, the invention relates to compounds of Formula I:

Formula I

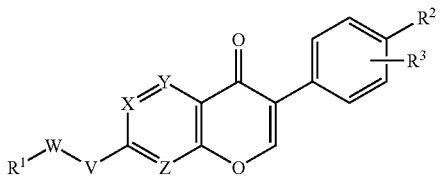

wherein:
  $R^1$ is optionally substituted phenyl, optionally substituted heteroaryl, or optionally substituted heterocyclyl;
  $R^2$ is hydrogen, hydroxy, halogen, optionally substituted lower alkoxy, optionally substituted lower alkyl, cyano, optionally substituted heteroaryl, $C(O)OR^5$, —$C(O)R^5$, —$SO_2R^{15}$, —$B(OH)_2$, —$OP(O)(OR^5)_2$, $C(R^{20})NHR^{22}$, —$NHR^4$, or —$C(O)NHR^5$, in which,
  $R^4$ is hydrogen, —$C(O)NHR^5$, or —$SO_2R^{15}$, or $C(O)R^5$;
  $R^5$ is hydrogen, optionally substituted lower alkyl;
  $R^{15}$ is optionally substituted lower alkyl or optionally substituted phenyl; or
  $R^2$ is —O-Q-$R^6$, in which Q is a covalent bond or lower alkylene and $R^6$ is optionally substituted heteroaryl;
  $R^3$ is hydrogen, cyano, optionally substituted amino, lower alkyl, lower alkoxy, or halo;
  X, Y and Z are chosen from —$CR^7$— and —N—, in which $R^7$ is hydrogen, lower alkyl, lower alkoxy, or halo;
  V is oxygen, sulfur, or —NH—; and
  W is -$Q^1$-T-$Q^2$-, wherein
    $Q^1$ is a covalent bond or $C_{1-6}$ linear or branched alkylene optionally substituted with hydroxy, lower alkoxy, amino, cyano, or =O;
    $Q^2$ is $C_{1-6}$ linear or branched alkylene optionally substituted with hydroxy, lower alkoxy, amino, cyano, or =O; and
    T is a covalent bond, —O—, or —NH—, or
    T and $Q^1$ may together form a covalent bond,
  $R^{20}$ and $R^{22}$ are independently selected from the group consisting of hydrogen, hydroxy, $C_{1-15}$ alkyl, $C_{2-15}$ alkenyl, $C_{2-15}$ alkynyl, heterocyclyl, aryl, benzyl, and heteroaryl,
    wherein the alkyl, alkenyl, alkynyl, heterocyclyl, aryl, benzyl, and heteroaryl moieties are optionally substituted with from 1 to 3 substituents independently selected from halo, alkyl, mono- or dialkylamino, alkyl or aryl or heteroaryl amide, CN, O—$C_{1-6}$ alkyl, $CF_3$, $OCF_3$, $B(OH)_2$, $Si(CH_3)_3$, heterocyclyl, aryl, and heteroaryl
    wherein the heterocyclyl, aryl, and heteroaryl substituent are optionally substituted with from 1 to 3 substituents independently selected from halo, $CF_3$, $C_{1-4}$ lower alkyl, and $C_{1-3}$ alkoxy.

In a second aspect of the invention, pharmaceutical formulations are provided comprising a therapeutically effective amount of an ALDH-2 inhibitor of Formula I, and at least one pharmaceutically acceptable carrier.

In a third aspect of the invention, methods of using the compounds of Formula I in the treatment of addiction. The method comprises administering to a mammal in need thereof a therapeutically effective dose of a compound of Formula I. The addiction may be to an agent such as, but are not limited to, cocaine, opiates, amphetamines, nicotine, and alcohol.

In one preferred embodiment, the invention relates to a group of compounds of Formula I in which X, Y and Z are all —$CR^6$—, in which $R^6$ is hydrogen. Within this group, preferred compounds include a class in which $R^1$ is optionally substituted phenyl, $R^2$ is 4-hydroxyl, $R^3$ is hydrogen, V is oxygen, and W is methylene.

One preferred subclass within this class includes those compounds in which $R^1$ is phenyl substituted with from 1 to 3 substituents, which are independently selected from the group consisting of carboxyl, carboxylic ester, carboxamido, cyano, tetrazolyl, halo, or lower alkyl substituted by halo, particularly monosubstituted compounds in which the substitution is at the 3-position and disubstituted compounds in which the substitutions are at the 3,5-positions.

Within this subclass are also compounds wherein the $R^1$ phenyl group is monosubstituted at the 3-position with —$CO_2R^{20}$ wherein $R^{20}$ is $C_{1-3}$ alkyl optionally substituted with from 1 to 3 substituents independently selected from halo, mono- or dialkylamino, and aryl, heteroaryl, cycloalkyl or heterocyclyl optionally substituted with from 1 to 3 substituents independently selected from halo, $CF_3$, $C_{1-4}$ lower alkyl, and $C_{1-3}$ alkoxy. Within this subclass, compounds wherein $R^{20}$ is a monosubstituted, five or six-membered monocyclic heterocyclic moiety are preferred.

Another preferred class included compounds in which $R^1$ is optionally substituted phenyl, $R^2$ is 4-$NHR^4$, $R^3$ is hydrogen, V is oxygen, and W is methylene. One preferred subclass includes those compounds in which $R^1$ is phenyl substituted with from 1 to 3 substituents which are independently selected from the group consisting of carboxyl, carboxamido, cyano, tetrazolyl, halo, or lower alkyl substituted by halo, particularly monosubstituted compounds in which the substitution is at the 3-position and disubstituted compounds in which the substitutions are at the 3,5-positions. More preferred are those compounds where $R^4$ is —$SO_2R^5$, more preferably where $R^5$ is methyl.

In another preferred group, $R^1$ is optionally substituted heteroaryl, particularly where $R^1$ is a five or six membered heteroaryl ring that includes oxygen and nitrogen atoms, V is oxygen, W is methylene, preferably where $R^2$ is 4-hydroxy and $R^3$ is hydrogen. Within this group, one preferred subgroup includes those compounds in which R¹ is 1,3-oxazolyl, 1,3-thiazolyl, or (1,2,4-oxadiazol-3-yl), which are optionally substituted by phenyl substituted by carboxyl, carboxamido, cyano, tetrazolyl, halo, or lower alkyl substituted by halo, for example trifluoromethyl, particularly monosubstituted compounds in which the substitution is at the 3-position and disubstituted compounds in which the substitutions are at the 3,5-positions.

At present, the compounds for use in the invention include, but are not limited to:

3-{[3-(4-hydroxyphenyl)-4-oxochromen-7-yloxy]methyl}benzoic acid;
3-{[3-(4-hydroxyphenyl)-4-oxochromen-7-yloxy]methyl}benzenecarbonitrile;
3-(4-hydroxyphenyl)-7-[(3-(5H-1,2,3,4-tetrazol-5-yl)phenyl)methoxy]chromen-4-one;
3-{[3-(4-hydroxyphenyl)-4-oxochromen-7-yloxy]methyl}benzamide;
3-[(3-{4-[(methylsulfonyl)amino]phenyl}-4-oxochromen-7-yloxy)methyl]benzene-carbonitrile;
3-[(3-{4-[(methylsulfonyl)amino]phenyl}-4-oxochromen-7-yloxy)methyl]benzamide;
3-(4-hydroxyphenyl)-7-{[3-(trifluoromethyl)phenyl]methoxy}chromen-4-one;
3-(4-hydroxyphenyl)-7-{[4-methoxy-3-(trifluoromethyl)phenyl]methoxy}chromen-4-one;
7-{[3-fluoro-5-(trifluoromethyl)phenyl]methoxy}-3-(4-hydroxyphenyl)chromen-4-one;
3-(4-hydroxyphenyl)-7-{[5-(2-methoxyphenyl)(1,2,4-oxadiazol-3-yl)]methoxy}chromen-4-one;
3-(4-hydroxyphenyl)-7-[(5-phenyl(1,2,4-oxadiazol-3-yl))methoxy]chromen-4-one;
3-(4-hydroxyphenyl)-7-({5-[3-(trifluoromethyl)phenyl](1,2,4-oxadiazol-3-yl)}methoxy)chromen-4-one;
3-(4-hydroxyphenyl)-7-({5-[4-(trifluoromethyl)phenyl](1,2,4-oxadiazol-3-yl)}methoxy)chromen-4-one;
7-({5-[3-fluoro-5-(trifluoromethyl)phenyl](1,2,4-oxadiazol-3-yl)}methoxy)-3-(4-hydroxyphenyl)chromen-4-one;
7-({5-[4-fluoro-3-(trifluoromethyl)phenyl](1,2,4-oxadiazol-3-yl)}methoxy)-3-(4-hydroxyphenyl)chromen-4-one;
7-({5-[2,5-bis(trifluoromethyl)phenyl](1,2,4-oxadiazol-3-yl)}methoxy)-3-(4-hydroxyphenyl)chromen-4-one;
prop-2-enyl 3-(3-{[3-(4-hydroxyphenyl)-4-oxochromen-7-yloxy]methyl}-1,2,4-oxadiazol-5-yl)benzoate;
prop-2-enyl 3-{[3-(4-hydroxyphenyl)-4-oxochromen-7-yloxy]methyl}benzoate;
methyl 4-{[3-(4-hydroxyphenyl)-4-oxochromen-7-yloxy]methyl}benzoate;
methyl 3-{[3-(4-hydroxyphenyl)-4-oxochromen-7-yloxy]methyl}benzoate;
ethyl 4-{[3-(4-hydroxyphenyl)-4-oxochromen-7-yloxy]methyl}benzoate;
methylethyl 3-{[3-(4-hydroxyphenyl)-4-oxochromen-7-yloxy]methyl}benzoate;
4-{[3-(4-hydroxyphenyl)-4-oxochromen-7-yloxy]methyl}benzoic acid;
4-{[3-(4-hydroxyphenyl)-4-oxochromen-7-yloxy]methyl}benzamide;
3-(4-hydroxyphenyl)-7-{[5-(3-methoxyphenyl)(1,2,4-oxadiazol-3-yl)]methoxy}chromen-4-one; 3-(3-{[3-(4-hydroxyphenyl)-4-oxochromen-7-yloxy]methyl}-1,2,4-oxadiazol-5-yl)benzoic acid.
7-({5-[3,5-bis(trifluoromethyl)phenyl](1,2,4-oxadiazol-3-yl)}methoxy)-3-(4-hydroxyphenyl)chromen-4-one;
3-(3-{[3-(4-hydroxyphenyl)-4-oxochromen-7-yloxy]methyl}-1,2,4-oxadiazol-5-yl)benzenecarbonitrile;
3-(4-hydroxyphenyl)-7-[(3-phenyl(1,2,4-oxadiazol-5-yl))methoxy]chromen-4-one;
3-(4-hydroxyphenyl)-7-({3-[3-(trifluoromethyl)phenyl](1,2,4-oxadiazol-5-yl)}methoxy)chromen-4-one;
3-(4-hydroxyphenyl)-7-({3-[4-chlorophenyl](1,2,4-oxadiazol-5-yl)}methoxy)chromen-4-one;
3-(4-hydroxyphenyl)-2-(trifluoromethyl)-7-({5-[3-(trifluoromethyl)phenyl](1,2,4-oxadiazol-3-yl)}methoxy)chromen-4-one;
7-({5-[5-fluoro-3-(trifluoromethyl)phenyl](1,2,4-oxadiazol-3-yl)}methoxy)-3-(4-hydroxyphenyl)-2-(trifluoromethyl)chromen-4-one;
3-(4-hydroxyphenyl)-7-({5-[4-methoxy-3-(trifluoromethyl)phenyl](1,2,4-oxadiazol-3-yl)}methoxy)-2-(trifluoromethyl)chromen-4-one;
3-(4-hydroxyphenyl)-7-{[5-(3-(1H-1,2,3,4-tetrazol-5-yl)phenyl)(1,2,4-oxadiazol-3-yl)]methoxy}chromen-4-one;
3-(3-{[3-(4-hydroxyphenyl)-4-oxochromen-7-yloxy]methyl}-1,2,4-oxadiazol-5-yl)benzoic acid;
3-[(3-{4-[(methylsulfonyl)amino]phenyl}-4-oxochromen-7-yloxy)methyl]benzoic acid;
3-{4-[(methylsulfonyl)amino]phenyl}-7-({5-[3-(trifluoromethyl)phenyl](1,2,4-oxadiazol-3-yl)}methoxy)chromen-4-one;
7-{[5-(3-fluorophenyl)(1,2,4-oxadiazol-3-yl)]methoxy}-3-(4-hydroxyphenyl)chromen-4-one;
3-{4-[(methylsulfonyl)amino]phenyl}-7-({2-[4-(trifluoromethyl)phenyl](1,3-thiazol-5-yl)}methoxy)chromen-4-one.
4-[7-({5-[3-fluoro-5-(trifluoromethyl)phenyl](1,2,4-oxadiazol-3-yl)}methoxy)-4-oxochromen-3-yl]benzenecarbonitrile;
ethyl 4-[7-({4-methyl-2-[4-(trifluoromethyl)phenyl](1,3-thiazol-5-yl)}methoxy)-4-oxochromen-3-yl]benzoate;
7-({3-[5-fluoro-3-(trifluoromethyl)phenyl](1,2,4-oxadiazol-5-yl)}ethoxy)-3-(4-hydroxyphenyl)chromen-4-one;
ethyl 3-[7-({5-[3-fluoro-5-(trifluoromethyl)phenyl](1,2,4-oxadiazol-3-yl)}methoxy)-4-oxochromen-3-yl]benzoate;
3-{4-[(methylsulfonyl)amino]phenyl}-7-({4-methyl-2-[4-(trifluoromethyl)phenyl](1,3-thiazol-5-yl)}methoxy)chromen-4-one;
methyl 4-[7-({4-methyl-2-[4-(trifluoromethyl)phenyl](1,3-thiazol-5-yl)}methoxy)-4-oxochromen-3-yl]benzoate;
3-(2H,3H-benzo[e]1,4-dioxan-6-yl)-7-({5-[3-fluoro-5-(trifluoromethyl)phenyl](1,2,4-oxadiazol-3-yl)}methoxy)chromen-4-one;
7-({5-[3-fluoro-5-(trifluoromethyl)phenyl](1,2,4-oxadiazol-3-yl)}methoxy)-3-(6-methoxy(3-pyridyl))chromen-4-one;
3-(4-hydroxyphenyl)-7-({4-methyl-2-[4-(trifluoromethyl)phenyl](1,3-thiazol-5-yl)}methoxy)chromen-4-one;
7-({5-[3-fluoro-5-(trifluoromethyl)phenyl](1,2,4-oxadiazol-3-yl)}methoxy)-3-(4-{[(4-methylphenyl)sulfonyl]amino}phenyl)chromen-4-one;
3-(4-{[(4-methylphenyl)sulfonyl]amino}phenyl)-7-({4-methyl-2-[4-(trifluoromethyl)phenyl](1,3-thiazol-5-yl)}methoxy)chromen-4-one;
methyl 3-{[3-(6-methoxy(3-pyridyl))-4-oxochromen-7-yloxy]methyl}benzoate;
methyl 3-({3-[4-(hydroxymethyl)phenyl]-4-oxochromen-7-yloxy}methyl)benzoate;
7-({5-[3-fluoro-5-(trifluoromethyl)phenyl](1,2,4-oxadiazol-3-yl)}methoxy)-3-[4-(hydroxymethyl)phenyl]chromen-4-one;
4-[7-({5-[3-fluoro-5-(trifluoromethyl)phenyl](1,2,4-oxadiazol-3-yl)}methoxy)-4-oxochromen-3-yl]benzoic acid;

7-({5-[3-fluoro-5-(trifluoromethyl)phenyl](1,2,4-oxadiazol-3-yl)}methoxy)-3-(4-morpholin-4-ylphenyl)chromen-4-one;

7-({5-methyl-2-[4-(trifluoromethyl)phenyl](1,3-thiazol-4-yl)}methoxy)-3-(4-morpholin-4-ylphenyl)chromen-4-one;

7-({3-[5-fluoro-3-(trifluoromethyl)phenyl](1,2,4-oxadiazol-5-yl)}methoxy)-3-{4-[(methylsulfonyl)amino]phenyl}chromen-4-one;

2-fluoro-5-[7-({5-[5-fluoro-3-(trifluoromethyl)phenyl](1,2,4-oxadiazol-3-yl)}methoxy)-4-oxochromen-3-yl]benzenecarbonitrile;

ethyl 2-(3-{4-[(ethoxycarbonyl)methoxy]phenyl}-4-oxochromen-7-yloxy)acetate;

7-{[5-(4-fluorophenyl)(1,2,4-oxadiazol-3-yl)]methoxy}-3-(4-hydroxyphenyl)chromen-4-one;

3-[7-({5-[5-fluoro-3-(trifluoromethyl)phenyl](1,2,4-oxadiazol-3-yl)}methoxy)-4-oxochromen-3-yl]benzenecarbonitrile;

3-(3-acetylphenyl)-7-({5-[5-fluoro-3-(trifluoromethyl)phenyl](1,2,4-oxadiazol-3-yl)}methoxy)chromen-4-one;

7-({5-[5-fluoro-3-(trifluoromethyl)phenyl](1,2,4-oxadiazol-3-yl)}methoxy)-3-{4-[(methylsulfonyl)amino]phenyl}chromen-4-one;

4-[7-({5-[5-fluoro-3-(trifluoromethyl)phenyl](1,2,4-oxadiazol-3-yl)}methoxy)-4-oxochromen-3-yl]benzamide;

3-[2,4-bis(tert-butoxy)pyrimidin-5-yl]-7-({5-[5-fluoro-3-(trifluoromethyl)phenyl](1,2,4-oxadiazol-3-yl)}methoxy)chromen-4-one;

5-[7-({5-[5-fluoro-3-(trifluoromethyl)phenyl](1,2,4-oxadiazol-3-yl)}methoxy)-4-oxochromen-3-yl]-1,3-dihydropyrimidine-2,4-dione;

7-({2-[5-fluoro-3-(trifluoromethyl)phenyl]-(1,3-oxazol-4-yl)}methoxy)-3-(4-hydroxyphenyl)chromen-4-one;

3-(4-hydroxyphenyl)-7-({2-[3-(trifluoromethyl)phenyl](1,3-oxazol-4-yl)}methoxy)chromen-4-one;

7-({2-[5-fluoro-3-(trifluoromethyl)phenyl](1,3-oxazol-4-yl)}methoxy)-3-(4-hydroxyphenyl)chromen-4-one;

3-(4-hydroxyphenyl)-7-{[2-(3,4,5-trifluorophenyl)(1,3-oxazol-4-yl)]methoxy}chromen-4-one;

7-{[2-(3,5-difluorophenyl)(1,3-oxazol-4-yl)]methoxy}-3-(4-hydroxyphenyl)chromen-4-one;

7-{[2-(3,4-difluorophenyl)(1,3-oxazol-4-yl)]methoxy}-3-(4-hydroxyphenyl)chromen-4-one;

7-{[2-(4-fluorophenyl)(1,3-oxazol-4-yl)]methoxy}-3-(4-hydroxyphenyl)chromen-4-one;

7-{[2-(4-chlorophenyl)(1,3-oxazol-4-yl)]methoxy}-3-(4-hydroxyphenyl)chromen-4-one;

methyl 3-{[3-(4-hydroxyphenyl)-4-oxochromen-7-yloxy]methyl}benzoate;

3-(4-hydroxyphenyl)-7-({3-[3-(trifluoromethyl)phenyl](1,2,4-oxadiazol-5-yl)}methoxy)chromen-4-one;

3-(4-hydroxyphenyl)-2-(trifluoromethyl)-7-({5-[3-(trifluoromethyl)phenyl]-(1,2,4-oxadiazol-3-yl)}methoxy)chromen-4-one;

3-{[3-(4-hydroxyphenyl)-4-oxochromen-7-yloxy]methyl}benzenecarbonitrile;

3-(4-hydroxyphenyl)-7-({5-[3-(trifluoromethyl)phenyl]isoxazol-3-yl}methoxy)chromen-4-one;

7-{[5-(trifluoromethyl)(3-pyridyl)]methoxy}-3-(4-{[6-(trifluoromethyl)(3-pyridyl)]methoxy}phenyl)chromen-4-one;

3-(4-hydroxyphenyl)-7-[(5-(3-pyridyl)(1,2,4-oxadiazol-3-yl))methoxy]chromen-4-one;

3-(4-hydroxyphenyl)-7-[(5-(2-pyridyl)(1,2,4-oxadiazol-3-yl))methoxy]chromen-4-one;

methyl 2-{[3-(4-hydroxyphenyl)-4-oxochromen-7-yloxy]methyl}-1,3-oxazole-5-carboxylate;

7-{[5-(4-fluorophenyl)(1,2,4-oxadiazol-3-yl)]methoxy}-3-{4-[(methylsulfonyl)amino]-phenyl}chromen-4-one;

2-{[3-(4-hydroxyphenyl)-4-oxochromen-7-yloxy]methyl}-1,3-oxazole-5-carboxylic acid;

methyl 3-({3-[4-((1Z)-1-amino-2-methoxy-2-azavinyl)phenyl]-4-oxochromen-7-yloxy}methyl)benzoate;

7-{2-[4-(4-chlorophenyl)pyrazolyl]ethoxy}-3-(4-hydroxyphenyl)chromen-4-one;

3-(4-hydroxyphenyl)-7-[(6-pyrazolyl(3-pyridyl))methoxy]chromen-4-one;

7-[(2R)-2-hydroxy-3-({[3-(trifluoromethyl)phenyl]methyl}amino)propoxy]-3-(4-hydroxyphenyl)chromen-4-one;

3-(4-hydroxyphenyl)-7-[({[3-(trifluoromethyl)phenyl]methyl}amino)methoxy]chromen-4-one;

7-((2R)-3-{[(3,5-difluorophenyl)methyl]amino}-2-hydroxypropoxy)-3-(4-hydroxyphenyl)chromen-4-one;

7-(3-{[(1R)-1-(4-fluorophenyl)ethyl]amino}-2-oxopropoxy)-3-(4-hydroxyphenyl)chromen-4-one;

3-(4-hydroxyphenyl)-7-(3-phenylpropoxy)chromen-4-one;

7-{[5-(3-fluorophenyl)(1,3,4-oxadiazol-2-yl)]methoxy}-3-(4-hydroxyphenyl)chromen-4-one;

3-(4-hydroxyphenyl)-7-{[3-(trifluoromethyl)phenyl]ethoxy}chromen-4-one;

3-(4-hydroxyphenyl)-7-({5-[3-(trifluoromethyl)phenyl](1,3,4-oxadiazol-2-yl)}methoxy)chromen-4-one;

3-(4-hydroxyphenyl)-7-[(2-phenyl(1,3-oxazol-5-yl))methoxy]chromen-4-one;

7-({5-[3,5-bis(trifluoromethyl)phenyl]isoxazol-3-yl}methoxy)-3-(4-hydroxyphenyl)chromen-4-one;

3-(4-hydroxyphenyl)-7-({5-[3-(trifluoromethyl)phenyl]isoxazol-3-yl}methoxy)chromen-4-one;

3-{4-[(methylsulfonyl)amino]phenyl}-7-[(2-phenyl(1,3-oxazol-4-yl))methoxy]chromen-4-one;

2-[3-(4-hydroxyphenyl)-4-oxochromen-7-yloxy]-N-[3-(trifluoromethyl)phenyl]-acetamide;

7-{[5-(2-chlorophenyl)(1,3,4-thiadiazol-2-yl)]methoxy}-3-(4-hydroxyphenyl)chromen-4-one;

4-[7-({4-methyl-2-[4-(trifluoromethyl)phenyl](1,3-thiazol-5-yl)}methoxy)-4-oxochromen-3-yl]benzenecarbonitrile;

3-{4-[(methylsulfonyl)amino]phenyl}-7-({4-methyl-2-[4-(trifluoromethyl)phenyl](1,3-thiazol-5-yl)}methoxy)chromen-4-one;

3-(6-methoxy(3-pyridyl))-7-({4-methyl-2-[4-(trifluoromethyl)phenyl](1,3-thiazol-5-yl)}methoxy)chromen-4-one;

4-[7-({5-[5-fluoro-3-(trifluoromethyl)phenyl](1,3,4-oxadiazol-2-yl)}methoxy)-4-oxochromen-3-yl]benzenecarbonitrile;

4-[4-oxo-7-({3-[3-(trifluoromethyl)phenyl]isoxazol-5-yl}methoxy)chromen-3-yl]benzenecarbonitrile;

7-({5-[3-fluoro-5-(trifluoromethyl)phenyl](1,2,4-oxadiazol-3-yl)}methoxy)-3-{4-[(methylsulfonyl)amino]phenyl}chromen-4-one;

7-({5-[3-fluoro-5-(trifluoromethyl)phenyl](1,2,4-oxadiazol-3-yl)}methoxy)-3-[4-(methylsulfonyl)phenyl]chromen-4-one;

4-[7-({5-[3-fluoro-5-(trifluoromethyl)phenyl](1,2,4-oxadiazol-3-yl)}methoxy)-4-oxochromen-3-yl]benzamide;

3-(3-acetylphenyl)-7-({5-[3-fluoro-5-(trifluoromethyl)phenyl](1,2,4-oxadiazol-3-yl)}methoxy)chromen-4-one;

7-({5-[3-fluoro-5-(trifluoromethyl)phenyl](1,3,4-oxadiazol-2-yl)}methoxy)-3-(4-hydroxyphenyl)chromen-4-one;

7-({5-[3-fluoro-5-(trifluoromethyl)phenyl](1,2,4-oxadiazol-3-yl)}methoxy)-3-(5-hydropyrazol-4-yl)chromen-4-one;

ethyl 3-[7-({3-[3-fluoro-5-(trifluoromethyl)phenyl](1,2,4-oxadiazol-5-yl)}ethoxy)-4-oxochromen-3-yl]benzoate;
3-(4-hydroxyphenyl)-7-({2-[4-(trifluoromethyl)phenyl](1,3-thiazol-5-yl)}methoxy)chromen-4-one;
7-[2-(3-fluorophenyl)-2-oxoethoxy]-3-(4-hydroxyphenyl)chromen-4-one;
7-({5-[3-fluoro-5-(trifluoromethyl)phenyl](1,2,4-oxadiazol-3-yl)}ethoxy)-3-(4-hydroxyphenyl)chromen-4-one;
7-({5-[3-fluoro-5-(trifluoromethyl)phenyl](1,2,4-oxadiazol-3-yl)}methoxy)-3-(4-{[(4-methylphenyl)sulfonyl]amino}phenyl)chromen-4-one;
7-{[5-(2-chlorophenyl)(1,3,4-oxadiazol-2-yl)]methoxy}-3-(4-hydroxyphenyl)chromen-4-one;
7-{[5-(4-fluorophenyl)(1,3,4-oxadiazol-2-yl)]methoxy}-3-(4-hydroxyphenyl)chromen-4-one;
3-(4-hydroxyphenyl)-7-(4-pyridylmethoxy)chromen-4-one;
3-{4-[(methylsulfonyl)amino]phenyl}-7-({2-[4-(trifluoromethyl)phenyl](1,3-thiazol-5-yl)}methoxy)chromen-4-one;
2-[3-(4-hydroxyphenyl)-4-oxochromen-7-yloxy]-N-[2-(trifluoromethyl)phenyl]-acetamide;
3-(4-hydroxyphenyl)-7-{2-oxo-2-[2-(trifluoromethyl)phenyl]ethoxy}chromen-4-one;
3-(1H-indazol-5-yl)-7-({5-[5-fluoro-3-(trifluoromethyl)phenyl](1,2,4-oxadiazol-3-yl)}methoxy)chromen-4-one;
3-(4-hydroxyphenyl)-7-(2-phenylethoxy)chromen-4-one;
2-[3-(4-hydroxyphenyl)-4-oxochromen-7-yloxy]ethanenitrile;
7-[2-(4-chlorophenoxy)ethoxy]-3-(4-hydroxyphenyl)chromen-4-one;
5-{4-[7-({5-[5-fluoro-3-(trifluoromethyl)phenyl](1,2,4-oxadiazol-3-yl)}methoxy)-4-oxochromen-3-yl]phenyl}-1,3,5,6-tetrahydropyrimidine-2,4-dione;
N-[(1R)-1-(4-fluorophenyl)ethyl]-2-[3-(4-hydroxyphenyl)-4-oxochromen-7-yloxy]acetamide;
3-(4-hydroxyphenyl)-7-(2-pyridylmethoxy)chromen-4-one;
2-fluoro-5-[7-({5-[5-fluoro-3-(trifluoromethyl)phenyl](1,2,4-oxadiazol-3-yl)}methoxy)-4-oxochromen-3-yl]benzenecarbonitrile;
7-(2-pyridylmethoxy)-3-[4-(2-pyridylmethoxy)phenyl]chromen-4-one;
3-(4-hydroxyphenyl)-7-[(5-(4-pyridyl)(1,2,4-oxadiazol-3-yl))ethoxy]chromen-4-one;
3-(4-hydroxyphenyl)-7-[(5-(3-pyridyl)(1,2,4-oxadiazol-3-yl))ethoxy]chromen-4-one;
3-(4-hydroxyphenyl)-7-[(5-(2-pyridyl)(1,2,4-oxadiazol-3-yl))ethoxy]chromen-4-one;
3-(4-hydroxyphenyl)-7-{[5-(trifluoromethyl)(3-pyridyl)]methoxy}chromen-4-one;
7-{[5-(4-chlorophenyl)isoxazol-3-yl]methoxy}-3-(4-hydroxyphenyl)chromen-4-one;
7-{[5-(3,4-dichlorophenyl)isoxazol-3-yl]methoxy}-3-(4-hydroxyphenyl)chromen-4-one;
7-{[5-(4-chlorophenyl)isoxazol-3-yl]methoxy}-3-(4-hydroxyphenyl)chromen-4-one;
7-[(2R)-2-hydroxy-3-({[3-(trifluoromethyl)phenyl]methyl}amino)propoxy]-3-(4-hydroxyphenyl)chromen-4-one;
3-(4-hydroxyphenyl)-7-[2-({[3-(trifluoromethyl)phenyl]methyl}amino)ethoxy]chromen-4-one;
7-((2R)-3-{[(3,5-difluorophenyl)methyl]amino}-2-hydroxypropoxy)-3-(4-hydroxyphenyl)chromen-4-one;
methyl 2-{[3-(4-hydroxyphenyl)-4-oxochromen-7-yloxy]methyl}-1,3-oxazole-4-carboxylate;
2-{[3-(4-hydroxyphenyl)-4-oxochromen-7-yloxy]methyl}-1,3-oxazole-4-carboxylic acid;
N-[(1S)-1-(4-fluorophenyl)ethyl]-2-[3-(4-hydroxyphenyl)-4-oxochromen-7-yloxy]acetamide;
7-{[5-(4-fluorophenyl)(1,2,4-oxadiazol-3-yl)]methoxy}-3-(4-hydroxyphenyl)chromen-4-one;
7-{[5-(4-fluorophenyl)(1,2,4-oxadiazol-3-yl)]methoxy}-3-{4-[(methylsulfonyl)amino]-phenyl}chromen-4-one;
7-{3-[4-(4-chlorophenyl)pyrazolyl]propoxy}-3-(4-hydroxyphenyl)chromen-4-one;
3-(4-hydroxyphenyl)-7-(3-phenylpropoxy)chromen-4-one;
3-(4-hydroxyphenyl)-7-[(6-pyrazolyl(3-pyridyl))methoxy]chromen-4-one;
7-((2R)-2-hydroxy-3-phenylpropoxy)-3-(4-hydroxyphenyl)chromen-4-one;
3-(4-hydroxyphenyl)-7-[(5-(3-pyridyl)(1,3,4-oxadiazol-2-yl))methoxy]chromen-4-one;
3-[(2-hydroxy-3-{4-[(methylsulfonyl)amino]phenyl}-4-oxochromen-7-yloxy)methyl]benzoic acid;
7-{[5-(4-fluorophenyl)(1,3,4-oxadiazol-2-yl)]ethoxy}-3-(4-hydroxyphenyl)chromen-4-one;
3-(4-hydroxyphenyl)-7-[(5-(3-pyridyl)(1,3,4-oxadiazol-2-yl))ethoxy]chromen-4-one;
3-(4-hydroxyphenyl)-7-[(3-(3-pyridyl)(1,2,4-oxadiazol-5-yl))methoxy]chromen-4-one;
3-(4-hydroxyphenyl)-7-[(5-(3-pyridyl)(1,3,4-oxadiazol-2-yl))ethoxy]chromen-4-one;
3-(4-hydroxyphenyl)-7-[(5-(4-pyridyl)(1,2,4-oxadiazol-3-yl))ethoxy]chromen-4-one;
(2-{[3-(4-hydroxyphenyl)-4-oxochromen-7-yloxy]methyl}(1,3-oxazol-4-yl))-N-methylcarboxamide;
4-{[3-(4-hydroxyphenyl)-4-oxochromen-7-yloxy]methyl}-7-methoxychromen-2-one;
7-{[5-(4-fluorophenyl)(1,3,4-oxadiazol-2-yl)]methoxy}-3-{4-[(methylsulfonyl)amino]-phenyl}chromen-4-one;
7-{[5-(3-aminophenyl)(1,3,4-oxadiazol-2-yl)]methoxy}-3-(4-hydroxyphenyl)chromen-4-one;
ethyl 1-{2-[3-(4-hydroxyphenyl)-4-oxochromen-7-yloxy]ethyl}pyrazole-4-carboxylate;
7-{2-[4-(3-chlorophenyl)piperazinyl]ethoxy}-3-(4-hydroxyphenyl)chromen-4-one;
3-(4-hydroxyphenyl)-7-(2-{4-[3-(trifluoromethyl)phenyl]piperazinyl}ethoxy)chromen-4-one;
3-(4-hydroxyphenyl)-7-[(5-(2-pyridyl)isoxazol-3-yl)methoxy]chromen-4-one;
7-({3-[3-fluoro-5-(trifluoromethyl)phenyl](1,2,4-oxadiazol-5-yl)}ethoxy)-3-(4-hydroxyphenyl)chromen-4-one;
7-[2-(4-fluorophenyl)ethoxy]-3-(4-hydroxyphenyl)chromen-4-one;
7-((1R)-1-{3-[3-fluoro-5-(trifluoromethyl)phenyl](1,2,4-oxadiazol-5-yl)}ethoxy)-3-(4-hydroxyphenyl)chromen-4-one;
7-((1S)-1-{3-[3-fluoro-5-(trifluoromethyl)phenyl](1,2,4-oxadiazol-5-yl)}ethoxy)-3-(4-hydroxyphenyl)chromen-4-one;
3-(4-hydroxyphenyl)-7-{2-[3-(trifluoromethyl)pyrazolyl]ethoxy}chromen-4-one;
7-(1-{3-[3-fluoro-5-(trifluoromethyl)phenyl](1,2,4-oxadiazol-5-yl)}-isopropoxy)-3-(4-hydroxyphenyl)chromen-4-one;
3-(4-hydroxyphenyl)-7-[(3-(1H-1,2,3,4-tetrazol-5-yl)phenyl)methoxy]chromen-4-one;
prop-2-enyl 3-{[3-(4-aminophenyl)-4-oxochromen-7-yloxy]methyl}benzoate
3-(4-aminophenyl)-7-({5-[3-(trifluoromethyl)phenyl](1,2,4-oxadiazol-3-yl)}methoxy)chromen-4-one;
methyl 3-{[3-(4-aminophenyl)-4-oxochromen-7-yloxy]methyl}benzoate;
7-({5-[5-fluoro-3-(trifluoromethyl)phenyl](1,2,4-oxadiazol-3-yl)}methoxy)-3-(4-aminophenyl)chromen-4-one);

3-{[3-(4-aminophenyl)-4-oxochromen-7-yloxy]
  methyl}benzenecarbonitrile;
3-{[3-(4-aminophenyl)-4-oxochromen-7-yloxy]
  methyl}benzamide;
prop-2-enyl 3-[(3-{4-[(methylsulfonyl)amino]phenyl}-4-
  oxochromen-7-yloxy)methyl]benzoate
methyl 3-[(3-{4-[(methylsulfonyl)amino]phenyl}-4-oxo-
  chromen-7-yloxy)methyl]benzoate;
7-({5-[5-fluoro-3-(trifluoromethyl)phenyl](1,2,4-oxadiazol-
  3-yl)}methoxy)-3-{4-[(methylsulfonyl)amino]
  phenyl}chromen-4-one;
3-[(3-{4-[(methylsulfonyl)amino]phenyl}-4-oxochromen-
  7-yloxy)methyl]-benzenecarbonitrile;
3-{[3-(4-methylsulfonylaminophenyl)-4-oxochromen-7-
  yloxy]methyl}benzamide;
3-{[3-(4-hydroxyphenyl)-4-oxochromen-7-yloxy]
  methyl}benzoic acid;
3-(3-{[3-(4-hydroxyphenyl)-4-oxochromen-7-yloxy]me-
  thyl}-1,2,4-oxadiazol-5-yl)benzoic acid;
methyl 3-({3-[4-(acetylamino)phenyl]-4-oxochromen-7-
  yloxy}methyl)benzoate;
3-(4-hydroxyphenyl)-7-{2-[4-(4-methoxyphenyl)piperazi-
  nyl]ethoxy}chromen-4-one;
7-{2-[4-(4-fluorophenyl)piperazinyl]ethoxy}-3-(4-hydrox-
  yphenyl)chromen-4-one;
3-(4-hydroxyphenyl)-7-(2-piperazinylethoxy)chromen-4-
  one;
N-(3-fluorophenyl)(4-{2-[3-(4-hydroxyphenyl)-4-oxo-
  chromen-7-yloxy]ethyl}-piperazinyl)carboxamide;
7-[2-(4-{[(3-fluorophenyl)amino]
  thioxomethyl}piperazinyl)ethoxy]-3-(4-hydroxyphenyl)
  chromen-4-one;
N-(2,4-difluorophenyl)(4-{2-[3-(4-hydroxyphenyl)-4-oxo-
  chromen-7-yloxy]ethyl}piperazinyl)carboxamide;
7-(2-{2-[3-fluoro-5-(trifluoromethyl)phenyl](1,3-oxazol-5-
  yl)}ethoxy)-3-(4-hydroxyphenyl)chromen-4-one;
7-(3-{2-[3-fluoro-5-(trifluoromethyl)phenyl](1,3-oxazol-4-
  yl)}propoxy)-3-(4-hydroxyphenyl)chromen-4-one;
7-[2-(4-fluorophenyl)-2-oxoethoxy]-3-(4-hydroxyphenyl)
  chromen-4-one;
7-[2-(3-fluorophenyl)-2-oxoethoxy]-3-(4-hydroxyphenyl)
  chromen-4-one;
3-(4-hydroxyphenyl)-7-{2-oxo-2-[2-(trifluoromethyl)phe-
  nyl]ethoxy}chromen-4-one;
3-(4-hydroxyphenyl)-7-{2-oxo-2-[2-(trifluoromethyl)phe-
  nyl]ethoxy}chromen-4-one;
2-[3-(4-hydroxyphenyl)-4-oxochromen-7-yloxy]-N-[3-(trif-
  luoromethyl)phenyl]-acetamide;
N-[(1S)-1-(4-fluorophenyl)ethyl]-2-[3-(4-hydroxyphenyl)-
  4-oxochromen-7-yloxy]acetamide;
2-[3-(4-hydroxyphenyl)-4-oxochromen-7-yloxy]-N-[2-(trif-
  luoromethyl)-phenyl]acetamide;
N-(3-fluorophenyl)-2-[3-(4-hydroxyphenyl)-4-oxo-
  chromen-7-yloxy]acetamide;
N-[(1R)-1-(4-fluorophenyl)ethyl]-2-[3-(4-hydroxyphenyl)-
  4-oxochromen-7-yloxy]acetamide;
3-(4-hydroxyphenyl)-7-[2-hydroxy-3-({[3-(trifluoromethyl)
  phenyl]methyl}amino)-propoxy]chromen-4-one;
7-(3-{[(3,5-difluorophenyl)methyl]amino}-2-hydroxypro-
  poxy)-3-(4-hydroxyphenyl)chromen-4-one;
7-(2-{[(4-fluorophenyl)ethyl]amino}ethoxy)-3-(4-hydrox-
  yphenyl)chromen-4-one;
3-(4-hydroxyphenyl)-7-(2-hydroxy-3-phenylpropoxy)
  chromen-4-one;
7-((1R)-1-{3-[5-fluoro-3-(trifluoromethyl)phenyl](1,2,4-
  oxadiazol-5-yl)}ethoxy)-3-(4-hydroxyphenyl)chromen-
  4-one 2-morpholinoethyl 3-((3-(4-(methylsulfonamido)phenyl)-4-
  oxo-4H-chromen-7-yloxy)methyl)benzoate;
ethyl 3-((3-(4-(methylsulfonamido)phenyl)-4-oxo-4H-
  chromen-7-yloxy)methyl)benzoate;
2-(dimethylamino)ethyl 3-((3-(4-(methylsulfonamido)phe-
  nyl)-4-oxo-4H-chromen-7-yloxy)methyl)benzoate; and
2-(4-methylpiperazin-1-yl)ethyl 3-((3-(4-(methylsulfona-
  mido)phenyl)-4-oxo-4H-chromen-7-yloxy)methyl)ben-
  zoate.

SUMMARY OF THE FIGURE

The FIGURE depicts how increasing doses of 3-[(3-{4-[(methylsulfonyl)amino]phenyl}-4-oxochromen-7-yloxy) methyl]benzoic acid administered as described in the protocol described in Example 32 reduced the number of bar presses (plotted as the number of infusions).

DETAILED DESCRIPTION OF THE INVENTION

Definitions and General Parameters

As used in the present specification, the following words and phrases are generally intended to have the meanings as set forth below, except to the extent that the context in which they are used indicates otherwise.

The term "alkyl" refers to a monoradical branched or unbranched saturated hydrocarbon chain having 1, 2, 3, 4, 5, 6, 7, 8, 9, 10, 11, 12, 13, 14, 15, 16, 17, 18, 19 or 20 carbon atoms. This term is exemplified by groups such as methyl, ethyl, n-propyl, iso-propyl, n-butyl, iso-butyl, t-butyl, n-hexyl, n-decyl, tetradecyl, and the like.

The term "substituted alkyl" refers to:

1) an alkyl group as defined above, having 1, 2, 3, 4 or 5 substituents, preferably 1 to 3 substituents, selected from the group consisting of alkenyl, alkynyl, alkoxy, cycloalkyl, cycloalkenyl, acyl, acylamino, acyloxy, amino, aminocarbonyl, alkoxycarbonylamino, azido, cyano, halogen, hydroxy, keto, thiocarbonyl, carboxyl, carboxyalkyl, arylthio, heteroarylthio, heterocyclylthio, thiol, alkylthio, aryl, aryloxy, heteroaryl, aminosulfonyl, aminocarbonylamino, heteroaryloxy, heterocyclyl, heterocyclooxy, hydroxyamino, alkoxyamino, nitro, —SO-alkyl, —SO-aryl, —SO-heteroaryl, —SO$_2$-alkyl, SO$_2$-aryl and —SO$_2$-heteroaryl. Unless otherwise constrained by the definition, all substituents may optionally be further substituted by 1, 2, or 3 substituents chosen from alkyl, carboxyl, carboxyalkyl, aminocarbonyl, hydroxy, alkoxy, halogen, CF$_3$, amino, substituted amino, cyano, and —S(O)$_n$R, where R is alkyl, aryl, or heteroaryl and n is 0, 1 or 2; or 2) an alkyl group as defined above that is interrupted by 1-10 atoms independently chosen from oxygen, sulfur and NR$_a$—, where R$_a$ is chosen from hydrogen, alkyl, cycloalkyl, alkenyl, cycloalkenyl, alkynyl, aryl, heteroaryl and heterocyclyl. All substituents may be optionally further substituted by alkyl, alkoxy, halogen, CF$_3$, amino, substituted amino, cyano, or —S(O)$_n$R, in which R is alkyl, aryl, or heteroaryl and n is 0, 1 or 2; or 3) an alkyl group as defined above that has both 1, 2, 3, 4 or 5 substituents as defined above and is also interrupted by 1-10 atoms as defined above.

The term "lower alkyl" refers to a monoradical branched or unbranched saturated hydrocarbon chain having 1, 2, 3, 4, 5, or 6 carbon atoms. This term is exemplified by groups such as methyl, ethyl, n-propyl, iso-propyl, n-butyl, iso-butyl, t-butyl, n-hexyl, and the like.

The term "substituted lower alkyl" refers to lower alkyl as defined above having 1 to 5 substituents, preferably 1, 2, or 3 substituents, as defined for substituted alkyl, or a lower alkyl group as defined above that is interrupted by 1, 2, 3, 4, or 5 atoms as defined for substituted alkyl, or a lower alkyl group as defined above that has both 1, 2, 3, 4 or 5 substituents as defined above and is also interrupted by 1, 2, 3, 4, or 5 atoms as defined above.

The term "alkylene" refers to a diradical of a branched or unbranched saturated hydrocarbon chain, having 1, 2, 3, 4, 5, 6, 7, 8, 9, 10, 11, 12, 13, 14, 15, 16, 17, 18, 19 or 20 carbon atoms, preferably 1-10 carbon atoms, more preferably 1, 2, 3, 4, 5 or 6 carbon atoms. This term is exemplified by groups such as methylene (—$CH_2$—), ethylene (—$CH_2CH_2$—), the propylene isomers (e.g., —$CH_2CH_2CH_2$— and —$CH(CH_3)CH_2$—) and the like.

The term "lower alkylene" refers to a diradical of a branched or unbranched saturated hydrocarbon chain, preferably having from 1, 2, 3, 4, 5, or 6 carbon atoms.

The term "lower alkylene" refers to a diradical of a branched or unbranched saturated hydrocarbon chain, preferably having from 1, 2, 3, 4, 5, or 6 carbon atoms.

The term "substituted alkylene" refers to:
(1) an alkylene group as defined above having 1, 2, 3, 4, or 5 substituents selected from the group consisting of alkyl, alkenyl, alkynyl, alkoxy, cycloalkyl, cycloalkenyl, acyl, acylamino, acyloxy, amino, aminocarbonyl, alkoxycarbonylamino, azido, cyano, halogen, hydroxy, keto, thiocarbonyl, carboxyl, carboxyalkyl, arylthio, heteroarylthio, heterocyclylthio, thiol, alkylthio, aryl, aryloxy, heteroaryl, aminosulfonyl, aminocarbonylamino, heteroaryloxy, heterocyclyl, heterocyclooxy, hydroxyamino, alkoxyamino, nitro, —SO-alkyl, —SO-aryl, —SO-heteroaryl, —$SO_2$-alkyl, $SO_2$-aryl and —$SO_2$-heteroaryl. Unless otherwise constrained by the definition, all substituents may optionally be further substituted by 1, 2, or 3 substituents chosen from alkyl, carboxyl, carboxyalkyl, aminocarbonyl, hydroxy, alkoxy, halogen, $CF_3$, amino, substituted amino, cyano, and —$S(O)_nR$, where R is alkyl, aryl, or heteroaryl and n is 0, 1 or 2; or
(2) an alkylene group as defined above that is interrupted by 1-20 atoms independently chosen from oxygen, sulfur and $NR_a$—, where $R_a$ is chosen from hydrogen, optionally substituted alkyl, cycloalkyl, cycloalkenyl, aryl, heteroaryl and heterocycyl, or groups selected from carbonyl, carboxyester, carboxyamide and sulfonyl; or
(3) an alkylene group as defined above that has both 1, 2, 3, 4 or 5 substituents as defined above and is also interrupted by 1-20 atoms as defined above. Examples of substituted alkylenes are chloromethylene (—CH(Cl)—), aminoethylele (—CH($NH_2$)$CH_2$—), methylaminoethylene (—CH(NHMe)$CH_2$—), 2-carboxypropylene isomers (—$CH_2$CH($CO_2H$)$CH_2$—), ethoxyethyl (—$CH_2CH_2$O—$CH_2CH_2$—), ethylmethylaminoethyl (—$CH_2CH_2N(CH_3)CH_2CH_2$—), 1-ethoxy-2-(2-ethoxy-ethoxy)ethane (—$CH_2CH_2$O—$CH_2CH_2$—O$CH_2CH_2$—O$CH_2CH_2$—), and the like.

The term "aralkyl" refers to an aryl group covalently linked to an alkylene group, where aryl and alkylene are defined herein. "Optionally substituted aralkyl" refers to an optionally substituted aryl group covalently liked to an optionally substituted alkylene group. Such aralkyl groups are exemplified by benzyl, phenylethyl, 3-(4-methoxyphenyl)propyl, and the like.

The term "alkoxy" refers to the group R—O—, where R is optionally substituted alkyl or optionally substituted cycloalkyl, or R is a group —Y—Z, in which Y is optionally substituted alkylene and Z is optionally substituted alkenyl, optionally substituted alkynyl; or optionally substituted cycloalkenyl, where alkyl, alkenyl, alkynyl, cycloalkyl and cycloalkenyl are as defined herein. Preferred alkoxy groups are optionally substituted alkyl-O— and include, by way of example, methoxy, ethoxy, n-propoxy, iso-propoxy, n-butoxy, tert-butoxy, sec-butoxy, n-pentoxy, n-hexoxy, 1,2-dimethylbutoxy, trifluoromethoxy, and the like. The term "lower alkoxy" refers to the group R—O—, where R is optionally substituted lower alkyl as defined above.

The term "alkylthio" refers to the group R—S—, where R is as defined for alkoxy.

The term "alkenyl" refers to a monoradical of a branched or unbranched unsaturated hydrocarbon group preferably having from 2 to 20 carbon atoms, more preferably 2 to 10 carbon atoms and even more preferably 2 to 6 carbon atoms and having 1-6, preferably 1, double bond (vinyl). Preferred alkenyl groups include ethenyl or vinyl (—CH=$CH_2$), 1-propylene or allyl (—$CH_2$CH=$CH_2$), isopropylene (—C($CH_3$)=$CH_2$), bicyclo[2.2.1]heptene, and the like. In the event that alkenyl is attached to nitrogen, the double bond cannot be alpha to the nitrogen.

The term "lower alkenyl" refers to alkenyl as defined above having from 2 to 6 carbon atoms.

The term "substituted alkenyl" refers to an alkenyl group as defined above having 1, 2, 3, 4 or 5 substituents, and preferably 1, 2, or 3 substituents, selected from the group consisting of alkyl, alkenyl, alkynyl, alkoxy, cycloalkyl, cycloalkenyl, acyl, acylamino, acyloxy, amino, aminocarbonyl, alkoxycarbonylamino, azido, cyano, halogen, hydroxy, keto, thiocarbonyl, carboxyl, carboxyalkyl, arylthio, heteroarylthio, heterocyclylthio, thiol, alkylthio, aryl, aryloxy, heteroaryl, aminosulfonyl, aminocarbonylamino, heteroaryloxy, heterocyclyl, heterocyclooxy, hydroxyamino, alkoxyamino, nitro, —SO-alkyl, —SO-aryl, —SO-heteroaryl, —$SO_2$-alkyl, $SO_2$-aryl and —$SO_2$-heteroaryl Unless otherwise constrained by the definition, all substituents may optionally be further substituted by 1, 2, or 3 substituents chosen from alkyl, carboxyl, carboxyalkyl, aminocarbonyl, hydroxy, alkoxy, halogen, $CF_3$, amino, substituted amino, cyano, and —$S(O)_nR$, where R is alkyl, aryl, or heteroaryl and n is 0, 1 or 2.

The term "alkynyl" refers to a monoradical of an unsaturated hydrocarbon, preferably having from 2 to 20 carbon atoms, more preferably 2 to 10 carbon atoms and even more preferably 2 to 6 carbon atoms and having at least 1 and preferably from 1-6 sites of acetylene (triple bond) unsaturation. Preferred alkynyl groups include ethynyl, (—C≡CH), propargyl (or prop-1-yn-3-yl, —$CH_2$C≡CH), and the like. In the event that alkynyl is attached to nitrogen, the triple bond cannot be alpha to the nitrogen.

The term "substituted alkynyl" refers to an alkynyl group as defined above having 1, 2, 3, 4 or 5 substituents, and preferably 1, 2, or 3 substituents, selected from the group consisting of alkyl, alkenyl, alkynyl, alkoxy, cycloalkyl, cycloalkenyl, acyl, acylamino, acyloxy, amino, aminocarbonyl, alkoxycarbonylamino, azido, cyano, halogen, hydroxy, keto, thiocarbonyl, carboxyl, carboxyalkyl, arylthio, heteroarylthio, heterocyclylthio, thiol, alkylthio, aryl, aryloxy, heteroaryl, aminosulfonyl, aminocarbonylamino, heteroaryloxy, heterocyclyl, heterocyclooxy, hydroxyamino, alkoxyamino, nitro, —SO-alkyl, —SO-aryl, —SO-heteroaryl, —$SO_2$-alkyl, $SO_2$-aryl and —$SO_2$-heteroaryl. Unless otherwise constrained by the definition, all substituents may optionally be further substituted by 1, 2, or 3 substituents chosen from alkyl, carboxyl, carboxyalkyl, aminocarbonyl, hydroxy, alkoxy, halogen, $CF_3$, amino, substituted amino, cyano, and —S(O)$_n$R, where R is alkyl, aryl, or heteroaryl and n is 0, 1 or 2.

The term "aminocarbonyl" refers to the group —C(O)NRR where each R is independently hydrogen, alkyl, aryl, heteroaryl, heterocyclyl or where both R groups are joined to form a heterocyclic group (e.g., morpholino). Unless otherwise constrained by the definition, all substituents may optionally be further substituted by 1-3 substituents chosen from alkyl, carboxyl, carboxyalkyl, aminocarbonyl, hydroxy, alkoxy, halogen, CF$_3$, amino, substituted amino, cyano, and S(O)$_n$R, where R is alkyl, aryl, or heteroaryl and n is 0, 1 or 2.

The term "acylamino" refers to the group —NRC(O)R where each R is independently hydrogen, alkyl, aryl, heteroaryl, or heterocyclyl. Unless otherwise constrained by the definition, all substituents may optionally be further substituted by 1-3 substituents chosen from alkyl, carboxyl, carboxyalkyl, aminocarbonyl, hydroxy, alkoxy, halogen, CF$_3$, amino, substituted amino, cyano, and —S(O)$_n$R, where R is alkyl, aryl, or heteroaryl and n is 0, 1 or 2.

The term "acyloxy" refers to the groups —O(O)C-alkyl, —O(O)C-cycloalkyl, —O(O)C-aryl, —O(O)C-heteroaryl, and —O(O)C-heterocyclyl. Unless otherwise constrained by the definition, all substituents may be optionally further substituted by alkyl, carboxyl, carboxyalkyl, aminocarbonyl, hydroxy, alkoxy, halogen, CF$_3$, amino, substituted amino, cyano, or —S(O)$_n$R, where R is alkyl, aryl, or heteroaryl and n is 0, 1 or 2.

The term "aryl" refers to an aromatic carbocyclic group of 6 to 20 carbon atoms having a single ring (e.g., phenyl) or multiple rings (e.g., biphenyl), or multiple condensed (fused) rings (e.g., naphthyl or anthryl). Preferred aryls include phenyl, naphthyl and the like.

The term "arylene" refers to a diradical of an aryl group as defined above. This term is exemplified by groups such as 1,4-phenylene, 1,3-phenylene, 1,2-phenylene, 1,4'-biphenylene, and the like.

Unless otherwise constrained by the definition for the aryl or arylene substituent, such aryl or arylene groups can optionally be substituted with from 1 to 5 substituents, preferably 1 to 3 substituents, selected from the group consisting of alkyl, alkenyl, alkynyl, alkoxy, cycloalkyl, cycloalkenyl, acyl, acylamino, acyloxy, amino, aminocarbonyl, alkoxycarbonylamino, azido, cyano, halogen, hydroxy, keto, thiocarbonyl, carboxyl, carboxyalkyl, arylthio, heteroarylthio, heterocyclylthio, thiol, alkylthio, aryl, aryloxy, heteroaryl, aminosulfonyl, aminocarbonylamino, heteroaryloxy, heterocyclyl, heterocyclooxy, hydroxyamino, alkoxyamino, nitro, —SO-alkyl, —SO-aryl, —SO-heteroaryl, —SO$_2$-alkyl, SO$_2$-aryl and —SO$_2$-heteroaryl. Unless otherwise constrained by the definition, all substituents may optionally be further substituted by 1-3 substituents chosen from alkyl, carboxyl, carboxyalkyl, aminocarbonyl, hydroxy, alkoxy, halogen, CF$_3$, amino, substituted amino, cyano, and —S(O)$_n$R, where R is alkyl, aryl, or heteroaryl and n is 0, 1 or 2.

The term "aryloxy" refers to the group aryl-O— wherein the aryl group is as defined above, and includes optionally substituted aryl groups as also defined above. The term "arylthio" refers to the group R—S—, where R is as defined for aryl.

The term "amino" refers to the group —NH$_2$.

The term "substituted amino" refers to the group —NRR where each R is independently selected from the group consisting of hydrogen, alkyl, cycloalkyl, carboxyalkyl (for example, benzyloxycarbonyl), aryl, heteroaryl and heterocyclyl provided that both R groups are not hydrogen, or a group —Y—Z, in which Y is optionally substituted alkylene and Z is alkenyl, cycloalkenyl, or alkynyl, Unless otherwise constrained by the definition, all substituents may optionally be further substituted by 1-3 substituents chosen from alkyl, carboxyl, carboxyalkyl, aminocarbonyl, hydroxy, alkoxy, halogen, CF$_3$, amino, substituted amino, cyano, and S(O)$_n$R, where R is alkyl, aryl, or heteroaryl and n is 0, 1 or 2.

The term "carboxyalkyl" refers to the groups —C(O)O-alkyl or —C(O)O-cycloalkyl, where alkyl and cycloalkyl, are as defined herein, and may be optionally further substituted by alkyl, alkenyl, alkynyl, alkoxy, halogen, CF$_3$, amino, substituted amino, cyano, or —S(O)$_n$R, in which R is alkyl, aryl, or heteroaryl and n is 0, 1 or 2.

The term "cycloalkyl" refers to carbocyclic groups of from 3 to 20 carbon atoms having a single cyclic ring or multiple condensed rings. Such cycloalkyl groups include, by way of example, single ring structures such as cyclopropyl, cyclobutyl, cyclopentyl, cyclooctyl, and the like, or multiple ring structures such as adamantanyl, bicyclo[2.2.1]heptane, 1,3,3-trimethylbicyclo[2.2.1]hept-2-yl, (2,3,3-trimethylbicyclo[2.2.1]hept-2-yl), or carbocyclic groups to which is fused an aryl group, for example indane, and the like.

The term "substituted cycloalkyl" refers to cycloalkyl groups having 1, 2, 3, 4 or 5 substituents, and preferably 1, 2, or 3 substituents, selected from the group consisting of alkyl, alkenyl, alkynyl, alkoxy, cycloalkyl, cycloalkenyl, acyl, acylamino, acyloxy, amino, aminocarbonyl, alkoxycarbonylamino, azido, cyano, halogen, hydroxy, keto, thiocarbonyl, carboxyl, carboxyalkyl, arylthio, heteroarylthio, heterocyclylthio, thiol, alkylthio, aryl, aryloxy, heteroaryl, aminosulfonyl, aminocarbonylamino, heteroaryloxy, heterocyclyl, heterocyclooxy, hydroxyamino, alkoxyamino, nitro, —SO-alkyl, —SO-aryl, —SO-heteroaryl, —SO$_2$-alkyl, SO$_2$-aryl and —SO$_2$-heteroaryl. Unless otherwise constrained by the definition, all substituents may optionally be further substituted by 1, 2, or 3 substituents chosen from alkyl, carboxyl, carboxyalkyl, aminocarbonyl, hydroxy, alkoxy, halogen, CF$_3$, amino, substituted amino, cyano, and —S(O)$_n$R, where R is alkyl, aryl, or heteroaryl and n is 0, 1 or 2.

The term "halogen" or "halo" refers to fluoro, bromo, chloro, and iodo.

The term "acyl" denotes a group —C(O)R, in which R is hydrogen, optionally substituted alkyl, optionally substituted cycloalkyl, optionally substituted heterocyclyl, optionally substituted aryl, and optionally substituted heteroaryl.

The term "heteroaryl" refers to a radical derived from an aromatic cyclic group (i.e., fully unsaturated) having 1, 2, 3, 4, 5, 6, 7, 8, 9, 10, 11, 12, 13, 14, or 15 carbon atoms and 1, 2, 3 or 4 heteroatoms selected from oxygen, nitrogen and sulfur within at least one ring. Such heteroaryl groups can have a single ring (e.g., pyridyl or furyl) or multiple condensed rings (e.g., indolizinyl, benzothiazolyl, or benzothienyl). Examples of heteroaryls include, but are not limited to, [1,2,4]oxadiazole, [1,3,4]oxadiazole, [1,2,4]thiadiazole, [1,3,4]thiadiazole, pyrrole, imidazole, pyrazole, pyridine, pyrazine, pyrimidine, pyridazine, indolizine, isoindole, indole, indazole, purine, quinolizine, isoquinoline, quinoline, phthalazine, naphthylpyridine, quinoxaline, quinazoline, cinnoline, pteridine, carbazole, carboline, phenanthridine, acridine, phenanthroline, thiazole, isothiazole, phenazine, oxazole, isoxazole, phenoxazine, phenothiazine, imidazolidine, imidazoline, and the like as well as N-oxide and N-alkoxy derivatives of nitrogen containing heteroaryl compounds, for example pyridine-N-oxide derivatives.

Unless otherwise constrained by the definition for the heteroaryl or heteroarylene substituent, such heteroaryl or heteroarylene groups can be optionally substituted with 1 to 5 substituents, preferably 1 to 3 substituents selected from the group consisting of alkyl, alkenyl, alkynyl, alkoxy, cycloalkyl, cycloalkenyl, acyl, acylamino, acyloxy, amino, aminocarbonyl, alkoxycarbonylamino, azido, cyano, halogen, hydroxy, keto, thiocarbonyl, carboxyl, carboxyalkyl, arylthio, heteroarylthio, heterocyclylthio, thiol, alkylthio, aryl, aryloxy, heteroaryl, aminosulfonyl, aminocarbonylamino, heteroaryloxy, heterocyclyl, heterocyclooxy, hydroxyamino, alkoxyamino, nitro, —SO-alkyl, —SO-aryl, —SO-heteroaryl, —SO$_2$-alkyl, SO$_2$-aryl and —SO$_2$-heteroaryl. Unless otherwise constrained by the definition, all substituents may optionally be further substituted by 1-3 substituents chosen from alkyl, carboxyl, carboxyalkyl, aminocarbonyl, hydroxy, alkoxy, halogen, CF$_3$, amino, substituted amino, cyano, and —S(O)$_n$R, where R is alkyl, aryl, or heteroaryl and n is 0, 1 or 2.

The term "heteroaralkyl" refers to a heteroaryl group covalently linked to an alkylene group, where heteroaryl and alkylene are defined herein. "Optionally substituted heteroaralkyl" refers to an optionally substituted heteroaryl group covalently linked to an optionally substituted alkylene group. Such heteroaralkyl groups are exemplified by 3-pyridylmethyl, quinolin-8-ylethyl, 4-methoxythiazol-2-ylpropyl, and the like.

The term "heteroaryloxy" refers to the group heteroaryl-O—.

The term "heterocyclyl" refers to a monoradical saturated or partially unsaturated group having a single ring or multiple condensed rings, having from 1 to 40 carbon atoms and from 1 to 10 hetero atoms, preferably 1, 2, 3 or 4 heteroatoms, selected from nitrogen, sulfur, phosphorus, and/or oxygen within the ring. Heterocyclic groups can have a single ring or multiple condensed rings, and include tetrahydrofuranyl, morpholino, oxathiane, thiomorpholino, tetraydropthiophenyl, tetrahydropyranyl, tetrahydrothiopyranyl, piperidinyl, triazolidino, piperazinyl, dihydropyridino, pyrrolidinyl, imidazolidino, hexahydropyrimidine, hezahydropyridazine, imidazoline, and the like.

Unless otherwise constrained by the definition for the heterocyclic substituent, such heterocyclic groups can be optionally substituted with 1, 2, 3, 4 or 5, and preferably 1, 2 or 3 substituents, selected from the group consisting of alkyl, alkenyl, alkynyl, alkoxy, cycloalkyl, cycloalkenyl, acyl, acylamino, acyloxy, amino, aminocarbonyl, alkoxycarbonylamino, azido, cyano, halogen, hydroxy, keto, thiocarbonyl, carboxyl, carboxyalkyl, arylthio, heteroarylthio, heterocyclylthio, thiol, alkylthio, aryl, aryloxy, heteroaryl, aminosulfonyl, aminocarbonylamino, heteroaryloxy, heterocyclyl, heterocyclooxy, hydroxyamino, alkoxyamino, nitro, —SO-alkyl, —SO-aryl, —SO-heteroaryl, —SO$_2$-alkyl, SO$_2$-aryl and —SO$_2$-heteroaryl. Unless otherwise constrained by the definition, all substituents may optionally be further substituted by 1-3 substituents chosen from alkyl, carboxyl, carboxyalkyl, aminocarbonyl, hydroxy, alkoxy, halogen, CF$_3$, amino, substituted amino, cyano, and —S(O)$_n$R, where R is alkyl, aryl, or heteroaryl and n is 0, 1 or 2.

The term "thiol" refers to the group —SH.

The term "substituted alkylthio" refers to the group —S-substituted alkyl.

The term "heteroarylthiol" refers to the group —S-heteroaryl wherein the heteroaryl group is as defined above including optionally substituted heteroaryl groups as also defined above.

The term "sulfoxide" refers to a group —S(O)R, in which R is alkyl, aryl, or heteroaryl. "Substituted sulfoxide" refers to a group —S(O)R, in which R is substituted alkyl, substituted aryl, or substituted heteroaryl, as defined herein.

The term "sulfone" refers to a group —S(O)$_2$R, in which R is alkyl, aryl, or heteroaryl. "Substituted sulfone" refers to a group —S(O)$_2$R, in which R is substituted alkyl, substituted aryl, or substituted heteroaryl, as defined herein.

The term "keto" refers to a group —C(O)—.

The term "thiocarbonyl" refers to a group —C(S)—.

The term "carboxyl" refers to a group —C(O)—OH.

"Optional" or "optionally" means that the subsequently described event or circumstance may or may not occur, and that the description includes instances where said event or circumstance occurs and instances in which it does not.

The term "compound of Formula I" is intended to encompass the compounds of the invention as disclosed, and the pharmaceutically acceptable salts, pharmaceutically acceptable esters, prodrugs, hydrates and polymorphs of such compounds. Additionally, the compounds of the invention may possess one or more asymmetric centers, and can be produced as a racemic mixture or as individual enantiomers or diastereoisomers. The number of stereoisomers present in any given compound of Formula I depends upon the number of asymmetric centers present (there are $2^n$ stereoisomers possible where n is the number of asymmetric centers). The individual stereoisomers may be obtained by resolving a racemic or non-racemic mixture of an intermediate at some appropriate stage of the synthesis, or by resolution of the compound of Formula I by conventional means. The individual stereoisomers (including individual enantiomers and diastereoisomers) as well as racemic and non-racemic mixtures of stereoisomers are encompassed within the scope of the present invention, all of which are intended to be depicted by the structures of this specification unless otherwise specifically indicated.

"Isomers" are different compounds that have the same molecular formula.

"Stereoisomers" are isomers that differ only in the way the atoms are arranged in space.

"Enantiomers" are a pair of stereoisomers that are non-superimposable mirror images of each other. A 1:1 mixture of a pair of enantiomers is a "racemic" mixture. The term "(±)" is used to designate a racemic mixture where appropriate.

"Diastereoisomers" are stereoisomers that have at least two asymmetric atoms, but which are not mirror-images of each other.

The absolute stereochemistry is specified according to the Cahn-Ingold-Prelog R-S system. When the compound is a pure enantiomer the stereochemistry at each chiral carbon may be specified by either R or S. Resolved compounds whose absolute configuration is unknown are designated (+) or (−) depending on the direction (dextro- or levorotary) which they rotate the plane of polarized light at the wavelength of the sodium D line.

"Parenteral administration" is the systemic delivery of the therapeutic agent via injection to the patient.

The term "therapeutically effective amount" refers to that amount of a compound of Formula I that is sufficient to effect treatment, as defined below, when administered to a mammal in need of such treatment. The therapeutically effective amount will vary depending upon the specific activity of the therapeutic agent being used, and the age, physical condition, existence of other disease states, and nutritional status of the patient. Additionally, other medication the patient may be receiving will effect the determination of the therapeutically effective amount of the therapeutic agent to administer.

The term "treatment" or "treating" means any treatment of a disease in a mammal, including:
  (i) preventing the disease, that is, causing the clinical symptoms of the disease not to develop;
  (ii) inhibiting the disease, that is, arresting the development of clinical symptoms; and/or
  (iii) relieving the disease, that is, causing the regression of clinical symptoms.

In many cases, the compounds of this invention are capable of forming acid and/or base salts by virtue of the presence of amino and/or carboxyl groups or groups similar thereto. The term "pharmaceutically acceptable salt" refers to salts that retain the biological effectiveness and properties of the compounds of Formula I, and which are not biologically or otherwise undesirable. Pharmaceutically acceptable base addition salts can be prepared from inorganic and organic bases. Salts derived from inorganic bases, include by way of example only, sodium, potassium, lithium, ammonium, calcium and magnesium salts. Salts derived from organic bases include, but are not limited to, salts of primary, secondary and tertiary amines, such as alkyl amines, dialkyl amines, trialkyl amines, substituted alkyl amines, di(substituted alkyl) amines, tri(substituted alkyl)amines, alkenyl amines, dialkenyl amines, trialkenyl amines, substituted alkenyl amines, di(substituted alkenyl)amines, tri(substituted alkenyl) amines, cycloalkyl amines, di(cycloalkyl)amines, tri(cycloalkyl)amines, substituted cycloalkyl amines, disubstituted cycloalkyl amine, trisubstituted cycloalkyl amines, cycloalkenyl amines, di(cycloalkenyl)amines, tri(cycloalkenyl) amines, substituted cycloalkenyl amines, disubstituted cycloalkenyl amine, trisubstituted cycloalkenyl amines, aryl amines, diaryl amines, triaryl amines, heteroaryl amines, diheteroaryl amines, triheteroaryl amines, heterocyclic amines, diheterocyclic amines, triheterocyclic amines, mixed di- and tri-amines where at least two of the substituents on the amine are different and are selected from the group consisting of alkyl, substituted alkyl, alkenyl, substituted alkenyl, cycloalkyl, substituted cycloalkyl, cycloalkenyl, substituted cycloalkenyl, aryl, heteroaryl, heterocyclic, and the like. Also included are amines where the two or three substituents, together with the amino nitrogen, form a heterocyclic or heteroaryl group.

Specific examples of suitable amines include, by way of example only, isopropylamine, trimethyl amine, diethyl amine, tri(iso-propyl)amine, tri(n-propyl)amine, ethanolamine, 2-dimethylaminoethanol, tromethamine, lysine, arginine, histidine, caffeine, procaine, hydrabamine, choline, betaine, ethylenediamine, glucosamine, N-alkylglucamines, theobromine, purines, piperazine, piperidine, morpholine, N-ethylpiperidine, and the like.

Pharmaceutically acceptable acid addition salts may be prepared from inorganic and organic acids. Salts derived from inorganic acids include hydrochloric acid, hydrobromic acid, sulfuric acid, nitric acid, phosphoric acid, and the like. Salts derived from organic acids include acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluene-sulfonic acid, salicylic acid, and the like.

As used herein, "pharmaceutically acceptable carrier" includes any and all solvents, dispersion media, coatings, antibacterial and antifungal agents, isotonic and absorption delaying agents and the like. The use of such media and agents for pharmaceutically active substances is well known in the art. Except insofar as any conventional media or agent is incompatible with the active ingredient, its use in the therapeutic compositions is contemplated. Supplementary active ingredients can also be incorporated into the compositions.

Nomenclature

The naming and numbering of the compounds of the invention is illustrated with a representative compound of Formula I in which $R^1$ is 5-[3-fluoro-5-(trifluoromethyl)phenyl]-(1,2,4-oxadiazol-3-yl) and $R^2$ is hydroxyl:

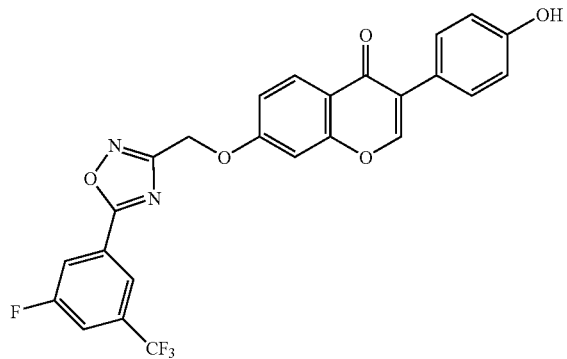

is named 7-({5-[3-fluoro-5-(trifluoromethyl)phenyl](1,2,4-oxadiazol-3-yl)}methoxy)-3-(4-hydroxyphenyl)chromen-4-one.

Synthetic Reaction Parameters

The terms "solvent", "inert organic solvent" or "inert solvent" mean a solvent inert under the conditions of the reaction being described in conjunction therewith [including, for example, benzene, toluene, acetonitrile, tetrahydrofuran ("THF"), dimethylformamide ("DMF"), chloroform, methylene chloride (or dichloromethane), diethyl ether, methanol, pyridine and the like]. Unless specified to the contrary, the solvents used in the reactions of the present invention are inert organic solvents.

The term "q.s." means adding a quantity sufficient to achieve a stated function, e.g., to bring a solution to the desired volume (i.e., 100%).

Synthesis of the Compounds of Formula I

The compounds of Formula I in which $R^2$ is hydroxy and X, Y and Z are all —$CR^6$—, in which $R^6$ is hydrogen may be prepared as shown in Reaction Scheme I.

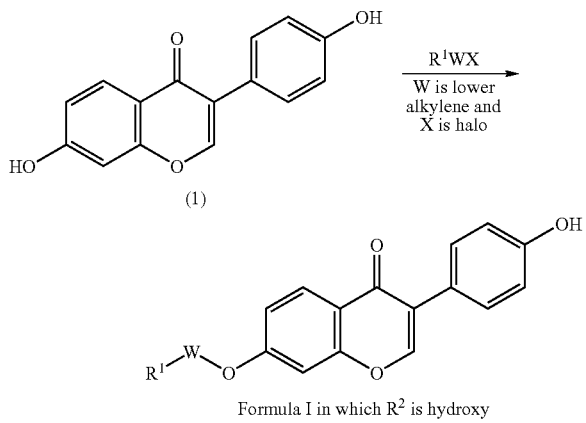

Formula I in which $R^2$ is hydroxy

In general, the compound of formula (1), (daidzein, commercially available) is dissolved in an inert solvent, for example N,N-dimethylformamide, and reacted with about an equimolar amount of a compound of formula R¹WX, where W is lower alkylene of 1-3 carbon atoms and X is iodo, bromo or chloro, in the presence of a base, for example potassium carbonate, potassium hydroxide, cesium carbonate, or the like. The reaction may be conducted at a temperature of about 50-100° C., for about 1-10 hours or may also be conducted at room temperature for 3 to 24 hours. When the reaction is substantially complete, the product of Formula I in which $R^2$ is hydroxy is isolated by conventional means, for example by precipitating the product out of solution by addition of water.

Alternatively, the compound of formula (1) is dissolved in an inert solvent, for example acetone, and an aqueous base added, for example 2N potassium hydroxide, and the mixture sonicated for about 5-30 minutes. The mixture is then reacted with about an equimolar amount of a compound of formula R¹WX, where W is lower alkylene of 1-3 carbon atoms and X is iodo, bromo or chloro, in the presence of about an equimolar amount of potassium iodide, and the mixture reacted at about reflux temperature for about 1-5 days. When the reaction is substantially complete, the product of Formula I in which $R^2$ is hydroxy is isolated by conventional means, for example by chromatography.

A method for preparing compounds of Formula I in which $R^1$ is phenyl substituted by tetrazol-5-yl, W is methylene, and X, Y and Z are all —$CR^6$—, in which $R^6$ is hydrogen is shown in Reaction Scheme II.

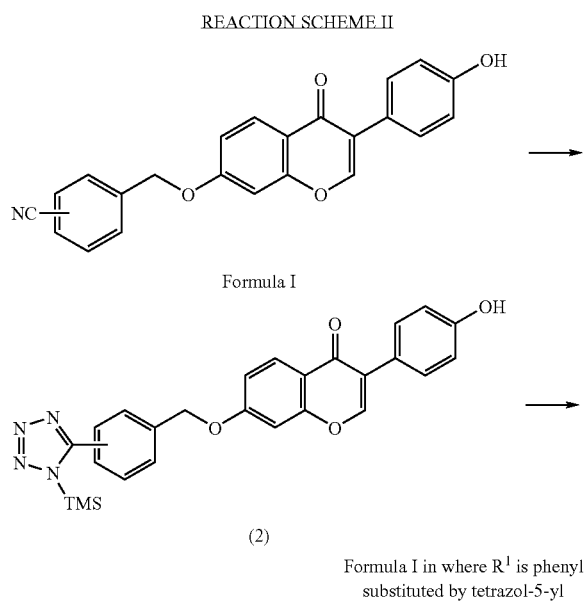

REACTION SCHEME II

Formula I (2)

Formula I in where $R^1$ is phenyl substituted by tetrazol-5-yl

Step 1—Preparation of a Compound of Formula (2)

In general, a mixture of the compound of Formula I in which $R^1$ is benzonitrile, dibutyltin oxide, and azidotrimethylsilane is subjected to microwaves. The reaction is conducted at a temperature of about 150° C. for about 10-30 minutes. When the reaction is substantially complete, the product of formula (2) is isolated by conventional means, for example by chromatography on silica gel.

Step 2—Preparation of a Compound of Formula I

The purified product of formula (2) is suspended in an aqueous solvent, for example acetonitrile/water, and a catalytic amount of a strong acid added, for example trifluoroacetic acid. Removal of the solvents provides the compound of Formula I in which $R^1$ is phenyl substituted by tetrazol-5-yl.

Similarly, the compound of Formula I in which $R^1$ is [1,2,4]-oxadiazol-3-yl substituted by benzonitrile at the 5-position is converted to a compound of Formula I in which $R^1$ is [1,2,4]-oxadiazol-3-yl substituted by tetrazol-5-ylphenyl.

Compounds of Formula I in which $R^2$ is —$NHR^5$ in which $R^5$ is hydrogen may be prepared from an intermediate having a nitro group precursor, as shown in Reaction Scheme III.

REACTION SCHEME III

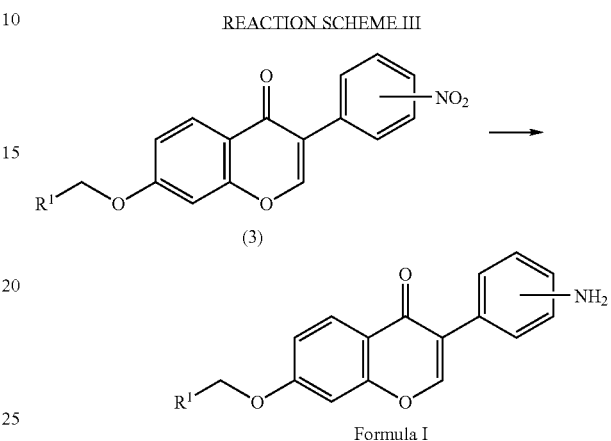

(3)

Formula I

Step 1—Preparation of a Compound of Formula I

In general, a nitro derivative of formula (3) (prepared as described in Reaction Scheme I but using a commercially available nitro daidzein derivative as the starting material) is suspended in an aqueous solvent, for example a mixture of tetrahydrofuran and water, and reacted with sodium dithionite. The reaction is conducted at a temperature of about 50-70° C. overnight. When the reaction is substantially complete, the amine of Formula I is isolated by conventional means, for example by chromatography on silica gel.

Alternatively, the compound of formula (3) can be suspended in acetic acid followed by the slow addition of zinc over 20 to 40 minutes. As this reaction will be exothermic, the suspension is cooled in an ice-water bath. Once all the zinc has been added the reaction is allowed to warm to room temperature under continued stirring. After the reaction is complete, the amine of Formula I is isolated by conventional means, for example by filtration with Celite to remove side products, followed by washing with ETOAc, drying with $Na_2SO_4$, filtering, and solvent removal.

It should be noted that if the compound of formula (3) has a carboxyl group present on the $R^1$ moiety, the carboxyl group may be protected as an allyl or alkyl, i.e., tert-butyl ester before carrying out the reduction of the nitro group. It will be understood that the protecting group may be placed on the carboxyl group before of the R¹W group to the Formula I core using, a Pro-R¹WX compound as a reactant, or after attachment, for example by reacting the acidic compound of Formula I, with 2-methylpropan-2-ol, $MgSO_4$, and $H_2SO_4$ in dichloromethane. Such a protecting group protects the carboxyl group in any subsequent reaction in which the amine is, for example acylated, and is easily removed after acylation via conventional hydrolysis conditions.

Conversion of a compound of Formula I in which W is methylene, X, Y and Z are all —$CR^6$—, in which $R^6$ is hydrogen, and $R^2$ is $NH_2$ to a corresponding compound of Formula I in which $R^2$ is $NHSO_2R^5$ is shown in Reaction Scheme IV.

REACTION SCHEME IV

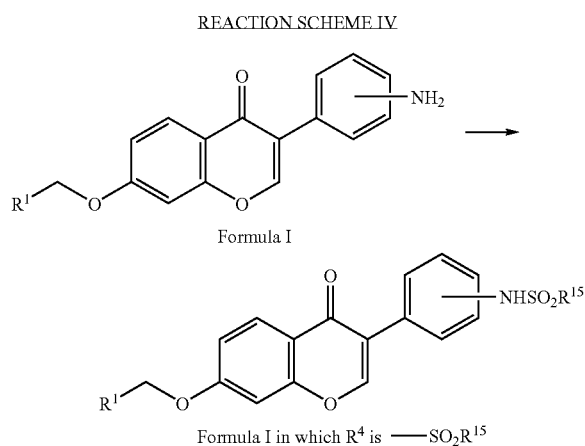

Formula I

Formula I in which R⁴ is —SO₂R¹⁵

In general, the compound of Formula I in which $R^2$ is amino is suspended in an inert solvent, for example dichloromethane, and a tertiary base added, for example pyridine. The mixture is cooled to about 0° C., a compound of formula $R^{15}SO_2Cl$ added, and the mixture reacted for about 1-2 hours. When the reaction is substantially complete, the compound of Formula I in which $R^4$ is —$SO_2R^{15}$ is isolated by conventional means, for example by chromatography on silica gel.

Similarly, reaction of a compound of Formula I in which $R^2$ is amino with an acylating agent of formula $ClC(O)R^5$ provides compounds of Formula I in which $R^2$ is —$NHR^4$ where $R^4$ is —$C(O)R^5$. Reaction with a compound of formula ClC(O)NHR⁵ or R⁵NCO provides compounds of Formula I in which $R^4$ is —$C(O)NHR^5$.

When a carboxyl group present on the $R^1$ moiety has been protected as an allyl or alkyl ester before carrying out the reduction of the nitro group, conversion of a compound of Formula I in which W is methylene, X, Y and Z are all —$CR^6$—, in which $R^6$ is hydrogen, and $R^1$ is an allyl ester derivative to a corresponding compound of Formula I in which $R^1$ is an acid derivative is shown in Reaction Scheme V.

REACTION SCHEME V

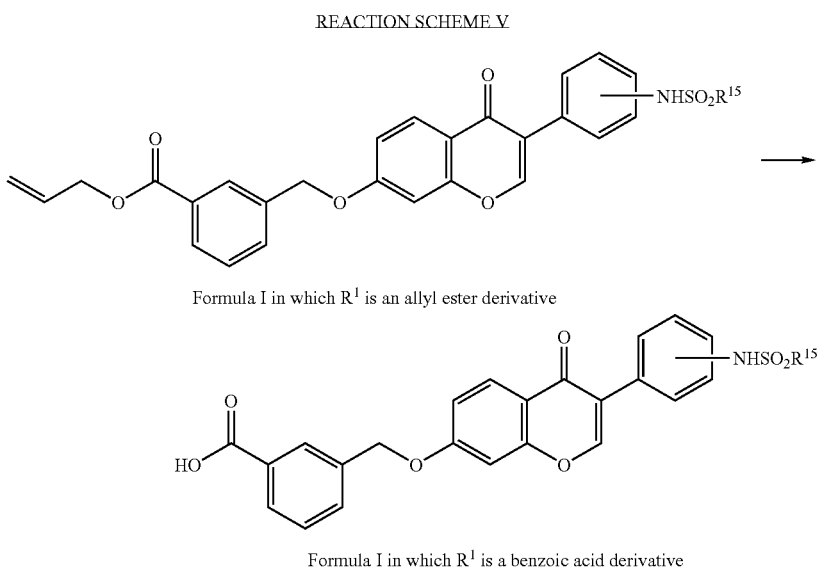

Formula I in which R¹ is an allyl ester derivative

Formula I in which R¹ is a benzoic acid derivative

In general, when the $R^1$ moiety has been protected as an allyl ester the derivative of Formula I is dissolved in an inert solvent, for example tetrahydrofuran, and a base, for example morpholine, and tetrakis(triphenyl-phosphine)palladium(0) added. The reaction is conducted at about room temperature for about 1-12 hours. When the reaction is substantially complete, the compound of Formula I in which $R^1$ is a benzoic acid derivative is isolated by conventional means, for example by flash chromatography on silica gel. When $R^1$ moiety has been protected as an alkyl i.e., tert butyl, ester, the derivative of Formula I is suspended in $HCO_2H$ and heated at 50° C. for 1 hour followed by gradually increased heat to 80° C. taking for approximately 2 to 3 hours. Once the reaction is complete, the suspension is allowed to cool to ambient temperature and stirred for an additional 7 to 10 hours. After stirring, water is added and the reaction mixture stirred at least for 1 h under ice-water bath cooling. The resulting precipitate is collected by filtration and the residue repeatedly washed with water. After drying, crude product is collected and may be purified by recrystallization in DMF with methanol.

If desired, additional modification of the $R^1$ carboxylic group can be carried out by reaction of the compound with an alcohol of the desired moiety as shown in Reaction Scheme VI.

REACTION SCHEME VI

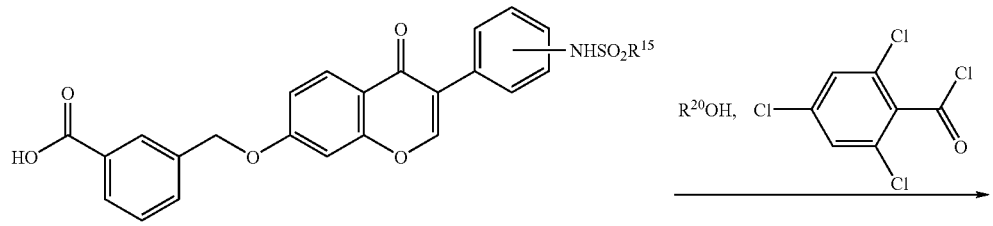

Formula I in which R¹ is a benzoic acid derivative

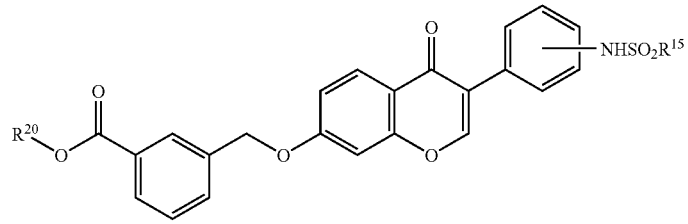

Formula I in which R¹ is an ether derivative

The acidic compound of Formula I is first dissolved in an appropriate solvent such as THF or DMF along with a base such as triethylamine and 2,4,6-trichlorobenzoyl chloride. This solution is allowed to react at room temperature for approximately 1 hour under a nitrogen atmosphere. Once this stage of the synthesis is complete, a solution of the $R^{20}OH$ reactant and dimethylaminopyridine in solvent is added and the combined mixture stirred at room temperature for an additional hour. After the addition of water, the modified compound of Formula I can be collected from the separated organic phase using conventional methods.

The compounds of formula $R^1WLG$ are either commercially available, or are made by methods well known in the art. For example, to prepare compounds of Formula I in which $R^1$ is oxazole substituted with optionally substituted phenyl, the synthesis starts from a compound of formula (4) (which is a compound of formula $R^1WLG$ in which $R^1$ is optionally substituted 1,3-oxazole, W is methylene), and LG is Cl, the preparation of which is shown in Reaction Scheme VII.

REACTION SCHEME VII

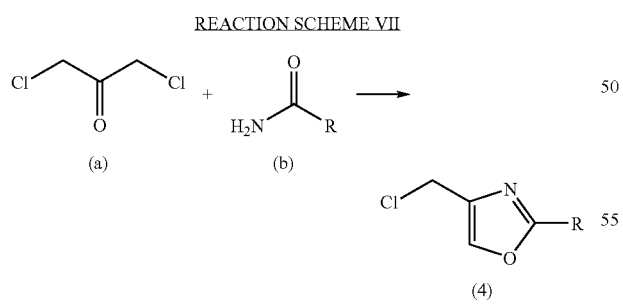

where R is optionally substituted phenyl.

In general, 1,3-dichloroacetone (a) is reacted with an appropriately substituted benzamide derivative of formula (b), in which R is optionally substituted phenyl. The reaction is conducted at a temperature of about 100-140° C., for about 1-6 hours. When the reaction is substantially complete, the compound of formula (4) is isolated by conventional means, for example by flash chromatography on silica gel or recrystallization from an inert solvent.

The compound of formula (4) is then reacted with a compound of formula (1), (daidzein, commercially available) as shown in Reaction Scheme I above, to provide a compound of Formula I.

Similarly, a compound of formula $R^1WLG1$ in which $R^1$ is optionally substituted 1,3,4-oxadiazole, W is methylene and LG is Cl can be prepared as shown in Reaction Scheme VII

REACTION SCHEME VIII

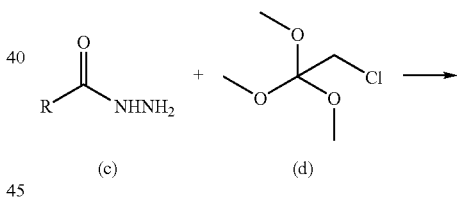

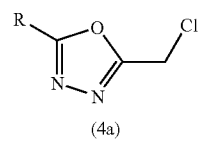

(4a)

where R is optionally substituted phenyl

The hydrazide of formula (c), which is commercially available or made by means well known in the art, is suspended in 2-chlorotrimethoxyethane (d) in the presence of an organic acid, for example acetic acid. The mixture is carried out a temperature of about 140-180° C., in a microwave oven. When the reaction is substantially complete, the compound of formula (4a) is isolated by conventional means.

Similarly, a compound of formula $R^1WLG$ in which $R^1$ is optionally substituted 1,2,4-oxadiazole, W is alkylene, and LG is Cl can be prepared as shown in Reaction Scheme IX

REACTION SCHEME IX

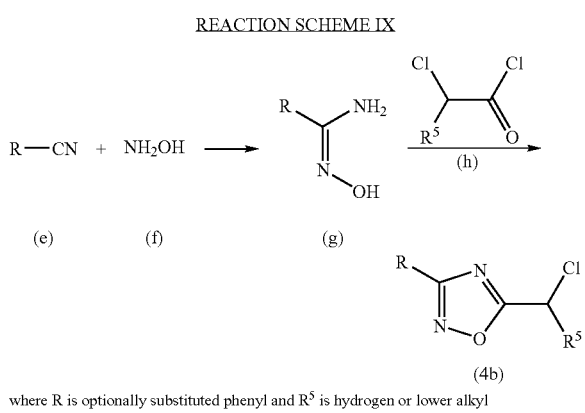

where R is optionally substituted phenyl and $R^5$ is hydrogen or lower alkyl

Step 1

In general, the nitrile of formula (e), in which R is optionally substituted phenyl, is reacted with aqueous hydroxylamine (formula (f)) in a protic solvent, for example ethanol. The reaction is conducted at a temperature of about 50-100° C., for about 2 hours. When the reaction is substantially complete, the compound of formula (g) is isolated by conventional means.

Step 2

The compound of formula (g) is then reacted with a compound of formula (h), in which $R^5$ is hydrogen or lower alkyl. The reaction is conducted at a temperature of about 50-100° C., for about 2 hours. When the reaction is substantially complete, the compound of formula (4b) is isolated by conventional means.

The compound of formula (4b) is then reacted with a compound of formula (1), (daidzein, commercially available) as shown in Reaction Scheme I above, to provide a compound of Formula I.

Alternatively, a compound of formula $R^1$ WLG in which $R^1$ is optionally substituted 1,2,4-oxadiazole, W is alkylene, and LG is Cl may also be prepared as shown in Reaction Scheme X

REACTION SCHEME X

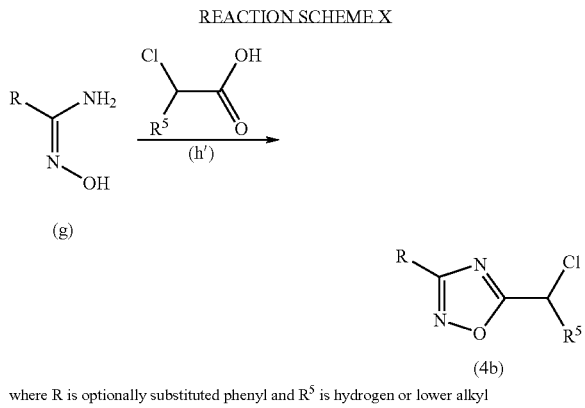

where R is optionally substituted phenyl and $R^5$ is hydrogen or lower alkyl

The compound of formula (g) is reacted with the compound of formula (h'), in which $R^5$ is hydrogen or lower alkyl. The compound of formula (h') is placed in as suitable solvent such a dichloromethane and cooled to approximately 0° C. After 20 to 40 minutes, the compound of formula (g') is added and the coupling reaction allowed to proceed fro 1 to 2 hours.

$CBr_4$ and $Ph_3P$ are then added and the dehydration allowed to proceed for an additional 4 to 6 hours. Solid triphenylphosine oxide is removed and the remaining solvent evaporated and the compound of formula (4b) is isolated by conventional means.

As before, the compound of formula (4b) is then reacted with a compound of formula (1), (daidzein, commercially available) as shown in Reaction Scheme I above, to provide a compound of Formula I.

Similarly, a compound of formula $R^1$WLG in which $R^1$ is isoxazole, W is methylene, and LG is Cl can be prepared as shown in Reaction Scheme XI

REACTION SCHEME XI

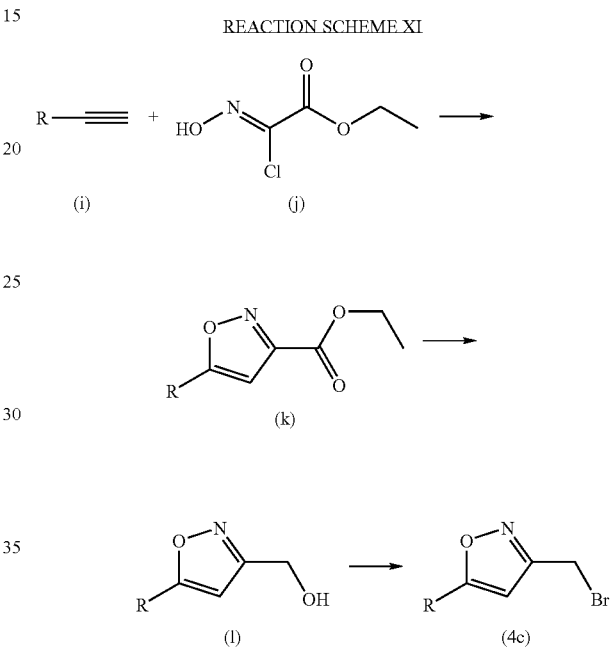

Step 1

In general, the acetylene derivative of formula (i), in which R is optionally substituted phenyl, is reacted with ethyl chlorooximidoacetate (formula (j)) in an inert solvent, for example tetrahydrofuran, in the presence of a base, for example triethylamine. The reaction is conducted at a temperature of about 0-25° C., for about 10-24 hours. When the reaction is substantially complete, the compound of formula (k) is isolated by conventional means.

Step 2

In general, the ester derivative of formula (k), in which R is optionally substituted phenyl, is reacted with a reducing agent, for example sodium borohydride in a protic solvent, for example ethanol. The reaction is initially conducted at a temperature of about 0° C., and then at room temperature for about 1-2 hours. When the reaction is substantially complete, the compound of formula (l) is isolated by conventional means.

Step 3

In general, the hydroxymethyl derivative of formula (l), in which R is optionally substituted phenyl, is reacted with a brominating agent, for example carbon tetrabromide in the presence of triphenylphosphine. The reaction is conducted at a temperature of about 0° C. for about 1-2 hours. When the reaction is substantially complete, the compound of formula (4c) is isolated by conventional means.

An alternative method of preparing compounds of Formula I is shown in Reaction Scheme XII.

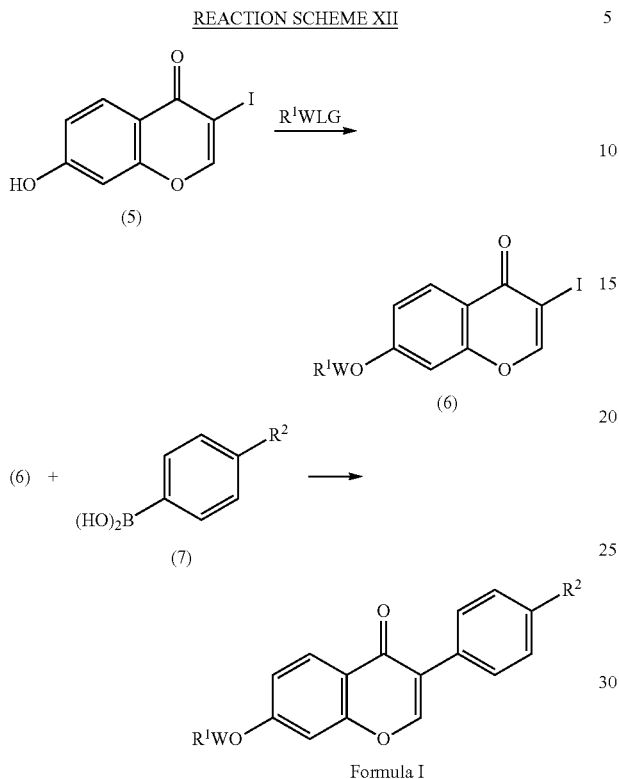

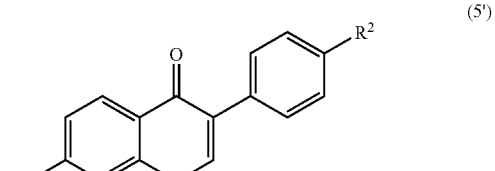

which may then be reacted with a compound of formula R¹WX as described above.

One method of preparing the starting material 3-iodo-7-methoxychromen-4-one is shown in Reaction Scheme XIII.

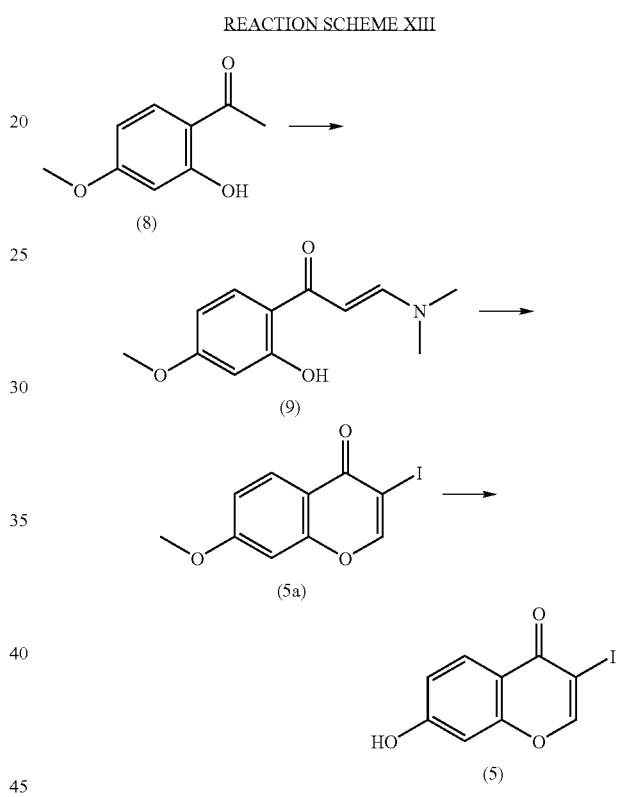

Step 1

In general, the compound of formula (5), 7-hydroxy-3-iodochromen-4-one, is reacted with a compound of formula R¹WLG, wherein LG is a leaving group such as halogen or tosylate in a polar solvent, for example N,N-dimethylformamide, in the presence of sodium iodide and a mild base, for example potassium carbonate. The reaction is conducted at a temperature of about 40-80° C., for about 1 hour or may be conducted at room temperature for a longer period, 2 to 24 hours. When the reaction is substantially complete, the compound of formula (6) is isolated by conventional means, for example by flash chromatography on silica gel or recrystallization from an inert solvent.

Step 2

The compound of formula (6) is then reacted with the boronic acid of formula (7), which are either commercially available or prepared by means well known in the art. In general, the reaction is conducted in an inert solvent, for example dimethoxymethane, in the presence of tetrakistriphenylphosphine palladium and aqueous sodium carbonate. The reaction is conducted at a temperature of about 60-100° C., for about 1 hour. When the reaction is substantially complete, the compound of Formula I is isolated by conventional means, for example by flash chromatography on silica gel or recrystallization from an inert solvent.

As will be evident to one of ordinary skill in the art, the compound of formula (7) may first be reacted with the compound of formula (5) to produce a desired compound of formula (5a) as shown below:

Step 1

In general, the compound of formula (8), 1-(2-hydroxy-4-methoxyphenyl)ethane-1-one, is reacted with the dimethylacetal of N,N-dimethylformamide. The reaction is conducted at a temperature of about 50-100° C., for about 2 hours. When the reaction is substantially complete, the compound of formula (9) is isolated by conventional means, for example by filtration of the precipitated product, 3-(dimethylamino)-1-(2-hydroxy-4-methoxyphenyl)prop-2-en-1-one.

Step 2

The compound of formula (9) is then reacted with N-iodosuccinimide in an inert solvent, for example chloroform, in the presence of silica gel. The reaction is conducted at a temperature of about 0° C., for about 1 hour. When the reaction is substantially complete, the compound of formula (5a), 3-iodo-7-methoxychromen-4-one, is isolated by conventional means, for example by filtering off the silica gel, washing the solid with chloroform, and removal of the solvent.

Step 3

The compound of formula (5a) is then reacted with boron tribromide to convert the methoxy group to a hydroxyl group.

In general, the compound of formula (5a) is dissolved in an inert solvent, for example chloroform, cooled to about −80° C., and reacted with boron tribromide for about 1 hour. The mixture is then allowed to warm to about room temperature, and stirred for about 2-5 days. When the reaction is substantially complete, the compound of formula (5), 3-iodo-7-hydroxychromen-4-one, is isolated by conventional means.

It will be appreciated by those of skill in the art that various $Q^1$ and $Q^2$ linking groups can be added to either the $R^1WX$ reactant or the compound of formula (6) prior to the final synthesis of the compound of Formula I. Such alkylation techniques are well within the skill of one of ordinary skill in the art and will be readily apparent. Similarly, methods for subsequent modification of the $R^1$, $R^2$, or $R^3$, substituent after the synthesis of a compound of Formula I will also be readily apparent to one of ordinary skill.

For example, a method of making compounds wherein $Q^1$ is methylene, T is NH, and $Q^2$ is ethylene is shown in Reaction Scheme XIX:

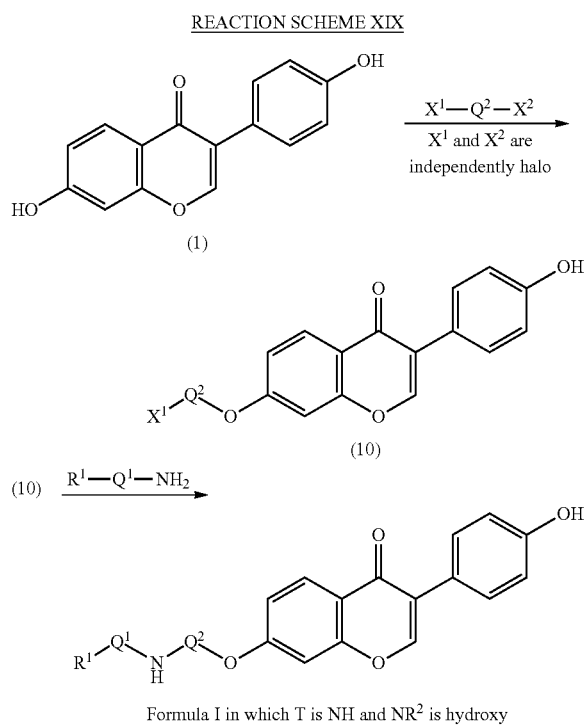

Formula I in which T is NH and $NR^2$ is hydroxy

Step 1

The commercially available compound of formula (1) is dissolved in an inert solvent, for example acetone, and an aqueous base added, for example 2N potassium hydroxide. The mixture is then reacted with about an equimolar amount of a compound of formula $X^1Q^2X^2$, where $X^1$ and $X^2$ are independently iodo, bromo or chloro. The mixture is reacted at about reflux temperature for about 1-5 days. The solvent is then evaporated and the residue purified using conventional methods such as column chromatography to provide the compound of formula (10).

Step 2

The compound of formula (10) is the reacted with a compound of formula $R^1Q^1-NH_2$ in an inert solvent such as DMF. The reaction takes place at a temperature of approximately 50° C. to 80° C. for 12 to 48 hours. When the reaction is substantially complete, the compound of Formula I is isolated by conventional means, for example by solvent evaporation followed by TLC.

As will be apparent to one of ordinary skill in the art, this type of reaction can be modified so that a modified $Q^1$ linking group is added to an appropriately halogenated $R^1$ derivative according the method described in Step 2 to provide a compound of the formula $R^1-Q^1-X$.

In another variation of the synthesis, oxirane derivatives of desired $Q^1$ and/or $Q^2$ linking groups may be used to produce compounds of Formula I wherein either or both of the Q moieties are hydroxy substituted. For example, a method of making compounds wherein $Q^1$ is methylene, T is NH, and $Q^2$ is 2-hydroxy propylene is shown in Reaction Scheme XX:

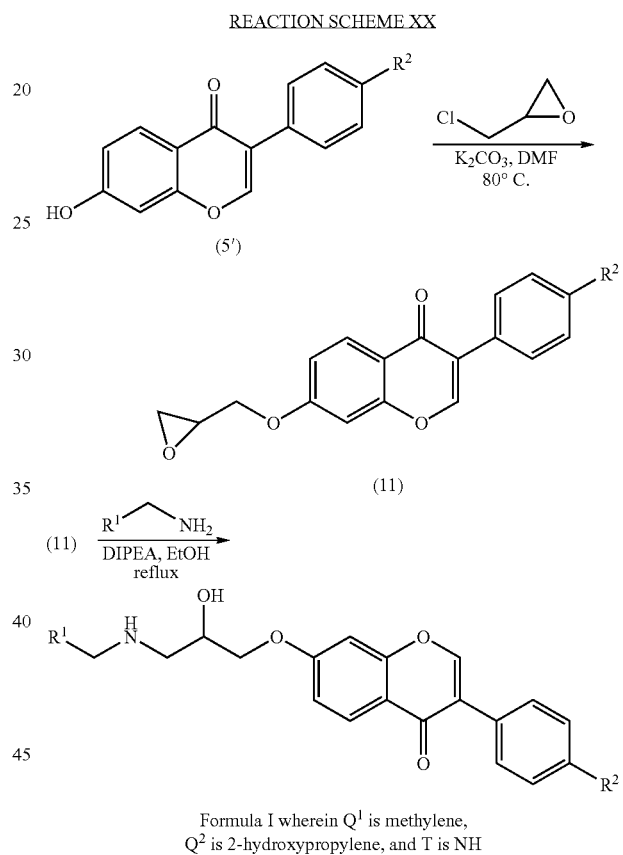

Formula I wherein $Q^1$ is methylene, $Q^2$ is 2-hydroxypropylene, and T is NH

Step 1

The compound of formula (5') is reacted with epichlorohydrin and $K_2CO_3$ in a suitable solvent such as DMF. The reaction takes place at a temperature ranging from 60° C. to 90° C. and is carried out for 1 to 6 hours. When the reaction is substantially complete, the solvent is removed by evaporation and the compound of formula (11) collected as a precipitate from the residue by treatment with $H_2O$. The precipitate may be collected conventional means, for example by flash chromatography on silica gel or recrystallization from an inert solvent.

Step 2

The compound of formula (11) is then reacted with an amino derivative of the desired $R^1Q^1$ segment, such as the $R^1$ methylamino compound shown in Reaction Scheme X. The reactants are dissolved in a protic solvent such as ethanol and a catalytic amount of base such as DIPEA (N,N'-diisopropylethylamine) is added. The reaction may be carried out by stirring overnight at a temperature of 70° C. to 85° C. When the reaction is substantially complete, the solvent is removed by evaporation and the compound of Formula I collected and purified by conventional means such as silica gel column chromatography followed by recrystallization from an inert solvent.

In instances where compounds wherein T is a covalent bond, the compound of formula (11) can be reacted with a magnesium bromide derivative of the desired $R^1Q^1$ segment. In this type of reaction, the magnesium bromide derivative is slowly added to a cooled (−60° to −30° C.) solution of CuI in THF. To this solution is then slowly added the compound of formula (11) in THF. The reaction mixture is stirred at −60° to −30° C. 1 to 2 hours then quenched with saturated $NH_4Cl$ aqueous solution and $H_2O$ and extracted with EtOAc. The organic layer is further washed with brine, then dried over $Na_2SO_4$ and evaporated in vacuo. The compound of Formula I is then collected and purified by conventional means such as prep-TLC.

Utility, Testing and Administration

General Utility

The compounds of Formula I are generally effective in the treatment of conditions that respond to administration of ALDH-2 inhibitors. Specifically, the compounds of Formula I are useful in the treatment of addictions to dopamine-producing agents of addiction such as, for example, cocaine, opiates, amphetamines, nicotine, and alcohol.

While not wishing to be bound by theory, it is believed that ALDH-2 inhibitors are effective in treating addiction as a consequence of their ability to normalize the increased dopamine levels associated with various addictive behaviors. See, N. D. Volkow et al., Dopamine in drug abuse and addiction: results from imaging studies and treatment implications, *Mol. Psychiatry.* 9 (2004), pp. 557-569; and B. J. Everitt and M. E. Wolf, Psychomotor stimulant addiction: a neural systems perspective, *J. Neurosci.* 22 (2002), pp. 3312-3320.

Given this proposed mechanism of action, it is believe that ALDH-2 inhibitors such as the compounds of Formula I will be useful in the treatment of all addictive and compulsive behaviors and neurological conditions associated with increased dopamine levels. Such behaviors and conditions include, but are not limited to, compulsive gambling, overeating, and shopping, obsessive compulsive disorder (OCD), schizophrenia, attention deficit hyperactivity disorder, and the like.

Testing

Activity testing is conducted as described in those patents and patent applications referenced above, and in the Examples below, and by methods apparent to one skilled in the art. For example, as described in "The Mitrochondrial Monoamine Oxidase-Aldehyde Dehydrogenase Pathway: A Potential Site of Action of Daidzein", J. Med. Chem. 2000, 43, 4169-4179. In general, the compounds of Formula I are assayed to determine their effects on MAO and ALDH-2 independently using the membrane and lysate of a density-gradient-purified mitochondria preparation as the respective enzyme sources. The results are expressed in IC50 values.

Pharmaceutical Compositions

The compounds of Formula I are usually administered in the form of pharmaceutical compositions. This invention therefore provides pharmaceutical compositions that contain, as the active ingredient, one or more of the compounds of Formula I, or a pharmaceutically acceptable salt or ester thereof, and one or more pharmaceutically acceptable excipients, carriers, including inert solid diluents and fillers, diluents, including sterile aqueous solution and various organic solvents, permeation enhancers, solubilizers and adjuvants. The compounds of Formula I may be administered alone or in combination with other therapeutic agents. Such compositions are prepared in a manner well known in the pharmaceutical art (see, e.g., Remington's Pharmaceutical Sciences, Mace Publishing Co., Philadelphia, Pa. $17^{th}$ Ed. (1985) and "Modern Pharmaceutics", Marcel Dekker, Inc. $3^{rd}$ Ed. (G. S. Banker & C. T. Rhodes, Eds.).

Administration

The compounds of Formula I may be administered in either single or multiple doses by any of the accepted modes of administration of agents having similar utilities, for example as described in those patents and patent applications incorporated by reference, including rectal, buccal, intranasal and transdermal routes, by intra-arterial injection, intravenously, intraperitoneally, parenterally, intramuscularly, subcutaneously, orally, topically, as an inhalant, or via an impregnated or coated device such as a stent, for example, or an artery-inserted cylindrical polymer.

One mode for administration is parental, particularly by injection. The forms in which the novel compositions of the present invention may be incorporated for administration by injection include aqueous or oil suspensions, or emulsions, with sesame oil, corn oil, cottonseed oil, or peanut oil, as well as elixirs, mannitol, dextrose, or a sterile aqueous solution, and similar pharmaceutical vehicles. Aqueous solutions in saline are also conventionally used for injection, but less preferred in the context of the present invention. Ethanol, glycerol, propylene glycol, liquid polyethylene glycol, and the like (and suitable mixtures thereof), cyclodextrin derivatives, and vegetable oils may also be employed. The proper fluidity can be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like.

Sterile injectable solutions are prepared by incorporating the compound of Formula I in the required amount in the appropriate solvent with various other ingredients as enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

Oral administration is another route for administration of the compounds of Formula I. Administration may be via capsule or enteric coated tablets, or the like. In making the pharmaceutical compositions that include at least one compound of Formula I, the active ingredient is usually diluted by an excipient and/or enclosed within such a carrier that can be in the form of a capsule, sachet, paper or other container. When the excipient serves as a diluent, in can be a solid, semi-solid, or liquid material (as above), which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, for example, up to 10% by weight of the active compound, soft and hard gelatin capsules, sterile injectable solutions, and sterile packaged powders.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, sterile water, syrup, and methyl cellulose. The formulations can additionally include: lubricating agents such as talc, magnesium stearate, and mineral oil; wetting agents; emulsifying and suspending agents; preserving agents such as methyl- and propylhydroxy-benzoates; sweetening agents; and flavoring agents.

The compositions of the invention can be formulated so as to provide quick, sustained or delayed release of the active ingredient after administration to the patient by employing procedures known in the art. Controlled release drug delivery systems for oral administration include osmotic pump systems and dissolutional systems containing polymer-coated reservoirs or drug-polymer matrix formulations. Examples of controlled release systems are given in U.S. Pat. Nos. 3,845,770; 4,326,525; 4,902,514; and 5,616,345. Another formulation for use in the methods of the present invention employs transdermal delivery devices ("patches"). Such transdermal patches may be used to provide continuous or discontinuous infusion of the compounds of the present invention in controlled amounts. The construction and use of transdermal patches for the delivery of pharmaceutical agents is well known in the art. See, e.g., U.S. Pat. Nos. 5,023,252, 4,992,445 and 5,001,139. Such patches may be constructed for continuous, pulsatile, or on demand delivery of pharmaceutical agents.

The compositions are preferably formulated in a unit dosage form. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient (e.g., a tablet, capsule, ampoule). The compounds of Formula I are effective over a wide dosage range and is generally administered in a pharmaceutically effective amount. Preferably, for oral administration, each dosage unit contains from 10 mg to 2 g of a compound of Formula I, more preferably from 10 to 700 mg, and for parenteral administration, preferably from 10 to 700 mg of a compound of Formula I, more preferably about 50-200 mg. It will be understood, however, that the amount of the compound of Formula I actually administered will be determined by a physician, in the light of the relevant circumstances, including the condition to be treated, the chosen route of administration, the actual compound administered and its relative activity, the age, weight, and response of the individual patient, the severity of the patient's symptoms, and the like.

For preparing solid compositions such as tablets, the principal active ingredient is mixed with a pharmaceutical excipient to form a solid preformulation composition containing a homogeneous mixture of a compound of the present invention. When referring to these preformulation compositions as homogeneous, it is meant that the active ingredient is dispersed evenly throughout the composition so that the composition may be readily subdivided into equally effective unit dosage forms such as tablets, pills and capsules.

The tablets or pills of the present invention may be coated or otherwise compounded to provide a dosage form affording the advantage of prolonged action, or to protect from the acid conditions of the stomach. For example, the tablet or pill can comprise an inner dosage and an outer dosage component, the latter being in the form of an envelope over the former. The two components can be separated by an enteric layer that serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as described supra. Preferably the compositions are administered by the oral or nasal respiratory route for local or systemic effect. Compositions in preferably pharmaceutically acceptable solvents may be nebulized by use of inert gases. Nebulized solutions may be inhaled directly from the nebulizing device or the nebulizing device may be attached to a face mask tent, or intermittent positive pressure breathing machine. Solution, suspension, or powder compositions may be administered, preferably orally or nasally, from devices that deliver the formulation in an appropriate manner.

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

EXAMPLE 1

Preparation of a Compound of Formula $R^1WX$

A. Preparation of a Compound of Formula (4) in which R is Phenyl

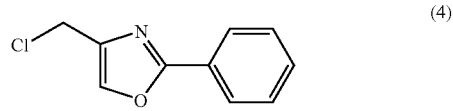

(4)

A 50 mL round bottomed flask equipped with a condenser was charged with benzamide (a compound of formula (b), 363.4 mg, 3.0 mmol) and 1,3-dichloroacetone (457.1 mg, 3.6 mmol, 1.2 equiv.). This mixture was heated at 130° C. for 1 hour under a nitrogen atmosphere. After cooling to room temperature, the resulting mixture was purified by recrystallization from acetonitrile (6 mL). The suspension was heated under reflux reaction condition for 5 minutes and cooled down to ambient temperature. The resulting solid was filtered through a glass filter, and the crystals on the filter were washed with acetonitrile (2 mL). The desired product, 4-(chloromethyl)-2-phenyl-1,3-oxazole, was obtained as a colorless powder.

B. Preparation of Other Compounds of Formula (4) in which R is Phenyl

Similarly, following the procedures of Example 1A, substituting other compounds of formula (b) for benzamide, other compounds of formula R¹WLG were prepared. For example:

4-(chloromethyl)-2-[5-fluoro-3-(trifluoromethyl)phenyl]-1,3-oxazole;
2-(3,5-difluorophenyl)-4-(chloromethyl)-1,3-oxazole;
2-(3,4-difluorophenyl)-4-(chloromethyl)-1,3-oxazole;
4-(chloromethyl)-2-(4-fluorophenyl)-1,3-oxazole,
4-(chloromethyl)-2-(4-chlorophenyl)-1,3-oxazole;
4-(chloromethyl)-2-[3-(trifluoromethyl)phenyl]-1,3-oxazole; and
4-(chloromethyl)-2-(3,4,5-trifluorophenyl)-1,3-oxazole.

C. Preparation of a Compound of Formula (4a) in which R is 4-Fluorophenyl

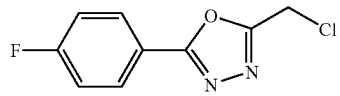

4-Fluorobenzenecarbohydrazide (0.3 g, 2 mmol) was suspended in chloro-1,1,1-trimethoxyethane (2 ml). To the suspension was added acetic acid (1 ml), and the solution was heated in a microwave for 30 minutes at 160° C. The solvent was removed under reduced pressure, and the residue purified using Biotage, eluting with 20% ethyl acetate/hexanes, to provide 5-(chloromethyl)-3-(4-fluorophenyl)-1,2,4-oxadiazole in 89% yield.

D. Preparation of a Compound of Formula (4b) in which R is 5-Fluoro-3-Trifluoromethylphenyl and R⁵ is Methyl

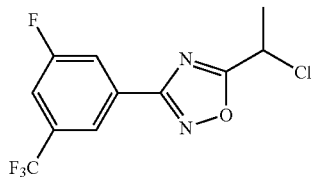

Step 1

To a solution of 5-fluoro-3-(trifluoromethyl)benzenecarbonitrile (15.0 g, 79.3 mmol) in ethanol (30 ml) was added a solution of 50% hydroxylamine in water (10 ml, 151.5 mmol), and the resulting mixture was heated at 80° C. for 2 hours. The mixture was cooled to room temperature, solvent removed under reduced pressure, and 30 ml of water added. The suspension was sonicated and the solid filtered off, washed with water (2×20 ml), and dried under reduced pressure, to provide [5-fluoro-3-(trifluoromethyl)-phenyl](hydroxyimino)methylamine as a white solid. MS 223.1 (M+H).

Step 2

To a solution of [5-fluoro-3-(trifluoromethyl)phenyl](hydroxyimino)-methylamine (8.884 g, 40 mmol) in a mixture of anhydrous dichloromethane/N,N-dimethylformamide (60/20 ml) was added 2-chloropropanoyl chloride (6.0 ml, 58.7 mmol) and diisopropylethylamine (14.0 ml, 80.3 mmol), and the mixture was stirred at room temperature for two hours. The mixture was then refluxed overnight with stirring, cooled to room temperature, and solvent removed under reduced pressure. The residue was fractionally distilled under vacuum, and the portion boiling at 95-105° C./0.8-1.0 mm Hg retained, to provide 5-(chloroethyl)-3-[5-fluoro-3-(trifluoromethyl)phenyl]-1,2,4-oxadiazole as a yellow oil, MS 295.1 (M+H).

Alternatively, the product can be purified by flash chromatography over silica gel, eluting with ethyl acetate/hexanes (1/4).

E. Preparation of a Compound of Formula (4c) in which R is 3-trifluoromethylphenyl

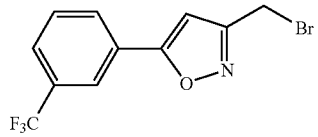

Step 1—Preparation of a Compound of Formula (k)

To a stirred solution of ethyl chlorooximidoacetate (6.68 g, 44.09 mmol) in tetrahydrofuran (90 mL) in an ice bath was added 3-(trifluoromethyl)phenylacetylene (5.0 g, 29.39 mmol) slowly, followed by triethylamine (8.19 mL, 58.78 mmol) dropwise. The resulting mixture was stirred at room temperature overnight, which was then filtered through a layer of silica gel (top) and anhydrous Na₂SO₄ (bottom), and washed with ethyl acetate. The filtrate was washed with water, the organic layer dried over sodium sulfate, and the solvent removed under reduced pressure. The residue was purified by silica gel column chromatography (ethyl acetate: Hexanes=1:9) to afford ethyl 5-[3-(trifluoromethyl)phenyl]isoxazole-3-carboxylate.

Similarly prepared was ethyl 5-(2-pyridyl)isoxazole-3-carboxylate.

Step 2—Preparation of a Compound of Formula (l)

To a stirred solution of ethyl 5-[3-(trifluoromethyl)phenyl]isoxazole-3-carboxylate (2 g, 7 mmol) in ethanol (70 mL) in an ice bath was added sodium borohydride (1.06 g, 28 mmol) portionwise. The resulting mixture was stirred at room temperature for 1.5 hours, which was then quenched with saturated ammonium chloride aqueous solution. Solvent was removed from the mixture under reduced pressure, and the residue was dissolved in ethyl acetate and washed with water. The organic layer was then dried over sodium sulfate, and solvent removed under reduced pressure. The residue was purified by silica gel column chromatography (ethyl acetate: Hexanes=2:3) to afford {5-[3-(trifluoromethyl)phenyl]isoxazol-3-yl}methane-1-ol.

Similarly prepared was (5-(2-pyridyl)isoxazol-3-yl)methane-1-ol.

Step 3—Preparation of a Compound of Formula (4c)

To a stirred suspension of {5-[3-(trifluoromethyl)phenyl]isoxazol-3-yl}methane-1-ol (0.28 g, 1.15 mmol) and carbon tetrabromide (0.5 g, 1.5 mmol) in methylene chloride (10 mL) at 0° C. was added dropwise a solution of triphenylphosphine (0.41 g, 1.58 mmol) in methylene chloride (5 mL). The resulting mixture was stirred at 0° C. for 1 hour, then the reaction mixture poured into ethyl acetate and Hexanes (ethyl acetate: Hexanes=1:4, 50 mL). The resulting suspension was filtered through a thin layer of silica gel and washed with ethyl acetate and Hexanes (ethyl acetate:Hexanes=1:4). The filtrate was concentrated under reduced pressure, and the residue was purified by silica gel column chromatography (ethyl acetate: Hexanes=1:4) to afford 3-(bromomethyl)-5-[3-(trifluoromethyl)phenyl]isoxazole.

Similarly prepared was 3-(chloromethyl)-5-(2-pyridyl)isoxazole

EXAMPLE 2

Preparation of a Compound of Formula (5)

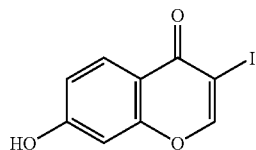

Step 1—Preparation of a Compound of Formula (9)

A mixture of 1-(2-hydroxy-4-methoxyphenyl)ethane-1-one (20 g, 120 mmol) and N,N-dimethylformamide dimethylacetal (23 g, 181 mmol) was stirred at 90° C. for 2 hours. After cooling to room temperature the reaction mixture provided a yellow precipitate, which was washed with ethyl acetate (3×30 ml), water (2×50 ml), and dried under reduced pressure to yield 3-(dimethylamino)-1-(2-hydroxy-4-methoxyphenyl)prop-2-en-1-one (9) as the trans isomer; MS 222.1 (M+H)

Step 2—Preparation of a Compound of Formula (5)

To a solution of 3-(dimethylamino)-1-(2-hydroxy-4-methoxyphenyl)prop-2-en-1-one (20.0 g, 90.37 mmol) in anhydrous chloroform (100 ml) at 0° C. was added N-iodosuccinimide (23.5 g, 99.22 mmol) and silica gel (40 g). The reaction mixture was stirred at 0° C. for 60 minutes, then the insoluble material filtered off. The filtrate was washed with aqueous sodium thiosulfate (0.5M, 2×50 ml), followed by brine (100 ml), then dried over sodium sulfate. The solvent was removed under reduced pressure, providing an orange solid. To this solid was added methanol (30 ml), and the mixture was sonicated, filtered, the solid washed with methanol (2×5 ml), and the solid dried under reduced pressure, to give 3-iodo-7-methoxychromen-4-one as a pale yellow solid.

This product (9.36 g, 30.98 mmol) was dissolved in anhydrous chloroform (10 ml), and cooled to −78° C. To this solution was added a 1.0 M solution of boron tribromide in methylene chloride (90 ml, 90 mmol), and the mixture stirred for 1 hour at −78° C. The mixture was allowed to warm to room temperature, and stirred for 4 days. The mixture was then poured into water (200 ml), and the brown solid filtered off, washed with water (4×100 ml), and chloroform (3×20 ml). The filtrate was concentrated under reduced pressure to give a yellow gel, to which was added methylene chloride (20 ml), and the mixture sonicated. A pale yellow solid was obtained, and was filtered off, washed with methylene chloride (2×5 ml), and dried under reduced pressure to provide 7-hydroxy-3-iodochromen-4-one.

EXAMPLE 3

Preparation of a Compound of Formula I

Step 1. Preparation of a Compound of Formula (6) in which $R^1$ is 4-Methyl-2-[4-(trifluoromethyl)phenyl](1,3-thiazol-5-yl), and W is Methylene

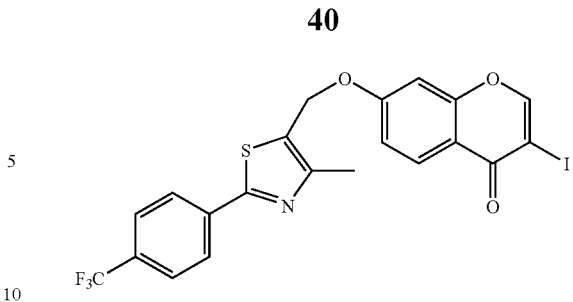

A mixture of 7-hydroxy-3-iodochromen-4-one (864 mg, 3.0 mmol), 5-(chloromethyl)-4-methyl-2-(4-(trifluoromethyl)phenyl)thiazole) (875 mg, 3.0 mmol), sodium iodide (450 mg, 3.0 mmol), and potassium carbonate (552 mg, 4.0 mmol) was dissolved in N,N-dimethylformamide (10 ml) at room temperature under nitrogen. The mixture was heated at 600 for 1 hour, cooled to room temperature, and water (30 ml) added to the mixture. The aqueous mixture was extracted with methylene chloride (3×30 ml), and the combined organic layer washed with brine (30 ml), dried over sodium sulfate, and solvent removed from the filtrate under reduced pressure. Crystallization of the crude product from ethyl acetate (4 ml) gave 3-iodo-7-({4-methyl-2-[4-(trifluoromethyl)phenyl](1,3-thiazol-5-yl)}methoxy)chromen-4-one, a compound of formula (6).

Step 2—Preparation of a Compound of Formula I in which $R^1$ is Phenyl](1,3-thiazol-5-yl), $R^2$ is 4-Methylsulfonamide, $R^3$ is Hydrogen, V is Oxygen, X, Y, and Z are —CH—, and W is Methylene

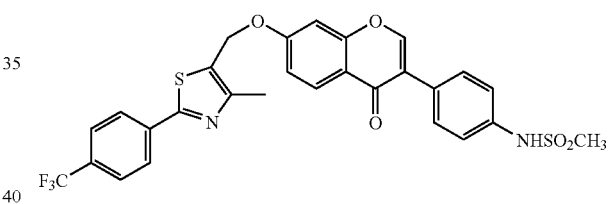

To a mixture of 3-iodo-7-({4-methyl-2-[4-(trifluoromethyl)phenyl](1,3-thiazol-5-yl)}methoxy)chromen-4-one (55.0 mg, 0.10 mmol), 4-(dihydroxyboron)-(methylsulfonyl)phenylamine (22.5 mg, 0.15 mmol), bis-(triphenylphosphine) palladium (II) dichloride (3.5 mg, 0.005 mmol) was added dimethoxyethane (2 ml) and aqueous sodium carbonate solution (2M, 0.1 ml, 2 equivs). The mixture was refluxed for 1 hour, cooled to ambient temperature, filtered through celite (3 g), and the celite washed with ethyl acetate (50 ml). The filtrate was washed with brine (30 ml), and dried over sodium sulfate. The solvent was removed under reduced pressure, and the residue chromatographed on silica gel, eluting with ethyl acetate/hexanes 50/1, after which the product was crystallized from ethyl acetate (3 ml), to provide 3-(4-[(methylsulfonyl)amino]phenyl-7-({2-[4-(trifluoromethyl)phenyl](1,3-thiazol-5-yl)}methoxy)chromen-4-one.

B.

Similarly, the following compounds of Formula I were prepared:
4-[7-({5-[3-fluoro-5-(trifluoromethyl)phenyl](1,2,4-oxadiazol-3-yl)}methoxy)-4-oxochromen-3-yl]benzenecarbonitrile;
ethyl 4-[7-({4-methyl-2-[4-(trifluoromethyl)phenyl](1,3-thiazol-5-yl)}methoxy)-4-oxochromen-3-yl]benzoate;
7-({3-[5-fluoro-3-(trifluoromethyl)phenyl](1,2,4-oxadiazol-5-yl)}ethoxy)-3-(4-hydroxyphenyl)chromen-4-one;

ethyl 3-[7-({5-[3-fluoro-5-(trifluoromethyl)phenyl](1,2,4-oxadiazol-3-yl)}methoxy)-4-oxochromen-3-yl]benzoate;
3-{4-[(methylsulfonyl)amino]phenyl}-7-({4-methyl-2-[4-(trifluoromethyl)phenyl](1,3-thiazol-5-yl)}methoxy)chromen-4-one;
methyl 4-[7-({4-methyl-2-[4-(trifluoromethyl)phenyl](1,3-thiazol-5-yl)}methoxy)-4-oxochromen-3-yl]benzoate;
3-(2H,3H-benzo[e]1,4-dioxan-6-yl)-7-({5-[3-fluoro-5-(trifluoromethyl)phenyl](1,2,4-oxadiazol-3-yl)}methoxy)chromen-4-one;
7-({5-[3-fluoro-5-(trifluoromethyl)phenyl](1,2,4-oxadiazol-3-yl)}methoxy)-3-(6-methoxy(3-pyridyl))chromen-4-one;
3-(4-hydroxyphenyl)-7-({4-methyl-2-[4-(trifluoromethyl)phenyl](1,3-thiazol-5-yl)}methoxy)chromen-4-one;
7-({5-[3-fluoro-5-(trifluoromethyl)phenyl](1,2,4-oxadiazol-3-yl)}methoxy)-3-(4-{[(4-methylphenyl)sulfonyl]amino}phenyl)chromen-4-one;
3-(4-{[(4-methylphenyl)sulfonyl]amino}phenyl)-7-({4-methyl-2-[4-(trifluoromethyl)phenyl](1,3-thiazol-5-yl)}methoxy)chromen-4-one;
methyl 3-{[3-(6-methoxy(3-pyridyl))-4-oxochromen-7-yloxy]methyl}benzoate;
methyl 3-({3-[4-(hydroxymethyl)phenyl]-4-oxochromen-7-yloxy}methyl)benzoate;
7-({5-[3-fluoro-5-(trifluoromethyl)phenyl](1,2,4-oxadiazol-3-yl)}methoxy)-3-[4-(hydroxymethyl)phenyl]chromen-4-one;
4-[7-({5-[3-fluoro-5-(trifluoromethyl)phenyl](1,2,4-oxadiazol-3-yl)}methoxy)-4-oxochromen-3-yl]benzoic acid;
7-({5-[3-fluoro-5-(trifluoromethyl)phenyl](1,2,4-oxadiazol-3-yl)}methoxy)-3-(4-morpholin-4-ylphenyl)chromen-4-one;
7-({5-methyl-2-[4-(trifluoromethyl)phenyl](1,3-thiazol-4-yl)}methoxy)-3-(4-morpholin-4-ylphenyl)chromen-4-one;
7-({3-[5-fluoro-3-(trifluoromethyl)phenyl](1,2,4-oxadiazol-5-yl)}methoxy)-3-{4-[(methylsulfonyl)amino]phenyl}chromen-4-one;
2-fluoro-5-[7-({5-[5-fluoro-3-(trifluoromethyl)phenyl](1,2,4-oxadiazol-3-yl)}methoxy)-4-oxochromen-3-yl]benzenecarbonitrile;
ethyl 2-(3-{4-[(ethoxycarbonyl)methoxy]phenyl}-4-oxochromen-7-yloxy)acetate;
7-{([5-(4-fluorophenyl)(1,2,4-oxadiazol-3-yl)]methoxy}-3-(4-hydroxyphenyl)chromen-4-one;
3-[7-({5-[5-fluoro-3-(trifluoromethyl)phenyl](1,2,4-oxadiazol-3-yl)}methoxy)-4-oxochromen-3-yl]benzenecarbonitrile;
3-(3-acetylphenyl)-7-({5-[5-fluoro-3-(trifluoromethyl)phenyl](1,2,4-oxadiazol-3-yl)}methoxy)chromen-4-one;
7-({5-[5-fluoro-3-(trifluoromethyl)phenyl](1,2,4-oxadiazol-3-yl)}methoxy)-3-{4-[(methylsulfonyl)amino]phenyl}chromen-4-one;
4-[7-({5-[5-fluoro-3-(trifluoromethyl)phenyl](1,2,4-oxadiazol-3-yl)}methoxy)-4-oxochromen-3-yl]benzamide;
3-[2,4-bis(tert-butoxy)pyrimidin-5-yl]-7-({5-[5-fluoro-3-(trifluoromethyl)phenyl](1,2,4-oxadiazol-3-yl)}methoxy)chromen-4-one; and
5-[7-({5-[5-fluoro-3-(trifluoromethyl)phenyl](1,2,4-oxadiazol-3-yl)}methoxy)-4-oxochromen-3-yl]-1,3-dihydropyrimidine-2,4-dione.

EXAMPLE 4

Preparation of a Compound of Formula I

A. Preparation of a Compound of Formula I in which $R^1$ is 2-[5-fluoro-3-(trifluoromethyl)phenyl]-1,3-oxazole, $R^2$ is 4-Hydroxy $R^3$ is Hydrogen, X, Y and Z are —CH—, V is Oxygen, and W is Methylene

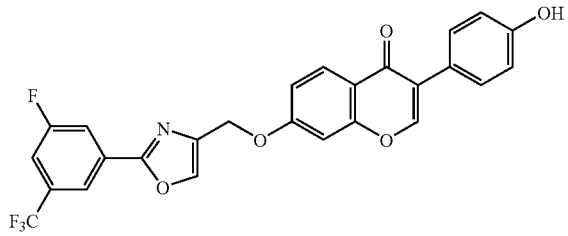

4',7-Dihydroxyisoflavone (101.7 mg, 0.40 mmol), 4-(chloromethyl)-2-[5-fluoro-3-(trifluoromethyl)phenyl]-1,3-oxazole, prepared as described in Example 1 (111.8 mg, 040 mmol, 1.0 equiv.), sodium iodide (59.6 mg, 0.40 mmol, 1.0 equiv), and potassium hydroxide powder (22.4 mg, 0.4 mmol, 1.0 equiv) were placed in a 25 mL flask equipped with a condenser. To the flask was added dimethylsulfoxide (3 mL) at room temperature under nitrogen. The solution was heated at 60° C. for 1 hour. To the mixture were added water (30 mL) and the whole was extracted with ethyl acetate (30 mL×3). The combined organic layers were washed with brine (30 mL) and dried with $Na_2SO_4$, to give a crude mixture as colorless oil (204.7 mg). The crude mixture was purified by column-chromatography (silica gel=25 g, eluting with hexane/ethyl acetate=7:1) to give crude product (149.3 mg) as colorless crystals. Recrystallization of this crude product gave 7-({2-[5-fluoro-3-(trifluoromethyl)phenyl]-(1,3-oxazol-4-yl)}methoxy)-3-(4-hydroxyphenyl)chromen-4-one as a colorless powder.

B.

Similarly, following the procedure of Example 4A above, substituting other compounds of formula (4) for 4-(chloromethyl)-2-[5-fluoro-3-(trifluoromethyl)phenyl]-1,3-oxazole, the following compounds of Formula I were prepared:
3-(4-hydroxyphenyl)-7-({2-[3-(trifluoromethyl)phenyl](1,3-oxazol-4-yl)}methoxy)chromen-4-one;
7-({2-[5-fluoro-3-(trifluoromethyl)phenyl](1,3-oxazol-4-yl)}methoxy)-3-(4-hydroxyphenyl)chromen-4-one;
3-(4-hydroxyphenyl)-7-{[2-(3,4,5-trifluorophenyl)(1,3-oxazol-4-yl)]methoxy}chromen-4-one;
7-{[2-(3,5-difluorophenyl)(1,3-oxazol-4-yl)]methoxy}-3-(4-hydroxyphenyl)chromen-4-one;
7-{[2-(3,4-difluorophenyl)(1,3-oxazol-4-yl)]methoxy}-3-(4-hydroxyphenyl)chromen-4-one;
7-{[2-(4-fluorophenyl)(1,3-oxazol-4-yl)]methoxy}-3-(4-hydroxyphenyl)chromen-4-one; and
7-{[2-(4-chlorophenyl)(1,3-oxazol-4-yl)]methoxy}-3-(4-hydroxyphenyl)chromen-4-one.

EXAMPLE 5

Preparation of a Compound of Formula I

A. Preparation of a Compound of Formula I in which $R^1$ is 3-(Trifluoromethyl)-phenyl[1,2,4]oxadiazolyl, $R^2$ is 4-Hydroxy, $R^3$ is Hydrogen, X, Y and Z are —CH—, V is Oxygen, and W is Methylene

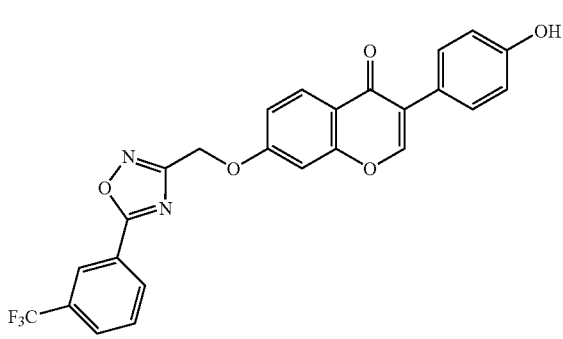

A mixture of daidzein (100 mg, 0.4 mmol), 3-chloromethyl-5-(3-trifluoromethyl(phenyl[1,2,4]oxadiazole (108 mg, 0.41 mmol) and potassium carbonate (0.63 mg, 0.45 mmol) in anhydrous N,N-dimethylformamide (2 ml) was heated with stirring under argon at 80° C. for 4.5 hours. After cooling to room temperature, the mixture was quenched with about 12 ml of water, and stirred for 30 minutes. The precipitate formed was filtered off, washed three times with water, and dried under vacuum to provide crude product (152 mg). Chromatography of the crude product on silica gel, eluting with 5% to 50% ethyl acetate/hexanes, provided pure 3-(4-hydroxyphenyl)-7-({5-[3-(trifluoromethyl)phenyl](1,2,4-oxadiazol-3-yl)}methoxy)chromen-4-one.

$^1$H NMR (400 MHz, DMSO-d6) δ: 9.58 (s, 1H), 8.48-8.39 (m, 3H), 8.12 (d, 1H, J=8.0 Hz), 8.08 (d, 1H, J=8.8 Hz), 7.92 (t, 1H, J=8.8 Hz), 7.42-7.38 (m, 3H), 7.23 (d, 1H, J=9.2 Hz), 6.82 (d, 2H, J=8.8 Hz), 5.61 (s, 2H). LC/MS analysis: $t_R$=21.98 min (linear gradient B 5%→90%), (ESI) m/z 481.5 (M+H)$^+$.

B. Alternative Preparation of a Compound of Formula I in which $R^1$ is 3-(Trifluoromethyl)phenyl[1,2,4]oxadiazolyl, $R^2$ is 4-Hydroxy $R^3$ is Hydrogen, X, Y and X are —CH—, V is Oxygen, and W is Methylene To a suspension of daidzein (2.0 g, 7.87 mmol) in acetone (80 ml) 2 N aqueous potassium hydroxide (3.94 ml, 7.87 mmol) was added, and the mixture was sonicated for a few minutes. To this mixture was added 3-chloromethyl-5-(3-trifluoromethylphenyl)-[1,2,4]oxadiazole (2.17 g, 8.26 mmol), and the reaction mixture was refluxed for 3 days. The mixture was concentrated under reduced pressure, and the residue dissolved in methanol, mixed with silica gel, and the solvent removed under reduced pressure. Purification by flash column chromatography, eluting with methylene chloride/methanol (95/5 to 90/10) provided pure 3-(4-hydroxyphenyl)-7-({5-[3-(trifluoromethyl)phenyl]-(1,2,4-oxadiazol-3-yl)}methoxy)chromen-4-one as a white solid.

C. Preparation of Compounds of Formula I in which $R^3$ is Hydrogen, X, Y and Z are —CH—, and V is Oxygen, varying $R^1$ and $R^2$ Similarly, following the procedures of Example 5A or 5B above, replacing 3-chloromethyl-5-(3-trifluoromethylphenyl)-[1,2,4]oxadiazole by other compounds of formula $R^1CH_2X$, where $R^1$ and X are as defined above, the following compounds of Formula I were prepared.

3-{[3-(4-hydroxyphenyl)-4-oxochromen-7-yloxy]methyl}benzoic acid; $^1$H NMR (400 MHz, DMSO-d$_6$) δ: 13.1 (br s, 1H), 9.59 (br S, 1H), 8.38 (s, 1H), 8.08 (s, 1H), 8.05 (d, 1H, J=9.0 Hz), 7.94 (d, 1H, J=7.8 Hz), 7.75 (d, 1H, J=7.7 Hz), 7.56 (dd, 1H, J=7.5 Hz, J=7.8 Hz), 7.40 (d, 2H, J=8.7 Hz), 7.29 (d, 1H, J=1.9 Hz), 7.18 (dd, 1H, J=1.9 Hz, J=9.0 Hz), 6.82 (d, 2H, J=8.7 Hz), 5.37 (s, 2H). (ESI) m/z 389 (M+H)$^+$.

3-(4-hydroxyphenyl)-7-[(5-phenyl(1,2,4-oxadiazol-3-yl))methoxy]chromen-4-one; $^1$H NMR (300 MHz, DMSO-d$_6$) δ: 9.58 (s, 1H), 8.41 (s, 1H), 8.15 (d, 2H, J=7.2 Hz), 8.08 (d, 1H, J=9.0 Hz), 7.72-7.63 (m, 3H), 7.42-7.38 (m, 3H), 7.23 (d, 1H, J=9.0 Hz), 6.82 (d, 2H, J=8.7 Hz), 5.58 (s, 2H). (ESI) m/z 413.4 (M+H)$^+$.

3-{[3-(4-hydroxyphenyl)-4-oxochromen-7-yloxy]methyl}benzenecarbonitrile; (ESI) m/z 370 (M+H)$^+$.

3-{[3-(4-hydroxyphenyl)-4-oxochromen-7-yloxy]methyl}benzamide; $^1$H NMR (300 MHz, DMSO-d$_6$) δ: 9.56 (s, 1H), 8.41 (s, 1H), 8.35 (d, 2H, J=8.1 Hz), 8.09-8.01 (m, 3H), 7.40 (m, 3H), 7.22 (dd, 1H, J=8.8, 2.1 Hz), 6.82 (d, 2H, J=8.7 Hz), 5.61 (s, 2H). (ESI) m/z 481.6 (M+H)$^+$ 3-(4-hydroxyphenyl)-7-{[5-(2-methoxyphenyl)(1,2,4-oxadiazol-3-yl)]methoxy}chromen-4-one; $^1$H NMR (400 MHz, DMSO-d$_6$) δ: 9.57 (s, 1H), 8.40 (s, 1H), 8.07 (d, 1H, J=8.8 Hz), 8.03 (dd, 1H, J=8.0, 1.6 Hz), 7.69 (m, 1H), 7.42-7.15 (m, 6H), 6.82 (d, 2H, J=8.4 Hz), 5.56 (s, 2H), 3.95 (s, 3H). (ESI) m/z 443.3 (M+H)$^+$ 3-(4-hydroxyphenyl)-7-{[3-(trifluoromethyl)phenyl]methoxy}chromen-4-one; (K-28-AR-1) $^1$H NMR (400 MHz, DMSO-d$_6$) δ: 9.55 (s, 1H), 8.39 (s, 1H), 8.06 (d, 1H, J=8.8 Hz), 7.89 (s, 1H), 7.84-7.66 (m, 3H), 7.41 (d, 2H, 8.4 Hz), 7.29 (s, 1H), 7.20 (d, 1H, J=8.4 Hz), 6.82 (d, 2H, J=8.4 Hz), 5.40 (s, 2H). (ESI) m/z 413 (M+H)$^+$.

3-(4-hydroxyphenyl)-7-{[4-methoxy-3-(trifluoromethyl)phenyl]methoxy}chromen-4-one; (DM-K-4-P3); $^1$H NMR (300 MHz, DMSO-d$_6$) δ: 9.54 (s, 1H), 8.43-8.40 (m, 2H), 8.26 (d, 1H, J=1.8 Hz), 8.07 (d, 1H, J=8.9 Hz), 7.54 (d, 1H, J=8.9 Hz), 7.41 (d, 2H, J=8.7 Hz), 7.37 (d, 1H, J=2.4 Hz), 7.21 (dd, 1H, J=2.4 Hz, J=8.9 Hz), 6.82 (d, 2H, J=8.7 Hz), 5.56 (s, 2H), 4.03 (s, 3H). (ESI) m/z 511 (M+H)$^+$ 7-{[3-fluoro-5-(trifluoromethyl)phenyl]methoxy}-3-(4-hydroxyphenyl)chromen-4-one; (DM-K-28-AR-2), (ESI) m/z 431 (M+H)$^+$.

7-({5-[3-fluoro-5-(trifluoromethyl)phenyl](1,2,4-oxadiazol-3-yl)}methoxy)-3-(4-hydroxyphenyl)chromen-4-one; $^1$H NMR (400 MHz, DMSO-d$_6$) δ: 9.57 (s, 1H), 8.42 (s, 1H), 8.33 (d, 1H, J=8.4 Hz), 8.26 (s, 1H), 8.17 (d, 1H, J=8.4 Hz), 8.08 (d, 1H, J=8.8 Hz), 7.41 (m, 3H), 7.22 (dd, 1H, J=9.2, 2.0 Hz), 6.82 (d, 2H, J=8.8 Hz), 5.62 (s, 2H), (ESI) m/z 499 (M+H)$^+$ 7-({5-[4-fluoro-3-(trifluoromethyl)phenyl](1,2,4-oxadiazol-3-yl)}methoxy)-3-(4-hydroxyphenyl)chromen-4-one; $^1$H NMR (300 MHz, DMSO-d$_6$) δ: 9.54 (s, 1H), 8.55-8.48 (m, 1H), 8.44-8.40 (m, 2H), 8.07 (d, 1H, J=8.9 Hz), 7.83 (dd, 1H, J=9.8 Hz, J=9.5 Hz), 7.41 (d, 2H, J=8.6 Hz), 7.38 (d, 1H, J=2.4 Hz), 7.21 (dd, 1H, J=2.4 Hz, J=8.9 Hz), 6.82 (d, 2H, J=8.6 Hz), 5.59 (s, 2H), (ESI) m/z 499 (M+H)$^+$.

7-({5-[2,5-bis(trifluoromethyl)phenyl](1,2,4-oxadiazol-3-yl)}methoxy)-3-(4-hydroxyphenyl)chromen-4-one; $^1$H NMR (400 MHz, DMSO-d$_6$) δ: 9.57 (s, 1H), 8.52 (s, 1H), 8.42 (s, 1H), 8.38-8.31 (m, 2H), 8.08 (d, 1H, J=9.0 Hz), 7.41 (d, 2H, 8.7 Hz), 7.40 (s, 1H), 7.22 (dd, 1H, J=1.9 Hz, J=9.0 Hz), 6.82 (d, 2H, J=8.7 Hz), 5.66 (s, 2H), (ESI) m/z 549 (M+H)$^+$.

prop-2-enyl 3-(3-{[3-(4-hydroxyphenyl)-4-oxochromen-7-yloxy]methyl}-1,2,4-oxadiazol-5-yl)benzoate; (ESI) m/z 497 (M+H)$^+$.

prop-2-enyl 3-{[3-(4-hydroxyphenyl)-4-oxochromen-7-yloxy]methyl}benzoate; LC/MS analysis: $t_R$=23.62 min (isocratic, 65% B), (ESI) m/z 429 (M+H)$^+$.

methyl 3-{[3-(4-hydroxyphenyl)-4-oxochromen-7-yloxy]methyl}benzoate; $^1$H NMR (400 MHz, DMSO-d$_6$) δ: 9.54 (s, 1H), 8.38 (s, 1H), 8.10 (s, 1H), 8.05 (d, 1H, J=8.8 Hz), 7.96 (d, 1H, J=7.7 Hz), 7.79 (d, 1H, J=7.5 Hz), 7.60 (dd, 1H, J=7.5 Hz, J=7.7 Hz), 7.41 (d, 2H, J=8.5 Hz), 7.27 (s, 1H), 7.18 (dd, 1H, J=1.5 Hz, J=9.0 Hz), 6.82 (d, 2H, J=8.5 Hz), 5.38 (s, 2H), 3.88 (s, 3H), (ESI) m/z 403 (M+H)⁺.

ethyl 4-{[3-(4-hydroxyphenyl)-4-oxochromen-7-yloxy]methyl}benzoate; (ESI) m/z 417 (M+H)⁺.

methylethyl 3-{[3-(4-hydroxyphenyl)-4-oxochromen-7-yloxy]methyl}benzoate; ¹H NMR (400 MHz, DMSO-$d_6$) δ: 9.56 (s, 1H), 8.39 (s, 1H), 8.08 (s, 1H), 8.05 (d, 1H, J=9.0 Hz), 7.95 (d, 1H, J=7.8 Hz), 7.78 (d, 1H, J=7.7 Hz), 7.58 (dd, 1H, J=7.6 Hz, J=7.9 Hz), 7.41 (d, 2H, J=8.3 Hz), 7.28 (d, 1H, J=1.9 Hz), 7.18 (dd, 1H, J=1.9 Hz, J=9.0 Hz), 6.82 (d, 2H, J=8.3 Hz), 5.37 (s, 2H), 5.18-5.14 (m, 1H), 1.33 (d, 6H, J=6.3 Hz), (ESI) m/z 431 (M+H)⁺.

methyl 4-{[3-(4-hydroxyphenyl)-4-oxochromen-7-yloxy]methyl}benzoate.

4-{[3-(4-hydroxyphenyl)-4-oxochromen-7-yloxy]methyl}benzoic acid; (ESI) m/z 389 (M+H)⁺.

4-{[3-(4-hydroxyphenyl)-4-oxochromen-7-yloxy]methyl}benzamide; ¹H NMR (400 MHz, DMSO-$d_6$) δ: 9.54 (s, 1H), 8.38 (s, 1H), 8.07-8.04 (m, 3H), 7.87 (d, 1H, J=8.0 Hz), 7.66 (d, 1H, J=7.6 Hz), 7.51 (m, 1H), 7.41 (m, 3H), 7.28 (d, 1H, J=2.0 Hz), 7.18 (dd, 1H, J=9.2, 2.0 Hz), 6.82 (d, 2H, J=8.4 Hz), 5.33 (s, 2H), (ESI) m/z 388/389.

3-(4-hydroxyphenyl)-7-({5-[4-(trifluoromethyl)phenyl](1,2,4-oxadiazol-3-yl)}methoxy)chromen-4-one; ¹H NMR (300 MHz, DMSO-$d_6$) δ: 9.56 (s, 1H), 8.41 (s, 1H), 8.35 (d, 2H, J=8.1 Hz), 8.09-8.01 (m, 3H), 7.40 (m, 3H), 7.22 (dd, 1H, J=8.8, 2.1 Hz), 6.82 (d, 2H, J=8.7 Hz), 5.61 (s, 2H), (ESI) m/z 481.6 (M+H)⁺.

3-(4-hydroxyphenyl)-7-{[5-(3-methoxyphenyl)(1,2,4-oxadiazol-3-yl)]methoxy}chromen-4-one;

7-({5-[3,5-bis(trifluoromethyl)phenyl](1,2,4-oxadiazol-3-yl)}methoxy)-3-(4-hydroxyphenyl)chromen-4-one; ¹H NMR (400 MHz, DMSO-$d_6$) δ: 9.57 (d, 1H, J=1.6 Hz), 8.69 (s, 2H), 8.56 (s, 1H), 8.41 (d, 1H, J=2.0 Hz), 8.07 (dd, 1H, J=8.8, 2.0 Hz), 7.40 (m, 3H), 7.22 (d, 1H, J=8.8 Hz), 6.82 (d, 2H, J=6.4 Hz), 5.63 (s, 2H), (ESI) m/z 549.1 (M+H)⁺

3-(3-{[3-(4-hydroxyphenyl)-4-oxochromen-7-yloxy]methyl}-1,2,4-oxadiazol-5-yl)benzenecarbonitrile; (ESI) m/z 438 (M+H)⁺

3-(3-{[3-(4-hydroxyphenyl)-4-oxochromen-7-yloxy]methyl}-1,2,4-oxadiazol-5-yl)benzoic acid;

7-{[5-(3-fluorophenyl)(1,2,4-oxadiazol-3-yl)]methoxy}-3-(4-hydroxyphenyl)chromen-4-one. ¹H NMR (300 MHz, DMSO-d6) δ: 9.55 (s, 1H), 8.40 (s, 1H), 8.08 (d, 1H, J=8.7 Hz), 8.00 (d, 1H, J=7.8 Hz), 7.94 (d, 1H, J=9.0 Hz), 7.73-7.60 (m, 2H), 7.42-7.38 (m, 31H), 7.21 (dd, 1H, J=9.0, 2.4 Hz), 6.82 (d, 2H, J=8.7 Hz), 5.59 (s, 2H), (ESI) m/z 431 (M+H)⁺.

3-(4-hydroxyphenyl)-7-[(3-phenyl(1,2,4-oxadiazol-5-yl))methoxy]chromen-4-one; (ESI) m/z 413.4 (M+H)⁺.

3-(4-hydroxyphenyl)-7-({3-[3-(trifluoromethyl)phenyl](1,2,4-oxadiazol-5-yl)}methoxy)chromen-4-one; (ESI) m/z 481.6 (M+H)⁺.

3-(4-hydroxyphenyl)-7-({3-[4-chlorophenyl](1,2,4-oxadiazol-5-yl)}methoxy)chromen-4-one; (ESI) m/z 447.2 (M+H)⁺.

3-(4-hydroxyphenyl)-2-(trifluoromethyl)-7-({5-[3-(trifluoromethyl)phenyl]-(1,2,4-oxadiazol-3-yl)}methoxy)chromen-4-one; ¹H NMR (300 MHz, DMSO-$d_6$) δ: 9.64 (s, 1H), 8.45 (d, 1H, J=7.8 Hz), 8.39 (s, 1H), 8.17-7.83 (m, 3H), 7.53 (d, 1H, J=2.4 Hz), 7.27 (dd, 1H, J=8.7, 2.1 Hz), 7.08 (d, 2H, J=8.7 Hz), 6.82 (d, 2H, J=8.4 Hz), 5.65 (s, 2H), (ESI) m/z 549 (M+H)⁺.

7-({5-[5-fluoro-3-(trifluoromethyl)phenyl](1,2,4-oxadiazol-3-yl)}methoxy)-3-(4-hydroxyphenyl)-2-(trifluoromethyl)chromen-4-one; ¹H NMR (400 MHz, DMSO-$d_6$) δ: 9.67 (s, 1H), 8.32 (d, 1H, J=8.4 Hz), 8.25 (d, 1H, J=8.1 Hz), 8.17 (d, 1H, J=8.4 Hz), 8.02 (d, 1H, J=8.4 Hz), 7.54 (d, 1H, J=1.6 Hz), 7.27 (dd, 1H, J=8.8, 2.4 Hz), 7.08 (d, 2H, J=8.0 Hz), 6.82 (d, 2H, J=8.8 Hz), 5.66 (s, 2H). (ESI) m/z 567 (M+H)⁺

3-(4-hydroxyphenyl)-7-({5-[4-methoxy-3-(trifluoromethyl)phenyl](1,2,4-oxadiazol-3-yl)}methoxy)-2-(trifluoromethyl)chromen-4-one; (ESI) m/z 579 (M+H)⁺.

3-{[3-(4-hydroxyphenyl)-4-oxochromen-7-yloxy]methyl}benzenecarbonitrile;

3-(3-{[3-(4-hydroxyphenyl)-4-oxochromen-7-yloxy]methyl}-1,2,4-oxadiazol-5-yl)benzoic acid.

3-(4-hydroxyphenyl)-7-({5-[3-(trifluoromethyl)phenyl]isoxazol-3-yl}methoxy)chromen-4-one;

7-{[5-(trifluoromethyl)(3-pyridyl)]methoxy}-3-(4-{[6-(trifluoromethyl)(3-pyridyl)]methoxy}phenyl)chromen-4-one;

3-(4-hydroxyphenyl)-7-[(5-(3-pyridyl)(1,2,4-oxadiazol-3-yl))methoxy]chromen-4-one;

3-(4-hydroxyphenyl)-7-[(5-(2-pyridyl)(1,2,4-oxadiazol-3-yl))methoxy]chromen-4-one;

methyl 2-{[3-(4-hydroxyphenyl)-4-oxochromen-7-yloxy]methyl}-1,3-oxazole-5-carboxylate;

7-{[5-(4-fluorophenyl)(1,2,4-oxadiazol-3-yl)]methoxy}-3-{4-[(methylsulfonyl)amino]-phenyl}chromen-4-one;

2-{[3-(4-hydroxyphenyl)-4-oxochromen-7-yloxy]methyl}-1,3-oxazole-5-carboxylic acid;

methyl 3-({3-[4-((1Z)-1-amino-2-methoxy-2-azavinyl)phenyl]-4-oxochromen-7-yloxy}methyl)benzoate;

7-{2-[4-(4-chlorophenyl)pyrazolyl]ethoxy}-3-(4-hydroxyphenyl)chromen-4-one;

3-(4-hydroxyphenyl)-7-[(6-pyrazolyl(3-pyridyl))methoxy]chromen-4-one;

7-[(2R)-2-hydroxy-3-({[3-(trifluoromethyl)phenyl]methyl}amino)propoxy]-3-(4-hydroxyphenyl)chromen-4-one;

3-(4-hydroxyphenyl)-7-[({[3-(trifluoromethyl)phenyl]methyl}amino)methoxy]chromen-4-one;

7-((2R)-3-{[(3,5-difluorophenyl)methyl]amino}-2-hydroxypropoxy)-3-(4-hydroxyphenyl)chromen-4-one;

7-(3-{[(1R)-1-(4-fluorophenyl)ethyl]amino}-2-oxopropoxy)-3-(4-hydroxyphenyl)chromen-4-one;

3-(4-hydroxyphenyl)-7-(3-phenylpropoxy)chromen-4-one;

7-{[5-(3-fluorophenyl)(1,3,4-oxadiazol-2-yl)]methoxy}-3-(4-hydroxyphenyl)chromen-4-one;

3-(4-hydroxyphenyl)-7-{[3-(trifluoromethyl)phenyl]ethoxy}chromen-4-one;

3-(4-hydroxyphenyl)-7-({5-[3-(trifluoromethyl)phenyl](1,3,4-oxadiazol-2-yl)}methoxy)chromen-4-one;

3-(4-hydroxyphenyl)-7-[(2-phenyl(1,3-oxazol-5-yl))methoxy]chromen-4-one;

7-({5-[3,5-bis(trifluoromethyl)phenyl]isoxazol-3-yl}methoxy)-3-(4-hydroxyphenyl)chromen-4-one;

3-(4-hydroxyphenyl)-7-({5-[3-(trifluoromethyl)phenyl]isoxazol-3-yl}methoxy)chromen-4-one;

3-{4-[(methylsulfonyl)amino]phenyl}-7-[(2-phenyl(1,3-oxazol-4-yl))methoxy]chromen-4-one;

2-[3-(4-hydroxyphenyl)-4-oxochromen-7-yloxy]-N-[3-(trifluoromethyl)phenyl]-acetamide;

7-{[5-(2-chlorophenyl)(1,3,4-thiadiazol-2-yl)]methoxy}-3-(4-hydroxyphenyl)chromen-4-one;

4-[7-({4-methyl-2-[4-(trifluoromethyl)phenyl](1,3-thiazol-5-yl)}methoxy)-4-oxochromen-3-yl]benzenecarbonitrile;

3-{4-[(methylsulfonyl)amino]phenyl}-7-({4-methyl-2-[4-(trifluoromethyl)phenyl](1,3-thiazol-5-yl)}methoxy)chromen-4-one;

3-(6-methoxy(3-pyridyl))-7-({4-methyl-2-[4-(trifluoromethyl)phenyl](1,3-thiazol-5-yl)}methoxy)chromen-4-one;

4-[7-({5-[5-fluoro-3-(trifluoromethyl)phenyl](1,3,4-oxadiazol-2-yl)}methoxy)-4-oxochromen-3-yl]benzenecarbonitrile;
4-[4-oxo-7-({3-[3-(trifluoromethyl)phenyl]isoxazol-5-yl}methoxy)chromen-3-yl]benzenecarbonitrile;
7-({5-[3-fluoro-5-(trifluoromethyl)phenyl](1,2,4-oxadiazol-3-yl)}methoxy)-3-{4-[(methylsulfonyl)amino]phenyl}chromen-4-one;
7-({5-[3-fluoro-5-(trifluoromethyl)phenyl](1,2,4-oxadiazol-3-yl)}methoxy)-3-[4-(methylsulfonyl)phenyl]chromen-4-one;
4-[7-({5-[3-fluoro-5-(trifluoromethyl)phenyl](1,2,4-oxadiazol-3-yl)}methoxy)-4-oxochromen-3-yl]benzamide;
3-(3-acetylphenyl)-7-({5-[3-fluoro-5-(trifluoromethyl)phenyl](1,2,4-oxadiazol-3-yl)}methoxy)chromen-4-one;
7-({5-[3-fluoro-5-(trifluoromethyl)phenyl](1,3,4-oxadiazol-2-yl)}methoxy)-3-(4-hydroxyphenyl)chromen-4-one;
7-({5-[3-fluoro-5-(trifluoromethyl)phenyl](1,2,4-oxadiazol-3-yl)}methoxy)-3-(5-hydropyrazol-4-yl)chromen-4-one;
ethyl 3-[7-({3-[3-fluoro-5-(trifluoromethyl)phenyl](1,2,4-oxadiazol-5-yl)}ethoxy)-4-oxochromen-3-yl]benzoate;
3-(4-hydroxyphenyl)-7-({2-[4-(trifluoromethyl)phenyl](1,3-thiazol-5-yl)}methoxy)chromen-4-one;
7-[2-(3-fluorophenyl)-2-oxoethoxy]-3-(4-hydroxyphenyl)chromen-4-one;
7-({5-[3-fluoro-5-(trifluoromethyl)phenyl](1,2,4-oxadiazol-3-yl)}ethoxy)-3-(4-hydroxyphenyl)chromen-4-one;
7-({5-[3-fluoro-5-(trifluoromethyl)phenyl](1,2,4-oxadiazol-3-yl)}methoxy)-3-(4-{[(4-methylphenyl)sulfonyl]amino}phenyl)chromen-4-one;
7-{[5-(2-chlorophenyl)(1,3,4-oxadiazol-2-yl)]methoxy}-3-(4-hydroxyphenyl)chromen-4-one;
7-{[5-(4-fluorophenyl)(1,3,4-oxadiazol-2-yl)]methoxy}-3-(4-hydroxyphenyl)chromen-4-one;
3-(4-hydroxyphenyl)-7-(4-pyridylmethoxy)chromen-4-one;
3-{4-[(methylsulfonyl)amino]phenyl}-7-({2-[4-(trifluoromethyl)phenyl](1,3-thiazol-5-yl)}methoxy)chromen-4-one;
2-[3-(4-hydroxyphenyl)-4-oxochromen-7-yloxy]-N-[2-(trifluoromethyl)phenyl]-acetamide;
3-(4-hydroxyphenyl)-7-{2-oxo-2-[2-(trifluoromethyl)phenyl]ethoxy}chromen-4-one;
3-(1H-indazol-5-yl)-7-({5-[5-fluoro-3-(trifluoromethyl)phenyl](1,2,4-oxadiazol-3-yl)}methoxy)chromen-4-one;
3-(4-hydroxyphenyl)-7-(2-phenylethoxy)chromen-4-one;
2-[3-(4-hydroxyphenyl)-4-oxochromen-7-yloxy]ethanenitrile;
7-[2-(4-chlorophenoxy)ethoxy]-3-(4-hydroxyphenyl)chromen-4-one;
5-{4-[7-({5-[5-fluoro-3-(trifluoromethyl)phenyl](1,2,4-oxadiazol-3-yl)}methoxy)-4-oxochromen-3-yl]phenyl}-1,3,5,6-tetrahydropyrimidine-2,4-dione;
N-[(1R)-1-(4-fluorophenyl)ethyl]-2-[3-(4-hydroxyphenyl)-4-oxochromen-7-yloxy]acetamide;
3-(4-hydroxyphenyl)-7-(2-pyridylmethoxy)chromen-4-one;
2-fluoro-5-[7-({5-[5-fluoro-3-(trifluoromethyl)phenyl](1,2,4-oxadiazol-3-yl)}methoxy)-4-oxochromen-3-yl]benzenecarbonitrile;
7-(2-pyridylmethoxy)-3-[4-(2-pyridylmethoxy)phenyl]chromen-4-one;
3-(4-hydroxyphenyl)-7-[(5-(4-pyridyl)(1,2,4-oxadiazol-3-yl))ethoxy]chromen-4-one;
3-(4-hydroxyphenyl)-7-[(5-(3-pyridyl)(1,2,4-oxadiazol-3-yl))ethoxy]chromen-4-one;
3-(4-hydroxyphenyl)-7-[(5-(2-pyridyl)(1,2,4-oxadiazol-3-yl))ethoxy]chromen-4-one;
3-(4-hydroxyphenyl)-7-{[5-(trifluoromethyl)(3-pyridyl)]methoxy}chromen-4-one;
7-{[5-(4-chlorophenyl)isoxazol-3-yl]methoxy}-3-(4-hydroxyphenyl)chromen-4-one;
7-{[5-(3,4-dichlorophenyl)isoxazol-3-yl]methoxy}-3-(4-hydroxyphenyl)chromen-4-one;
7-{[5-(4-chlorophenyl)isoxazol-3-yl]methoxy}-3-(4-hydroxyphenyl)chromen-4-one;
7-[(2R)-2-hydroxy-3-({[3-(trifluoromethyl)phenyl]methyl}amino)propoxy]-3-(4-hydroxyphenyl)chromen-4-one;
3-(4-hydroxyphenyl)-7-[2-({[3-(trifluoromethyl)phenyl]methyl}amino)ethoxy]chromen-4-one;
7-((2R)-3-{[(3,5-difluorophenyl)methyl]amino}-2-hydroxypropoxy)-3-(4-hydroxyphenyl)chromen-4-one;
methyl 2-{[3-(4-hydroxyphenyl)-4-oxochromen-7-yloxy]methyl}-1,3-oxazole-4-carboxylate;
which was hydrolyzed under standard hydrolysis conditions to give:
2-{[3-(4-hydroxyphenyl)-4-oxochromen-7-yloxy]methyl}-1,3-oxazole-4-carboxylic acid;
N-[(1S)-1-(4-fluorophenyl)ethyl]-2-[3-(4-hydroxyphenyl)-4-oxochromen-7-yloxy]acetamide;
7-{[5-(4-fluorophenyl)(1,2,4-oxadiazol-3-yl)]methoxy}-3-(4-hydroxyphenyl)chromen-4-one;
7-{[5-(4-fluorophenyl)(1,2,4-oxadiazol-3-yl)]methoxy}-3-{4-[(methylsulfonyl)-amino]phenyl}chromen-4-one;
7-{3-[4-(4-chlorophenyl)pyrazolyl]propoxy}-3-(4-hydroxyphenyl)chromen-4-one;
3-(4-hydroxyphenyl)-7-(3-phenylpropoxy)chromen-4-one;
3-(4-hydroxyphenyl)-7-[(6-pyrazolyl(3-pyridyl))methoxy]chromen-4-one;
7-((2R)-2-hydroxy-3-phenylpropoxy)-3-(4-hydroxyphenyl)chromen-4-one;
3-(4-hydroxyphenyl)-7-[(5-(3-pyridyl)(1,3,4-oxadiazol-2-yl))methoxy]chromen-4-one;
3-[(2-hydroxy-3-{4-[(methylsulfonyl)amino]phenyl}-4-oxochromen-7-yloxy)methyl]-benzoic acid;
7-{[5-(4-fluorophenyl)(1,3,4-oxadiazol-2-yl)]ethoxy}-3-(4-hydroxyphenyl)chromen-4-one;
3-(4-hydroxyphenyl)-7-[(5-(3-pyridyl)(1,3,4-oxadiazol-2-yl))ethoxy]chromen-4-one;
3-(4-hydroxyphenyl)-7-[(3-(3-pyridyl)(1,2,4-oxadiazol-5-yl))methoxy]chromen-4-one;
3-(4-hydroxyphenyl)-7-({3-[3-(trifluoromethyl)phenyl](1,2,4-oxadiazol-5-yl)}methoxy)chromen-4-one;
3-(4-hydroxyphenyl)-7-[(5-(3-pyridyl)(1,3,4-oxadiazol-2-yl))ethoxy]chromen-4-one;
3-(4-hydroxyphenyl)-7-[(5-(4-pyridyl)(1,2,4-oxadiazol-3-yl))ethoxy]chromen-4-one;
(2-{[3-(4-hydroxyphenyl)-4-oxochromen-7-yloxy]methyl}(1,3-oxazol-4-yl))-N-methylcarboxamide;
4-{[3-(4-hydroxyphenyl)-4-oxochromen-7-yloxy]methyl}-7-methoxychromen-2-one;
7-{[5-(4-fluorophenyl)(1,3,4-oxadiazol-2-yl)]methoxy}-3-{4-[(methylsulfonyl)amino]-phenyl}chromen-4-one;
7-{[5-(3-aminophenyl)(1,3,4-oxadiazol-2-yl)]methoxy}-3-(4-hydroxyphenyl)chromen-4-one;
ethyl 1-{2-[3-(4-hydroxyphenyl)-4-oxochromen-7-yloxy]ethyl}pyrazole-4-carboxylate;
7-{2-[4-(3-chlorophenyl)piperazinyl]ethoxy}-3-(4-hydroxyphenyl)chromen-4-one;
3-(4-hydroxyphenyl)-7-(2-{4-[3-(trifluoromethyl)phenyl]piperazinyl}ethoxy)chromen-4-one;
3-(4-hydroxyphenyl)-7-[(5-(2-pyridyl)isoxazol-3-yl)methoxy]chromen-4-one;
7-({3-[3-fluoro-5-(trifluoromethyl)phenyl](1,2,4-oxadiazol-5-yl)}ethoxy)-3-(4-hydroxyphenyl)chromen-4-one;

7-[2-(4-fluorophenyl)ethoxy]-3-(4-hydroxyphenyl) chromen-4-one;

7-((1R)-1-{3-[3-fluoro-5-(trifluoromethyl)phenyl](1,2,4-oxadiazol-5-yl)}ethoxy)-3-(4-hydroxyphenyl)chromen-4-one;

7-((1S)-1-{3-[3-fluoro-5-(trifluoromethyl)phenyl](1,2,4-oxadiazol-5-yl)}ethoxy)-3-(4-hydroxyphenyl)chromen-4-one;

3-(4-hydroxyphenyl)-7-{2-[3-(trifluoromethyl)pyrazolyl]ethoxy}chromen-4-one; and 7-(1-{3-[3-fluoro-5-(trifluoromethyl)phenyl](1,2,4-oxadiazol-5-yl)}-isopropoxy)-3-(4-hydroxyphenyl)chromen-4-one.

D. Preparation of a Compound of Formula (3)

Similarly, following the procedures of Example 5A or 5B above, replacing 3-hydroxy isoflavone by commercially available isoflavones in which the 3-phenyl group is substituted with a nitro group and/or replacing 3-chloromethyl-5-(3-trifluoromethylphenyl)-[1,2,4]oxadiazole by other compounds of formula $R^1CH_2X$, where $R^1$ and X are as defined above, the following compounds of formula (3) were prepared.

methyl 3-{[3-(4-nitrophenyl)-4-oxochromen-7-yloxy]methyl}benzoate; (ESI) m/z 432 (M+H)$^+$.

3-(4-nitrophenyl)-7-({5-[3-(trifluoromethyl)phenyl](1,2,4-oxadiazol-3-yl)}methoxy)chromen-4-one; (ESI) m/z 510.5 (M+H)$^+$.

7-({5-[5-fluoro-3-(trifluoromethyl)phenyl](1,2,4-oxadiazol-3-yl)}methoxy)-3-(4-nitrophenyl)chromen-4-one; (ESI) m/z 528.1 (M+H)$^+$.

prop-2-enyl 3-(3-{[3-(4-nitrophenyl)-4-oxochromen-7-yloxy]methyl}-1,2,4-oxadiazol-5-yl)benzoate; (ESI) m/z 458 (M+H)$^+$.

3-{[3-(4-nitrophenyl)-4-oxochromen-7-yloxy]methyl}benzenecarbonitrile; (ESI) m/z 399 (M+H)$^+$.

methyl 3-{[3-(4-nitrophenyl)-4-oxochromen-7-yloxy]methyl}benzoate; (ESI) m/z 432 (M+H)$^+$.

7-(benzothiazol-2-ylmethoxy)-3-(4-hydroxyphenyl)chromen-4-one, and

3-[3-(4-nitrophenyl)-4-oxochromen-7-yloxymethyl]benzoic acid allyl ester.

E Preparation of Compounds of Formula I in which $R^2$ is 4-Hydroxy, $R^3$ is Hydrogen, X, Y and Z are —CH—, V is Oxygen and W is Methylene, varying $R^1$ Similarly, following the procedures of Example 5A or 5B above, replacing 3-hydroxy isoflavone by commercially available isoflavones in which the 3-phenyl group is substituted with a nitro group and/or replacing 3-chloromethyl-5-(3-trifluoromethylphenyl)-[1,2,4]oxadiazole by other compounds of formula $R^1CH_2X$, where $R^1$ and X are as defined above, other compounds of Formula I are prepared.

EXAMPLE 6

Preparation of a Compound of Formula I

A. Preparation of a Compound of Formula I in which $R^1$ is (3-(1H-1,2,3,4-Tetrazol-5-yl)phenyl)1,2,4-oxadiazol-5-yl), $R^2$ is 4-Hydroxy, $R^3$ is Hydrogen, X, Y and Z are —CH—, V is Oxygen, and W is Methylene

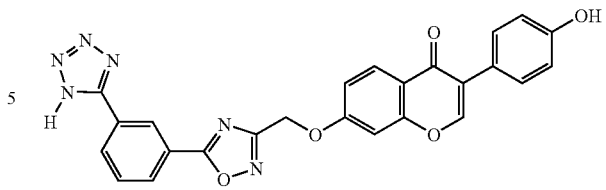

A mixture of 3-(3-{[3-(4-hydroxyphenyl)-4-oxochromen-7-yloxy]methyl}-1,2,4-oxadiazol-5-yl)benzenecarbonitrile (51 mg, 0.117 mmol), dibutyltin(IV) oxide (15 mg, 0.059 mmol, 0.5 equiv), and azidotrimethylsilane (81 mg, 0.702 mmol, 6 equiv) was microwaved at 150° C. for 20 minutes in 1,2-dimethoxyethane (0.6 ml). The reaction mixture was then dry-loaded onto a pre-packed column using silica gel and purified (silica gel, gradient, 100% $CH_2Cl_2$ to $CH_2Cl_2$/MeOH, 3:1) by flash chromatography to obtain the desired product protected by trimethylsilyl. This intermediate was suspended in acetonitrile (2 ml) and water (1 ml) and one drop of trifluoroacetic acid added. The volatile solvents were removed under vacuum to afford 3-(4-hydroxyphenyl)-7-{[5-(3-(1,2,3,4-tetrazol-5-yl)phenyl)(1,2,4-oxadiazol-3-yl)]methoxy}chromen-4-one (4 mg) $^1$H NMR (400 MHz, DMSO-d$_6$) δ: 9.57 (s, 1H), 8.82 (s, 1H), 8.42-8.33 (m, 3H), 8.09 (d, 1H, J=8.8 Hz), 7.92 (m, 1H), 7.41 (m, 3H), 7.24 (dd, 1H, J=8.8, 1.6 Hz), 6.82 (d, 2H, J=8.4 Hz), 5.62 (s, 2H). (ES−) m/z 479.2 (M−1)

B. Preparation of a Compound of Formula I in which $R^1$ is (3-(1H-1,2,3,4-Tetrazol-5-yl)phenyl), $R^2$ is 4-Hydroxy, $R^3$ is Hydrogen, X, Y and X are —CH—, V is Oxygen, and W is Methylene Similarly, starting with 3-{[3-(4-hydroxyphenyl)-4-oxochromen-7-yloxy]methyl}benzenecarbonitrile and following the procedure of 6A above, 3-(4-hydroxyphenyl)-7-[(3-(1H-1,2,3,4-tetrazol-5-yl)phenyl)methoxy]chromen-4-one was prepared.

$^1$H NMR (400 MHz, DMSO-d$_6$) δ: 9.56 (s, 1H), 8.39 (s, 1H), 8.21 (s, 1H), 8.06 (m, 2H), 7.73-7.67 (m, 2H), 7.40 (d, 2H, J=8.4 Hz), 7.31-6.81 (m, 5H), 5.42 (s, 2H). (ESI) m/z 435 (M+Na)$^+$, (ES−) m/z 411.1 (M−1)

C. Preparation of a Compound of Formula I in which $R^1$ is (3-(1H-1,2,3,4-Tetrazol-5-yl)phenyl)

Similarly, starting with other compounds of Formula I in which $R^1$ is phenyl substituted by cyano, and following the procedure of 6A above, other compounds of Formula I in which $R^1$ is 3-(1H-1,2,3,4-tetrazol-5-yl)phenyl are prepared.

EXAMPLE 7

Preparation of a Compound of Formula I

A. Preparation of a Compound of Formula I in which $R^1$ is Prop-2-enyl 3-benzoate and $R^2$ is Amino

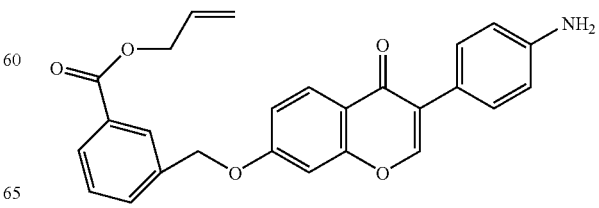

A suspension of 3-[3-(4-nitrophenyl)-4-oxo-4H-chromen-7-yloxymethyl]benzoic acid allyl ester (164.6 mg, 0.36 mmol), prepared as described in Example 5d, and sodium dithionite (188 mg, 1.08 mmol) in tetrahydrofuran (8 ml) and water (4 ml) was heated at 60-65° C. for 1 hour. Additional sodium dithionite (1.13 g, 6.48 mmol) was added in 5 portions over 2 hours. The reaction mixture was stirred at 60-65° C. overnight. $^1$H NMR of the reaction mixture showed that the product was obtained without starting material. The reaction mixture was mixed with silica gel (2 g), solvent removed under reduced pressure, and the mixture applied to a column. The silica gel mixture was purified by flash chromatography, eluting with methylene chloride/methanol (98/2) to give prop-2-enyl 3-{[3-(4-aminophenyl)-4-oxochromen-7-yloxy]methyl}benzoate as a yellow solid (99.6 mg, 65%); (ESI) m/z 428 (M+H)$^+$.

B. Alternative Preparation of a Compound of Formula I in which R$^1$ is 3-(tert-butoxycarbonyl)phenylmethyl and R$^2$ is Amino In a 3 L 3-neck round bottomed flask the starting material (58.00 g, 122.50 mmol, tert-butyl 3-((3-(4-nitrophenyl)-4-oxo-4H-chromen-7-yloxy)methyl)benzoate, 99.8% purity) was suspended in AcOH (348 mL, Aldrich). To the suspension was added Zn (40.04 g, 612.50 mmol, 5.0 equiv., Aldrich) over 30 min. The suspension was cooled with ice-water bath so that the internal temperature may be maintained between 20-35° C. since the reaction is extremely exo-thermic. After the addition of Zn, the ice-water bath was removed and the reaction vessel was allowed to warm to room temperature (22° C.). After 30 min stirring an HPLC analysis indicated formation of the desired product, 99.25%. The reaction mixture was stirred at the same temperature for 1 hour.

To the reaction mixture was added EtOAc (1800 mL, J. T. Baker) at ambient temperature and the mixture was stirred for 20 min. The mixture was then filtered through a glass filter (350 mL with a fine lid) with Celite (30 g, Aldrich) to remove the side product, ZnOAc. The resulting yellow residue which formed on the Celite was washed with EtOAc (250 mL) on the glass filter to give a yellow filtrate (Filtrate 1, ca. 2100 mL). Only the yellow residue on the Celite was removed and was suspended in EtOAc (1500 mL). The suspension was stirred for 40 min. Using the Celite and the glass filter used above, the suspension was filtered. The resulting yellow residue on the Celite was washed with EtOAc (250 mL) on the glass filter to give a very light yellow filtrate (Filtrate 2, ca. 1800 mL).

Filtrate 1 and Filtrate 2 were combined (ca. 3900 mL) and divided into three portions (ca. 1300 mL). Each portion was washed with brine (10% NaCl/H$_2$O, 800 mL) in a 2 L separatory funnel and dried with Na$_2$SO$_4$ (80 g, Aldrich) in a 2 L Erlen-Myer Flask (×3) for 1 hour. After removal of Na$_2$SO$_4$ by filteration through a piece of cotton, the solvent was removed under a reduced pressure at 50° C. A residual amount of the solvent was removed by high-vacuum at 22° C. for 6 h to give the desired product as a yellow solid (61.08 g, contaminated with ~100 mol % of AcOH). Similar reactions with similar scale were repeated another three times to consume the starting material and provide the final product, tert-butyl 3-((3-(4-aminophenyl)-4-oxo-4H-chromen-7-yloxy)methyl)benzoate.

C. Preparation of a Compound of Formula I, Varying R$^1$

Similarly, replacing 3-[3-(4-nitrophenyl)-4-oxochromen-7-yloxymethyl]benzoic acid allyl ester with other compounds of formula (3), and following the procedure of 7A or 7B above, the following compounds of formula (4) were prepared:

3-(4-aminophenyl)-7-({5-[3-(trifluoromethyl)phenyl](1,2,4-oxadiazol-3-yl)}methoxy)chromen-4-one; $^1$H NMR (400 MHz, DMSO-d$_6$) δ: 8.46 (d, 1H, J=7.9 Hz) 8.39 (s, 1H), 8.35 (s, 1H), 8.13 (d, 1H, J=7.6 Hz), 8.07 (d, 1H, J=8.9 Hz), 7.92 (dd, 1H, J=7.9 Hz, J=7.9 Hz), 7.37 (d, 1H, J=1.8 Hz), 7.27 (d, 2H, J=8.3 Hz), 7.21 (dd, 1H, J=1.8 Hz, J=8.9 Hz), 6.61 (d, 2H, J=8.3 Hz), 5.60 (s, 2H), 5.23 (s, 2H); (ESI) m/z 480 (M+H)$^+$.

methyl 3-{[3-(4-aminophenyl)-4-oxochromen-7-yloxy]methyl}benzoate; (ESI) m/z 402 (M+H)$^+$ 7-({5-[5-fluoro-3-(trifluoromethyl)phenyl](1,2,4-oxadiazol-3-yl)}methoxy)-3-(4-aminophenyl)chromen-4-one); (ESI) m/z 498.2 (M+H)$^+$.

3-{[3-(4-aminophenyl)-4-oxochromen-7-yloxy]methyl}benzenecarbonitrile; (ESI) m/z 369 (M+H)$^+$.

3-{[3-(4-aminophenyl)-4-oxochromen-7-yloxy]methyl}benzamide; (ESI) m/z 387 (M+H)$^+$.

C. Preparation of a Compound of Formula I, Varying R$^1$

Similarly, replacing 3-[3-(4-nitrophenyl)-4-oxo-4H-chromen-7-yloxymethyl]benzoic acid allyl ester with other compounds of formula (3), and following the procedure of 7A or 7B above, other compounds of Formula I are prepared.

EXAMPLE 8

Preparation of a Compound of Formula I

A. Preparation of a Compound of Formula I in which R$^1$ is 3-(Prop-2-enyl)benzoate, R$^2$ is 4-[(Methylsulfonyl)amino, R$^3$ is Hydrogen, X, Y and Z are —CH—, V is Oxygen, and W is Methylene

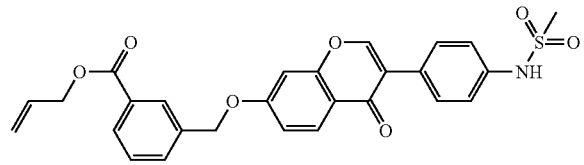

To a mixture of prop-2-enyl 3-{[3-(4-aminophenyl)-4-oxochromen-7-yloxy]methyl}benzoate, prepared as described in Example 7A, (169.5 mg, 0.397 mmol) and anhydrous pyridine (34.5 mg, 0.44 mmol) in dry methylene chloride (3 ml) at 0° C. was added methanesulfonyl chloride (68.1 mg, 0.60 mmol). The mixture was then stirred at room temperature for 21 hours, then mixed with silics gel and the solvent removed under reduced pressure. Flash chromatography of the silica gel mixture, eluting with methylene chloride/methanol (99.5/0.5) gave prop-2-enyl 3-[(3-{4-[(methylsulfonyl)amino]phenyl}-4-oxochromen-7-yloxy)methyl]benzoate as a white solid (160.9 mg). (ESI) m/z 506 (M+H)$^+$.

B. Alternative Preparation of a Compound of Formula I in which R$^1$ is 3-(tert-butoxycarbonyl)phenyl, R$^2$ is 4-[(Methylsulfonyl)amino, R$^3$ is Hydrogen, X, Y and Z are —CH—, V is Oxygen, and W is Methylene In a 3 L 3-neck round bottomed flask, tert-butyl 3-((3-(4-aminophenyl)-4-oxo-4H-chromen-7-yloxy)methyl)benzoate as prepared in Example 7B (474.05 mmol) was dissolved in pyridine (1053 mL, Aldrich) to give an orange solution. To the solution was added MeSO$_2$Cl (81.45 g, 711.08 mmol, 1.5 equiv., Aldrich) over 10 min. The reaction mixture was cooled with ice-water bath so that the internal temperature may be maintained between 20-35° C. since the reaction is slightly exothermic. After the addition of MeSO$_2$Cl, the ice-water bath was removed and the reaction vessel was allowed to warm to ambient temperature (22° C.).

After stirring for 1 hour, an HPLC analysis showed the desired product and the starting material, 98.55% and 0.30% respectively. After 1.5 hours stirring to resulting orange suspension was slowly added H₂O (1900 mL, distilled at CVT). The suspension was divided into three portions (into three 3 L round bottomed flasks). To the each flask was added H₂O (1185 mL, distilled at CVT) individually (Total amount of H₂O added: 5455 mL, 11.5 mL/mmol). The mixtures were stirred at least 30 min at ambient temperature (22° C.) and filtered through a 2 L filtration funnel (coarse) to collect the crude product. The crude product on the funnel was transferred into a 4 L Erlen-Myer Flask and suspended in H₂O (2800 mL). After stirring for 20 min the suspension was filtered through a 2 L filtration funnel (coarse) to collect the crude product. Suspending in H₂O (2800 mL) in a 4 L flask and filtration was repeated once again. The residue on the filtration funnel was placed in drying dishes (ca 500 mL volume) (1162 g at this point).

The wet crude product was dried under high-vacuum at 60° C. for 54 hours to give dried crude product as a light yellow chunky powder. This was placed in another 3 L 3-neck round bottomed flask and suspended in DMF (3 mL/g, 729 mL, Aldrich). The suspension was heated using heating mantles so that the internal temperature may reach to 90° C. The suspension was cooled with water-bath for 10 min. When the internal temperature became 40° C., MeOH (1000 mL, Aldrich) was added. The suspension was divided into 2 flasks (3 L 3-neck round bottomed flask). To the each flask was added MeOH (1322 mL). (Total amount of MeOH added: 3644 mL, 15 mL/g) After stirring at least for 1 hour at ambient temperature, the suspensions were filtered through a 2 L filtration funnel (medium). The product on the filter was washed with MeOH (Total 1200 mL). The residue on the filtration funnel was placed in drying dishes (ca 500 mL volume) (202.32 g at this point). The wet product was dried under high-vacuum at 60° C. for 4 hours to give tert-butyl 3-((3-(4-(methylsulfonamido)phenyl)-4-oxo-4H-chromen-7-yloxy)methyl)benzoate as a light yellow powder.

C. Preparation of Compounds of Formula I in which R² is 4-[(Methylsulfonyl)amino, R³ is Hydrogen, X, Y and Z are —CH—, V is Oxygen, and W is Methylene, Varying R¹

Similarly, replacing prop-2-enyl 3-{[3-(4-aminophenyl)-4-oxochromen-7-yloxy]methyl}benzoate with other compounds of formula (4), and following the procedure of 8A or 8B above, the following compounds of Formula I in which R² is 4-[(methylsulfonyl)amino were prepared:

methyl 3-[(3-{4-[(methylsulfonyl)amino]phenyl}-4-oxo-chromen-7-yloxy)methyl]benzoate; ¹H NMR (400 MHz, DMSO-d₆) δ: 9.84 (br s, 1H), 8.46 (s, 1H), 8.10 (s, 1H), 8.07 (d, 1H, J=8.9 Hz), 7.96 (d, 1H, J=7.8 Hz), 7.80 (d, 1H, J=7.7 Hz), 7.62-7.56 (m, 3H), 7.30 (s, 1H), 7.27 (d, 2H, J=8.1 Hz), 7.20 (dd, 1H, J=1.5 Hz, J=9.0 Hz), 5.39 (s, 2H), 3.03 (s, 3H). (ESI) m/z 480 (M+H)⁺.

3-{4-[(methylsulfonyl)amino]phenyl}-7-({5-[3-(trifluoromethyl)phenyl](1,2,4-oxadiazol-3-yl)}methoxy)chromen-4-one; ¹H NMR (300 MHz, DMSO-d₆) δ: 9.86 (s, 1H), 8.49 (s, 1H), 8.45 (d, 1H, J=7.8 Hz), 8.38 (s, 1H), 8.12 (d, 1H, J=8.1 Hz), 8.08 (d, 1H, J=9.0 Hz), 7.91 (dd, 1H, J=7.9 Hz, J=7.9 Hz), 7.57 (d, 2H, J=8.6 Hz), 7.41 (d, 1H, J=2.3 Hz), 7.28-7.21 (m, 3H), 5.61 (s, 2H), 3.03 (s, 3H). (ESI) m/z 558 (M+H)⁺.

7-({5-[5-fluoro-3-(trifluoromethyl)phenyl](1,2,4-oxadiazol-3-yl)}methoxy)-3-{4-[(methylsulfonyl)amino]phenyl}chromen-4-one; ¹H NMR (300 MHz, DMSO-d₆) δ: 9.85 (s, 1H), 8.49 (s, 1H), 8.33-8.08 (m, 4H), 7.56 (d, 2H, J=8.7 Hz), 7.42-7.22 (m, 4H), 5.62 (s, 2H), 3.02 (s, 3H). (ESI) m/z 576.1 (M+H)⁺.

3-[(3-{4-[(methylsulfonyl)amino]phenyl}-4-oxo-chromen-7-yloxy)methyl]-benzenecarbonitrile; ¹H NMR (400 MHz, DMSO-d₆) δ: 9.84 (s, 1H), 8.47 (s, 1H), 8.07 (d, 1H, J=9.2 Hz), 8.00 (s, 1H), 7.86 (d, 2H, J=7.6 Hz), 7.66 (dd, 1H, J=7.6, 7.6 Hz), 7.57 (d, 2H, J=8.8 Hz), 7.31-7.20 (m, 4H), 5.36 (s, 2H), 3.03 (s, 3H). (ESI) m/z 447 (M+H)⁺.

3-{[3-(4-methylsulfonylaminophenyl)-4-oxochromen-7-yloxy]methyl}benzamide; ¹H NMR (400 MHz, DMSO-d₆) δ: 9.83 (s, 1H), 8.46 (s, 1H), 8.06 (d, 1H, J=8.9 Hz), 8.01 (s, 2H), 7.87 (d, 1H, J=7.5 Hz), 7.65 (d, 1H, J=7.9 Hz), 7.57 (d, 2H, J=8.6 Hz), 7.50 (dd, 1H, J=7.7, 7.7 Hz), 7.40 (br s, 1H), 7.30 (d, 1H, J=2.2 Hz), 7.26 (d, 2H, J=8.6 Hz), 7.19 (dd, 1H, J=2.2, 8.9 Hz), 5.33 (s, 2H), 3.02 (s, 3H). (ESI) m/z 465 (M+H)⁺.

EXAMPLE 9

Preparation of a Compound of Formula I

A. Preparation of a Compound of Formula I in which R¹ is 3-Benzoic Acid, R² is 4-[(Methylsulfonyl)amino, R³ is Hydrogen, X, Y and Z are —CH—, V is Oxygen, and W is Methylene

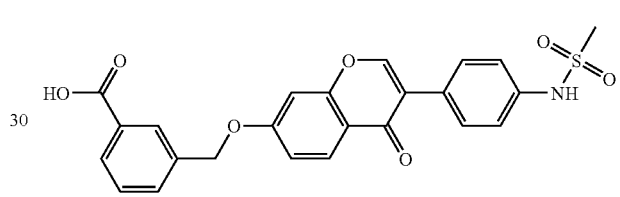

To a solution of prop-2-enyl 3-[(3-{4-[(methylsulfonyl)amino]phenyl}-4-oxochromen-7-yloxy)methyl]benzoate (88.8 mg, 0.176 mmol), tetrakis(triphenyl-phosphine)palladium(0) (10 mg, 0.009 mmol) in dry tetrahydrofuran 2 ml) was added morpholine (77 mg, 0.88 mmol), and the mixture was stirred at room temperature under argon for 2 hours. Solvent was then removed reduced pressure, and the residue dissolved in acetone, mixed with silica gel, the solvent removed under reduced pressure, and the silica gel eluted with methylene chloride/methanol (95/5) containing 1% acetic acid, to provide 3-[(3-{4-[(methylsulfonyl)phenyl}-4-oxochromen-7-yloxy)methyl]benzoic acid; ¹H NMR (400 MHz, DMSO-d₆) δ: 13.1 (br s, 1H), 9.84 (s, 1H), 8.47 (s, 1H), 8.08-8.06 (m, 2H), 7.94 (d, 1H, J=7.8 Hz), 7.76 (d, 1H, J=7.7 Hz), 7.58-7.45 (m, 3H), 7.30 (d, 1H, J=1.8 Hz), 7.27 (d, 2H, J=8.5 Hz), 7.20 (dd, 1H, J=1.8 Hz, J=8.9 Hz), 5.38 (s, 2H), 3.03 (s, 3H). (ESI) m/z 466 (M+H)⁺.

B. Alternate Preparation of a Compound of Formula I in which R¹ is 3-Benzoic Acid, R² is 4-[(Methylsulfonyl)amino, R³ is Hydrogen, X, Y and Z are —CH—, V is Oxygen, and W is Methylene In a 3 L 3-neck round bottomed flask tert-butyl 3-((3-(4-(methylsulfonamido)phenyl)-4-oxo-4H-chromen-7-yloxy)methyl)benzoate (157.88 g, 302.70 mmol,) was suspended in HCO₂H (1026 mL, 6.5 mL/g, Aldrich). The mixture was heated at 50° C. (internal temperature) for 1 h using a heating mantle. An HPLC analysis showed the desired product and the starting material, 98.61% and 1.39% respectively. The internal temperature was increased to 80° C. taking for approximately 30 min. After heating at 80° C. for 2 hours an HPLC analysis showed the desired product and the starting material, 99.82% and 0.18% respectively. The heating mantle was turned off and the suspension was allowed to cool down to ambient temperature and stirred for 8 hours (the desired product, 99.86% and the starting material, 0.14%).

After stirring for 8 hours to the reaction mixture was added H₂O (1104 mL, distilled at CVT) at the room temperature (22° C.). The mixture was divided into two portions (into 3 L 3-necked flask×2). To the each flask was added H₂O (1500 mL). Total amount of water added was 4104 mL at this point. The suspensions were stirred at least for 1 hour under ice-water bath cooling. The suspensions were filtered through a 2 L filtration funnel (medium). The residue was washed with H₂O (total 1000 mL) on the filter. Obtained residue was put into a 4 L Erlen-Myer Flask and suspended in H₂O (3000 mL). The mixture was stirred for 20 min and filtered through the 2 L filtration funnel (medium). The residue was washed with H₂O (500 mL) on the filter. Suspending in H₂O (3000 mL) in a 4 L flask and filtration was repeated once again. Obtained wet material was 197.06 g (very light brown wet powder). This was placed in two drying dishes and dried under high-vacuum at 60° C. for 18 hours to provide 3-[(3-{4-[(methylsulfonyl)amino]phenyl}-4-oxochromen-7-yloxy)methyl]benzoic acid.

C. Recrystallization of a Compound of Formula I in which R¹ is 3-Benzoic Acid, R² is 4-[(Methylsulfonyl)amino, R³ is Hydrogen, X, Y and Z are —CH—, V is Oxygen, and W is Methylene 3-[(3-{4-[(methylsulfonyl)amino]phenyl}-4-oxo-chromen-7-yloxy)methyl]benzoic acid from Example 9B was recrystallized from DMF (554 mL, 4 mL/g)-MeOH (4424 mL, 32 mL/g) as follows. The crude product was divided into two portions (69.25 g each, into 3 L 3-necked flask×2). To the each flask was added DMF (277 mL, Aldrich) to dissolve the crude product (light brown solution) at ambient temperature (22° C.). To the each solution was added MeOH (2216 mL) over 10 min. An addition of MeOH makes the solutions suspensions (creamy colored). After stirring for 1 h the both suspensions were filtered through a 2 L glass filter (medium). The residue on the filter was washed with MeOH (total 1108 mL). The residue on the filter (very very light orange wet powder, 465.79 g) was transferred to drying dishes and dried under high-vacuum at 60° C. for 12 h to remove MeOH. After drying for 12 h a very light yellow powder (130.56 g, contaminated with DMF 12-14%) was obtained. This contaminated product was again dried under high-vacuum at 175° C. for 20 h to remove DMF completely. The end product was obtained as a very light yellow powder without any DMF contamination.

D. Preparation of a Compound of Formula I in which R¹ is 3-Benzoic Acid, R³ is Hydrogen, X, Y and Z are —CH—, V is Oxygen, and W is Methylene Varying R²

Similarly, replacing prop-2-enyl 3-[(3-{4-[(methylsulfonyl)amino]phenyl}-4-oxochromen-7-yloxy)methyl]benzoate with other compounds of Formula I in which R¹ is prop-2-enylbenzoate, and following the procedure of 9A or 9B above, the following compounds of Formula I in which R¹ is benzoic acid were prepared:

3-{[3-(4-hydroxyphenyl)-4-oxochromen-7-yloxy]methyl}benzoic acid; ¹H NMR (400 MHz, DMSO-d₆) δ: 13.1 (br s, 1H), 9.59 (br s, 1H), 8.38 (s, 1H), 8.08 (s, 1H), 8.05 (d, 1H, J=9.0 Hz), 7.94 (d, 1H, J=7.8 Hz), 7.75 (d, 1H, J=7.7 Hz), 7.56 (dd, 1H, J=7.5 Hz, J=7.8 Hz), 7.40 (d, 2H, J=8.7 Hz), 7.29 (d, 1H, J=1.9 Hz), 7.18 (dd, 1H, J=1.9 Hz, J=9.0 Hz), 6.82 (d, 2H, J=8.7 Hz), 5.37 (s, 2H). (ESI) m/z 389 (M+H)⁺.

3-(3-{[3-(4-hydroxyphenyl)-4-oxochromen-7-yloxy]methyl}-1,2,4-oxadiazol-5-yl)benzoic acid; ¹H NMR (400 MHz, DMSO-d₆) δ 13.5 (s, 1H), 9.54 (br s, 1H), 8.62 (s, 1H), 8.40 (s, 1H), 8.36 (d, 1H, J=7.7 Hz), 8.25 (d, 1H, J=7.8 Hz), 8.08 (d, 1H, J=8.9 Hz), 7.79 (dd, 1H, J=7.8 Hz, J=7.8 Hz), 7.42-7.40 (m, 3H), 7.23 (dd, 10H, J=1.6 Hz, J=9.0 Hz), 6.82 (d, 2H, J=8.4 Hz), 5.59 (s, 2H). (ESI) m/z 457 (M+H)⁺.

3-{[3-(4-aminophenyl)-4-oxochromen-7-yloxy]methyl}benzoic acid; (ESI) m/z 388 (M+H)⁺.

EXAMPLE 10

Preparation of a Compound of Formula I

A. Preparation of a Compound of Formula I in which R¹ is 3-((2-morpholinoethoxy)carbonyl)benzyl, R² is 4-[(Methylsulfonyl)amino, R³ is Hydrogen, X, Y and Z are —CH—, V is Oxygen, and W is Methylene

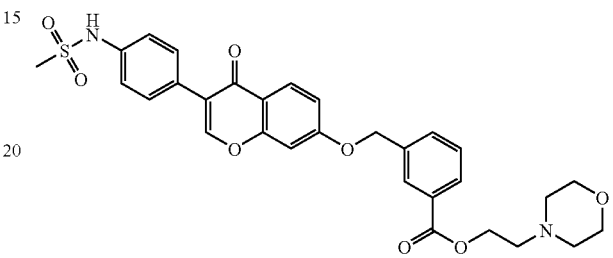

In a 100 mL round bottomed flask 3-[(3-{4-[(methylsulfonyl)amino]phenyl}-4-oxochromen-7-yloxy)methyl]benzoic acid (315.0 mg, 0.677 mmol) was treated with triethylamine (137.0 mg, 1.354 mmol, 2.0 equiv) and 2,4,6-trichlorobenzoyl chloride (198.2 mg, 0.812 mmol, 1.2 equiv) in THF (6 mL) under a nitrogen atmosphere. The mixture was stirred at room temperature for 1 hour. To the mixture were added a solution of 4-hydroxyethyl)morpholine (133.2 mg, 1.016 mmol, 1.5 equiv) in THF (3 mL) and dimethylaminopyridine (82.7 mg, 0.677 mmol, 1.0 equiv). Again, the mixture was stirred at room temperature for 1 hour. To the mixture were added H₂O (50 mL) and the whole was extracted with EtOAc (50 mL×3). The combined organic layers were washed with brine (50 mL) and dried with Na₂SO₄. The solvent was removed under a reduced pressure to give a crude mixture. The crude mixture was purified by a column-chromatography (SiO₂=80 g, 2.5% MeOH/CH₂Cl₂ to 5% MeOH/CH₂Cl₂) to give 2-morpholinoethyl 3-((3-(4-(methylsulfonamido)phenyl)-4-oxo-4H-chromen-7-yloxy)methyl)benzoate as a colorless solid.

B. Preparation of a Compound of Formula I in which R² is 4-[(Methylsulfonyl)amino, R³ is Hydrogen, X, Y and Z are —CH—, V is Oxygen, and W is Methylene Varying R¹

Similarly, replacing 4-hydroxyethyl)morpholine with 1-(2-hydroxyethyl)-4-methylpiperazine and following the procedure of 10A above, 2-(4-methylpiperazine)ethyl 3-((3-(4-(methylsulfonamido)phenyl)-4-oxo-4H-chromen-7-yloxy)methyl)benzoate was prepared.

C. Preparation of a Compound of Formula I in which R² is 4-[(Methylsulfonyl)amino, R³ is Hydrogen, X, Y and Z are —CH—, V is Oxygen, and W is Methylene Varying R¹

Similarly, replacing 4-hydroxyethyl)morpholine with other compounds of the formula R²⁰OH and following the procedure of 10A above, other compounds of Formula I are prepared.

EXAMPLE 11

Preparation of a Compound of Formula I

A. Preparation of a Compound of Formula I in which R¹ is 3-Methylbenzoate, R² is 4-[(Methylamino)carbonylamino, R³ is Hydrogen, X, Y and Z are —CH—, V is Oxygen, and W is Methylene

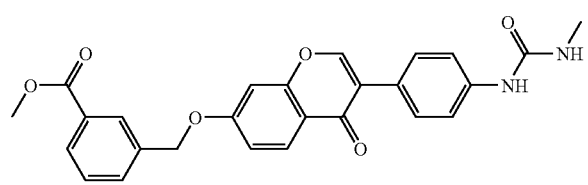

A suspension of methyl 3-{[3-(4-aminophenyl)-4-oxo-chromen-7-yloxy]methyl}benzoate (100 mg, 0.25 mmol) and methyl isocyanate (57 mg) in tetrahydrofuran (1 ml) was placed in a sealed tube, and the mixture stirred at room temperature for 3 days. The reaction mixture was slurried with methylene chloride, and solvent removed under reduced pressure, to provide crude methyl 3-[(3-{4-[(methylamino)carbonylamino]phenyl}-4-oxochromen-7-yloxy)methyl]benzoate. The solid was dissolved in a mixture of methanol/methylene chloride, mixed with silica gel, solvent removed, and the silica gel eluted with methanol/methylene chloride (3/97) to provide 90 mg of pure product. (ESI) m/z 459 $(M+H)^+$.

B. Preparation of a Compound of Formula I in which $R^1$ is 3-Methylbenzoate, $R^2$ is 4-acetylamino, $R^3$ is Hydrogen, X, Y and Z are —CH—, V is Oxygen, and W is Methylene Similarly, replacing methyl isocyanate by acetyl chloride, and following the procedure of 11A above, methyl 3-({3-[4-(acetylamino)phenyl]-4-oxochromen-7-yloxy}methyl)benzoate was prepared.

EXAMPLE 12

Preparation of a Compound of Formula I

A. Preparation of a Compound of Formula I in which $R^1$ is 2-[4-(4-methoxyphenyl)piperazinyl], $R^2$ is 4-Hydroxy, $R^3$ is Hydrogen, X, Y and Z are —CH—, V is Oxygen, and W is Ethylene

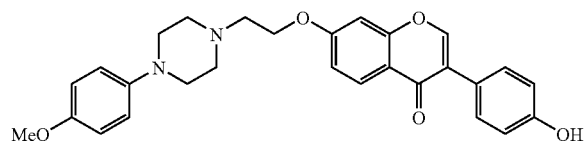

Step 1

1-(4-methoxyphenyl)piperazine was dissolved in N,N-dimethylformamide, and potassium carbonate and 1-bromo-2-chloroethane were added. The resulting mixture was stirred at room temperature overnight, the solid material filtered off, and the solvent removed from the filtrate under reduced pressure. The residue was purified by biotage chromatography eluting with 3:7 ethyl acetate:hexanes, to provide 1-[4-(2-chloroethyl)piperazinyl]-4-methoxybenzene.

Step 2

To a solution of 1-[4-(2-chloroethyl)piperazinyl]-4-methoxybenzene (0.929 mmol) and 4,7-dihydroxyisoflavone (0,929 mmol) in acetone (10 ml) was added 11% potassium hydroxide (0.5 ml), and the mixture stirred at reflux temperature for 48 hours. Sufficient methanol was added to precipitate unreacted starting material, which was filtered off, and solvent was removed from the filtrate under reduced pressure. The residue was purified by biotage column chromatography, eluting with 5% methanol/methylene chloride, to provide pure 3-(4-hydroxyphenyl)-7-{2-[4-(4-methoxyphenyl)piperazinyl]ethoxy}chromen-4-one.

B.

Similarly, the following piperazinyl derivatives were prepared:

7-{2-[4-(4-fluorophenyl)piperazinyl]ethoxy}-3-(4-hydroxyphenyl)chromen-4-one;
3-(4-hydroxyphenyl)-7-(2-piperazinylethoxy)chromen-4-one;
N-(3-fluorophenyl)(4-{2-[3-(4-hydroxyphenyl)-4-oxo-chromen-7-yloxy]ethyl}-piperazinyl)carboxamide;
7-[2-(4-{[(3-fluorophenyl)amino]thioxomethyl}piperazinyl)ethoxy]-3-(4-hydroxyphenyl)chromen-4-one;
N-(2,4-difluorophenyl)(4-{2-[3-(4-hydroxyphenyl)-4-oxo-chromen-7-yloxy]ethyl}piperazinyl)carboxamide;

EXAMPLE 13

Preparation of a Compound of Formula I

A. Preparation of a Compound of Formula I in which $R^1$ is 2-[3-fluoro-5-(trifluoromethyl)phenyl]-1,3-oxazole], $R^2$ is 4-Hydroxy, $R^3$ is Hydrogen, X, Y and Z are —CH—, V is Oxygen, and W is Ethylene

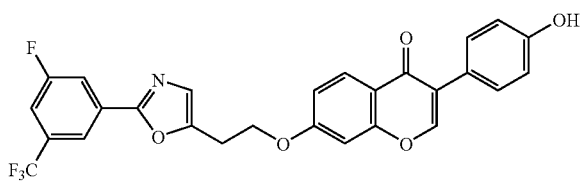

Step 1

In a 50 mL round bottomed flask was placed diethyl malonate (3.72 g, 23.25 mmol, 5 equiv.) and N,N-dimethylformamide (10 mL). To the solution was added sodium hydride (60% suspension in mineral oil, 744.0 mg, 18.6 mmol, 4.0 equiv.) at room temperature portionwise over 10 minutes. After stirring for 30 minutes a solution of 4-(chloromethyl)-2-[5-fluoro-3-(trifluoromethyl)phenyl]-1,3-oxazole (1.30 g, 4.65 mmol) in N,N-dimethylformamide (10 mL) was added at 0° C. over 15 minutes, and the reaction mixture allowed to warm up to ambient temperature. To the mixture was added sodium iodide (697.0 mg, 4.65 mmol, 1 equiv) at room temperature. The reaction mixture was stirred at the same temperature for 2 hours. Water was then added to the reaction mixture (30 mL) and the whole was extracted with ethyl acetate (30 mL×3). The organic layers were combined, washed with brine (30 mL) and dried with sodium sulfate. After removal of the solvent under reduced pressure the crude mixture was purified by a silica-gel column chromatography (SiO₂=80 g, hexane:EtOAc=7:1) repeatedly. The desired product, diethyl 2-({2-[5-fluoro-3-(trifluoromethyl)phenyl]-1,3-oxazol-4-yl}methyl)propane-1,3-dioate, was obtained as colorless powder (1.75 g).

Step 2

The product of Step 1 was used without further purification. The product (606.7 mg, 1.50 mmol) was placed in a 50 mL round bottomed flask, and lithium chloride (127.6 mmol, 3.01 mmol, 2 equiv.), dimethylsulfoxide (5 mL) and water (0.5 mL) added, and the mixture heated at 190-195° C. for 3 hours. To the reaction mixture was added water (30 mL) and the whole was extracted with ethyl acetate (30 mL×3). The combined organic layers were washed with brine (30 mL) and dried over sodium sulfate. After removal of the solvent under reduced pressure the crude mixture was purified by a silica-gel column chromatography (SiO$_2$=80 g, hexane:EtOAc=3:1). The desired product, ethyl 3-{2-[5-fluoro-3-(trifluoromethyl)phenyl]-1,3-oxazol-4-yl}propanoate, was obtained as light yellow oil (345.5 mg).

Step 3

The product of Step 2 (330.0 mg, 0.996 mmol) was placed in a 250 mL round bottomed flask and dissolved in tetrahydrofuran (3 mL). The solution was treated with lithium aluminum hydride at 0° C. under nitrogen atmosphere. After stirring for 30 minutes, Celite (3 g) was added to the reaction mixture, followed by methanol (5 mL) and water (3 mL) successively. The resulting suspension was filtered through a glass filter, and the residue on the filter washed with ethyl acetate (50 mL). The solvent was removed under reduced pressure to give a colorless oil (298.3 mg). The crude mixture was purified by a silica-gel column chromatography (SiO$_2$=80 g, hexane:EtOAc=7:1) to give 3-{2-[5-fluoro-3-(trifluoromethyl)phenyl]-1,3-oxazol-4-yl}propan-1-ol as a colorless oil (255.3 mg, 0.883 mmol, 89%).

Step 4

To 3-{2-[5-fluoro-3-(trifluoromethyl)phenyl]-1,3-oxazol-4-yl}propan-1-ol (250.3 mg, 0.865 mmol) was added a mixture of triphenyl phosphate (295.4 mg, 0.952 mmol, 1.1 equiv.) and methyl iodide (184.2 mg, 1.298 mmol, 1.5 equiv.). The mixture was heated at 130° C., while adding a further amount of methyl iodide (184.2 mg, 1.298 mmol, 1.5 equiv.). The reaction mixture was heated for a total of 2 hours, and then purified by column-chromatography (SiO$_2$=25 g, hexane/EtOAc=7:1) followed by preparative TLC (SiO$_2$=6 plates, hexane/EtOAc=15:1) to give 2-[5-fluoro-3-(trifluoromethyl)phenyl]-4-(3-iodopropyl)-1,3-oxazole (116.1 mg, 0.291 mmol, 34%) as a colorless oil.

Step 5

4',7-Dihydroxyisoflavone (31.3 mg, 0.123 mmol), 2-[5-fluoro-3-(trifluoromethyl)phenyl]-4-(3-iodopropyl)-1,3-oxazole (48.9 mg, 0.123 mmol, 1.0 equiv.) and cesium carbonate (40.0 mg, 0.123 mmol, 1.0 equiv) were placed in a 25 mL flask. To the flask was added dimethylsulfoxide (3 mL) at room temperature to dissolve the starting materials, and the reaction mixture stirred room temperature for 15 hours. To the mixture were added water (30 mL) and the whole was extracted with ethyl acetate (30 mL×3). The combined organic layers were washed with brine (30 mL) and dried with sodium sulfate to give a crude mixture as colorless oil (64.2 mg). The crude mixture was purified by column-chromatography (SiO$_2$=80 g, hexane/EtOAc=2:1 to 1:1) to give 7-(2-{2-[3-fluoro-5-(trifluoromethyl)phenyl](1,3-oxazol-5-yl)}ethoxy)-3-(4-hydroxyphenyl)chromen-4-one (49.1 mg, 0.0934 mmol, 76%) as colorless crystals. Similarly prepared was 7-(3-{2-[3-fluoro-5-(trifluoromethyl)phenyl](1,3-oxazol-4-yl)}propoxy)-3-(4-hydroxyphenyl)chromen-4-one.

EXAMPLE 14

Preparation of a Compound of Formula I

A. Preparation of a Compound of Formula I in which R$^1$ is 4-Fluorophenyl, R$^2$ is 4-Hydroxy, R$^3$ is Hydrogen, X, Y and Z are —CH—, V is Oxygen, and W is —C(O)CH$_2$—

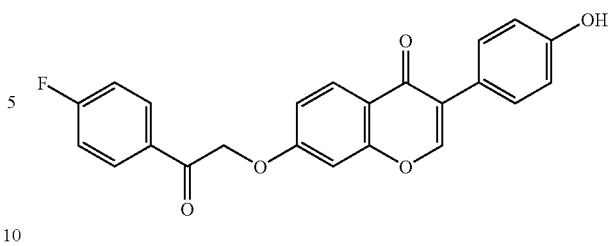

Dihydroxyisoflavone (0.2 g, 0.78 mmol) was suspended in acetone (10 ml), and to this suspension was added 2-bromo-1-(4-fluorophenyl)ethane-1-one (0.16 g, 0.75 μmmol) and 11% potassium hydroxide (0.78 mmol). The mixture was refluxed for 24 hours, and the solvent removed under reduced pressure. The residue was treated with water, sonicated, filtered, and air-dried. The solid was triturated with methanol, filtered, to afford 7-[2-(4-fluorophenyl)-2-oxoethoxy]-3-(4-hydroxyphenyl)chromen-4-one. If desired, the product may be further purified by preparative thin layer chromatography, eluting with dichloromethane/methanol 15/1.

B.

Similarly, following the procedures of Example 14A above, replacing 2-bromo-1-(4-fluorophenyl)ethane-1-one with other haloacetophone derivatives, the following compounds were prepared:

7-[2-(3-fluorophenyl)-2-oxoethoxy]-3-(4-hydroxyphenyl)chromen-4-one;

3-(4-hydroxyphenyl)-7-{2-oxo-2-[2-(trifluoromethyl)phenyl]ethoxy}chromen-4-one;

3-(4-hydroxyphenyl)-7-{2-oxo-2-[2-(trifluoromethyl)phenyl]ethoxy}chromen-4-one.

EXAMPLE 15

Preparation of a Compound of Formula I

A. Preparation of a Compound of Formula I in which R$^1$ is 3-Trifluoromethylphenyl, R$^2$ is 4-Hydroxy, R$^3$ is Hydrogen, X, Y and Z are —CH—, V is Oxygen, and W is —NHC(O)CH$_2$—

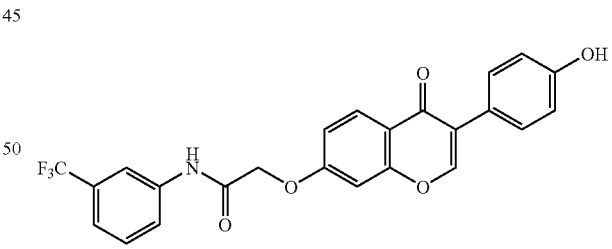

Dihydroxyisoflavone (0.2 g, 0.78 mmol) was suspended in acetone (10 ml), and to this suspension was added 2-chloro-N-[3-(trifluoromethyl)phenyl]acetamide (0.18 g, 0.78 mmol) and 11% potassium hydroxide (0.78 mmol). The mixture was refluxed for 24 hours, and the solvent removed under reduced pressure. The residue was treated with water, sonicated, filtered, and air-dried. The solid was triturated with methanol, filtered, to afford 2-[3-(4-hydroxyphenyl)-4-oxochromen-7-yloxy]-N-[3-(trifluoromethyl)phenyl]acetamide. If desired, the product may be further purified by preparative thin layer chromatography, eluting with dichloromethane/methanol 15/1.

B.

Similarly, following the procedures of Example 15A above, replacing 2-chloro-N-[3-(trifluoromethyl)phenyl]acetamide with other haloacetamide derivatives, the following compounds were prepared:

N-[(1S)-1-(4-fluorophenyl)ethyl]-2-[3-(4-hydroxyphenyl)-4-oxochromen-7-yloxy]acetamide;

2-[3-(4-hydroxyphenyl)-4-oxochromen-7-yloxy]-N-[2-(trifluoromethyl)-phenyl]acetamide;

N-(3-fluorophenyl)-2-[3-(4-hydroxyphenyl)-4-oxo-chromen-7-yloxy]acetamide;

N-[(1R)-1-(4-fluorophenyl)ethyl]-2-[3-(4-hydroxyphenyl)-4-oxochromen-7-yloxy]acetamide.

EXAMPLE 16

Preparation of a Compound of Formula I

A. Preparation of a Compound of Formula I in which $R^1$ is 3-Trifluoromethylphenyl, $R^2$ is 4-Hydroxy $R^3$ is Hydrogen, X, Y and Z are —CH—, V is Oxygen, and W is —CH$_2$NHCH$_2$CH(OH)CH$_2$—

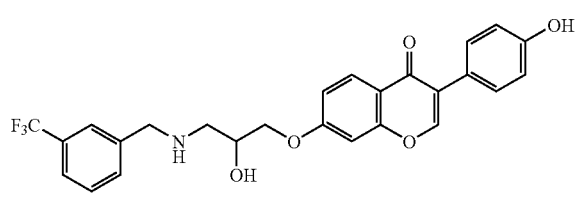

Step 1

A mixture of 7-hydroxy-3-(4-methoxyphenyl)chromen-4-one (0.86 g, 3.21 mmol), epichlorohydrin (1.25 ml, 16 mmol) and potassium carbonate (0.89 g, 6.42 mmol) in dimethylformamide (20 ml) was stirred at 80° C. for 3 hours. After removing solvent under reduced pressure, water was added to the residue, and the precipitate filtered off and washed with water. The crude product was purified by chromatography on silica gel, eluting with ethyl acetate/hexanes. (1:4 to 2:3), to afford 3-(4-methoxyphenyl)-7-(oxiran-2-ylmethoxy)chromen-4-one.

Step 2

3-(4-Methoxyphenyl)-7-(oxiran-2-ylmethoxy)chromen-4-one (0.24 g, 0.74 mmol), 3-(trifluoromethyl)benzylamine (0.11 ml, 0.74 mmol) and diisopropylethylamine (0.26 g, 1.47 mmol) was stirred in ethanol (15 ml) at 78° C. overnight. The solvent was removed under reduced pressure, and the residue chromatographed on silica gel, eluting with 5% methanol/dichloromethane, followed by recrystallization from ethyl acetate/hexane to provide 7-[2-hydroxy-3-({[3-(trifluoromethyl)phenyl]methyl}amino)propoxy]-3-(4-methoxyphenyl)chromen-4-one.

Step 3

To a stirred suspension of 7-[2-hydroxy-3-({[3-(trifluoromethyl)phenyl]methyl}-amino)propoxy]-3-(4-methoxyphenyl)chromen-4-one (38 mg, 0.076 mmol) in methylene chloride at ° C. was added boron tribromide (1M, 0.38 ml). The resulting mixture was stirred at room temperature for 4 hours, then the solvent removed under reduced pressure. The residue was purified by preparative thin layer chromatography, eluting with 10% methanol/dichloromethane, to provide 3-(4-hydroxyphenyl)-7-[2-hydroxy-3-({[3-(trifluoromethyl)phenyl]methyl}amino)propoxy]chromen-4-one.

B.

Similarly, following the procedures of Example 16A above, but substituting 3-(trifluoromethyl)benzylamine by 3,5-difluorobenzylamine, the following compound was prepared:

7-(3-{[(3,5-difluorophenyl)methyl]amino}-2-hydroxypropoxy)-3-(4-hydroxyphenyl)chromen-4-one; and 7-(2-{[(4-fluorophenyl)ethyl]amino}ethoxy)-3-(4-hydroxyphenyl)chromen-4-one.

EXAMPLE 17

Preparation of a Compound of Formula I

A. Preparation of a Compound of Formula I in which $R^1$ is Phenyl, $R^2$ is 4-Hydroxy, $R^3$ is Hydrogen, X, Y and Z are —CH—, V is Oxygen, and W is —CH$_2$CH(OH)CH$_2$—

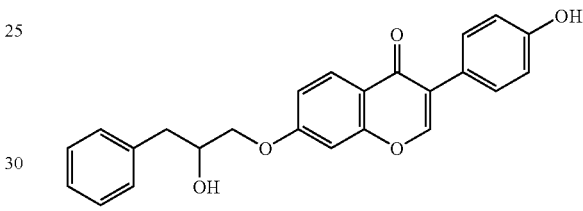

Step 1

To a solution of cuprous iodide (0.14 g, 0.74 mmol) in tetrahydrofuran (2 ml) was added phenylmagnesium bromide in tetrahydrofuran (1M, 2.22 ml, 2.22 mmol) dropwise at −40° C. After 5 minutes 3-(4-methoxyphenyl)-7-(oxiran-2-ylmethoxy)chromen-4-one (0.24 g, 0.74 mmol) in tetrahydrofuran (4 ml) was added slowly, and stirred at −40° C. for 1 hour. The mixture was quenched with saturated ammonium chloride and water, extracted with ethyl acetate, the organic layer washed with brine, dried over sodium sulfate, and the solvent removed under reduced pressure. The residue was purified by preparative thin layer chromatography, eluting with 10% methanol/methylene chloride, followed by ethyl acetate/hexane 2/3, to provide 7-(2-hydroxy-3-phenylpropoxy)-3-(4-methoxyphenyl)chromen-4-one.

Step 2

The product of step 1 was then reacted with boron tribromide as shown in Example 16, step 3, to provide 3-(4-hydroxyphenyl)-7-(2-hydroxy-3-phenylpropoxy)chromen-4-one.

EXAMPLE 18

Preparation of a Compound of Formula I

A. Preparation of the R Enantiomer of a Compound of Formula I in which $R^1$ is 3-[5-Fluoro-3-(trifluoromethyl)phenyl](1,2,4-oxadiazol-5-yl), $R^2$ is 4-Hydroxy, $R^3$ is Hydrogen, X, Y and Z are —CH—, V is Oxygen, and W is —CH(CH$_3$)—

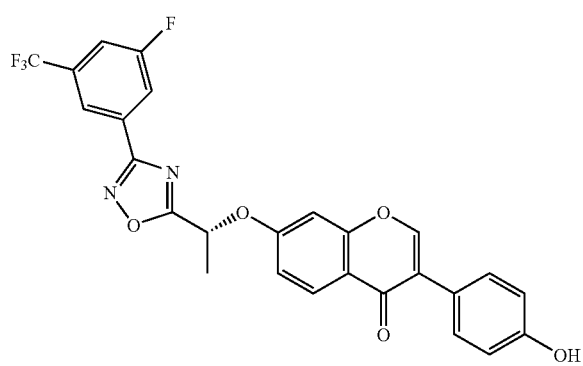

Step 1

A solution of [5-fluoro-3-(trifluoromethyl)-phenyl](hydroxyimino)methylamine (28.04 g, 126.24 mmol), prepared as shown in Example 1, was dissolved in tetrahydrofuran (40 ml) and cooled to −78° C. A solution of (1S)-1-(chlorocarbonyl)ethyl acetate (20 g, 128.82 mmol) in tetrahydrofuran (20 ml) was added dropwise under an atmosphere of dry nitrogen, and stirred for 10 minutes after the addition was complete. A solution of diisopropylethylamine (27.0 ml, 155 mmol) was then added dropwise, and the reaction mixture allowed to warm to room temperature. The mixture was stirred for two hours, then the solvent removed under reduced pressure. The residue was poured into ethyl acetate (150 ml), washed with water (2×50 ml), brine (2×50 ml), and dried over sodium sulfate. Solvent was removed under reduced pressure, to provide 2-amino-2-[3-fluoro-5-(trifluoromethyl)phenyl]-1-azavinyl (2S)-2-acetyloxypropanoate as a pale yellow oil (39.04 g, MS m/z 337.1 (M+H), which was used in the next reaction with no further purification.

Step 2

To a solution of 2-amino-2-[3-fluoro-5-(trifluoromethyl)phenyl]-1-azavinyl (2S)-2-acetyloxypropanoate (5.19 g, 15.43 mmol) in anhydrous tetrahydrofuran (20 ml) at 0° C. was added a solution of 1M tetrabutylammonium fluoride in tetrahydrofuran (3 ml) dropwise under nitrogen. The reaction mixture was stirred for 3 hours at 0° C., then poured into ethyl acetate (50 ml), washed with water (2×20 ml), brine (30 ml) and dried over sodium sulfate. Solvent was removed under reduced pressure, and the residue purified by flash chromatography, eluting with methylene chloride, to provide (1S)-1-{3-[5-fluoro-3-(trifluoromethyl)phenyl](1,2,4-oxadiazol-5-yl)}ethyl acetate, LCMS 319.1.

Step 3

To a solution of (1S)-1-{3-[5-fluoro-3-(trifluoromethyl)phenyl](1,2,4-oxadiazol-5-yl)}ethyl acetate (900 mg, 2.83 mmol) in methanol (4 ml) at −15° C. was added an aqueous solution of potassium carbonate (10M, 10 ml). The mixture was stirred for 20 minutes, and the mixture allowed to warm to room temperature, stirring for 1 hour. The mixture was extracted with ethyl acetate (3×20 ml), and the combined organic phase washed with water (10 ml), brine (2×20 ml). Removal of the solvent under reduced pressure provided (1S)-1-{3-[5-fluoro-3-(trifluoromethyl)phenyl](1,2,4-oxadiazol-5-yl)}ethane-1-ol, which was crystallized from hexane to yield a white solid, LCMS 277.2.

Step 4

To a solution of triphenylphosphine (262 mg, 1 mmol) in anhydrous tetrahydrofuran (15 ml) at −78° C. was added dropwise 40% diethylazodicarboxylate (0.45 ml, 1 mmol) in toluene, and the mixture stirred for 30 minutes at −78° C. A solution of dihydroxyisoflavone (300 mg, 1.14 mmol) in a mixture of tetrahydrofuran (8 ml) and N,N-dimethylformamide (3 ml) was added slowly, and the mixture stirred for 10 minutes. A solution of (1S)-1-{3-[5-fluoro-3-(trifluoromethyl)phenyl](1,2,4-oxadiazol-5-yl)}ethane-1-ol (277 mg, 1 mmol) in tetrahydrofuran (8 ml) was added dropwise, the mixture stirred at −78° C. for 3 hours, and then allowed to warm to room temperature, stirring for 36 hours.

The reaction mixture was poured into ethyl acetate (40 ml), washed with water (10 ml), brine (2×10 ml), dried over sodium sulfate, and the solvent removed under reduced pressure. A mixture of dichloromethane/tetrahydrofuran (4 ml/1 ml) was added to the yellow residue, and the soluble portion was flash chromatographed over silica gel, eluting with ethyl acetate (0-30%)/hexane, to give a white solid, which was further purified by preparative thin layer chromatography, eluting with acetonitrile (2.5 97.5%/water, to provide 7-((1R)-1-{3-[5-fluoro-3-(trifluoromethyl)phenyl](1,2,4-oxadiazol-5-yl)}ethoxy)-3-(4-hydroxyphenyl)chromen-4-one; 245 mg, 0.48 mmol, 48%). MS m/z 513.1 (M+H), anal HPLC >99%, Chiralcel OJ-RH hplc 99.2% e.e. (mass detector), and 99.0% e.e. (UV detector) in acetonitrile/water.

¹H NMR (400 MHz; CDCl₃) δ 8.25 (d, 1H, J=9.0 Hz); 8.18 (s, 1H); 7.99 (m, 1H); 7.91 (s, 1H); 7.49 (m, 1H); 7.42 (d, 2H, J=8.6 Hz); 7.09 (dd, 1H, J=9.0, 2.3 Hz); 6.97 (d, 1H, J=2.3 Hz); 6.88 (d, 2H, J=9.0 Hz); 5.59 (t, 1H, J=6.6 Hz); 1.96 (d, 1H, J=6.6 Hz).

EXAMPLE 19

Preparation of a Prodrug of a Compound of Formula I

A. Preparation of the Phosphate of a Compound of Formula I in which $R^1$ is 5-Fluoro-3-(trifluoromethyl)phenyl](1,2-oxazol-5-yl), $R^2$ is 4-Hydroxy, $R^3$ is Hydrogen, X, Y and Z are —CH—, V is Oxygen, and W is $CH_2$—

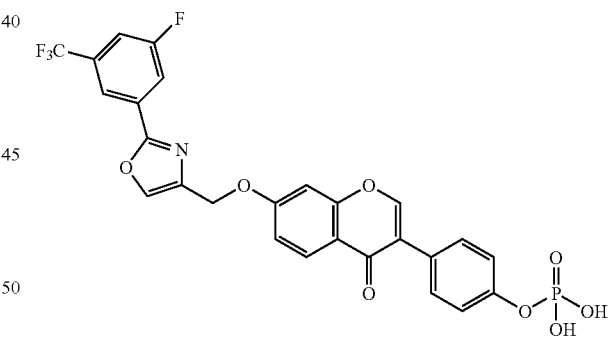

Step 1

To a solution of 7-({2-[5-fluoro-3-(trifluoromethyl)phenyl](1,3-oxazol-4-yl)}methoxy)-3-(4-hydroxyphenyl)chromen-4-one (1 g, 2.01 mmol) in tetrahydrofuran (50 mL) was added 1-H-tetrazole (3% wt in acetonitrile, 65 ml, 22.1 mmol), followed by di-tert-butyl N,N-diethylphosphoramidite (2.57 ml, 4.6 mmol). After stirring at room temperature for 2 hours, the reaction mixture was diluted with methylene chloride and washed with saturated sodium bicarbonate. The organic layer was separated, and the aqueous layer extracted twice more with methylene chloride. The combined extracts were dried over sodium sulfate, and solvent removed under reduced pressure. The residue was purified by biotage column chromatography, eluting with ethyl acetate/hexane mixture (1:4) to afford 3-{4-[bis(tert-butoxy)phosphinooxy]phenyl}-7-({2-[5-fluoro-3-(trifluoromethyl)phenyl](1,3-oxazol-4-yl)}methoxy)chromen-4-one.

Step 2

To a solution of the product of step 1, 3-{4-[bis(tert-butoxy)phosphinooxy]phenyl}-7-({2-[5-fluoro-3-(trifluoromethyl)phenyl](1,3-oxazol-4-yl)}methoxy)chromen-4-one, in a mixture of tetrahydrofuran (20 mL) and acetonitrile (10 mL) was added 6 mL of tert-butyl hydroperoxide in decane (5M-6M). The reaction mixture was stirred at room temperature for 1 hour, chilled in an ice bath, and 50 mL of 5% sodium bisulfite was added. The resulting mixture was stirred for 15 minutes, after which the ice bath was removed. The mixture was extracted with methylene chloride, the organic extract dried over sodium sulfate, and solvent removed under reduced pressure. The residue was purified by biotage column chromatography, eluting with 1:1 ethyl Acetate/hexanes mixture, to afford ditert-butyl 4-[7-({2-[5-fluoro-3-(trifluoromethyl)phenyl](1,3-oxazol-4-yl)}methoxy)-4-oxochromen-3-yl]phenyl phosphate.

Step 3

To a solution of 3-{4-[bis(tert-butoxy)phosphinooxy]phenyl}-7-({2-[5-fluoro-3-(trifluoromethyl)phenyl](1,3-oxazol-4-yl)}methoxy)chromen-4-one prepared in Step 2 in methylene chloride (60 ml) was added trifluoroacetic acid (0.15 ml, 1.99 mmol). The reaction mixture was stirred at room temperature overnight, the solid filtered off, and washed with methylene chloride, to afford 100% pure (by HPLC) 4-[7-({2-[5-fluoro-3-(trifluoromethyl)phenyl](1,3-oxazol-4-yl)}methoxy)-4-oxochromen-3-yl]phenyl dihydrogen phosphate.

EXAMPLE 20

Preparation of a Prodrug of a Compound of Formula I

A. Preparation of the Methyldihydrogenphosphate of a Compound of Formula I in which $R^1$ is 5-Fluoro-3-trifluoromethyl)phenyl](1,2-oxazol-5-yl), $R^2$ is 4-Hydroxy, $R^3$ is Hydrogen, X, Y and Z are —CH—, V is Oxygen, and W is $CH_2$—

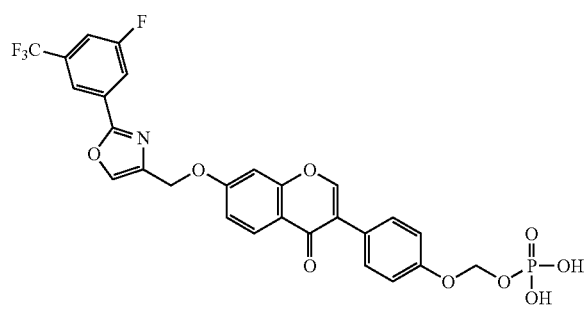

Step 1—Preparation of di-t-butyl chloromethyl phosphate

A 100 mL round bottomed flask was charged with potassium ditert-butyl phosphate (1.0 g, 4.03 mmol), sodium bicarbonate (677.4 mg, 8.06 mmol), n-butylammonium sulfate (68.2 mg, 0.403 mmol), water (10 ml) and methylene chloride (5 ml). To the mixture was added a solution of chloromethylchlorosulfonate (797.9 mg, 4.84 mmol) in methylene chloride (5 ml), and the mixture stirred at room temperature for 2 hours. To the reaction product was added water (30 ml), and the whole was extracted with methylene chloride (30 ml×3). The combined organic layers were washed with brine (30 ml), dried with $Na_2SO_4$, and solvent removed under reduced pressure. The residue was purified by column-chromatography (silica gel=80 g, hexane/ethyl acetate=1:1) to give di-t-butyl chloromethyl phosphate, as a colorless oil.

Step 2—Preparation of di-tert-butyl (4-(7-((2-(3-fluoro-5-(trifluoromethyl)phenyl)oxazol-4-yl)methoxy)-4-oxo-4H-chromen-3-yl)phenoxy)methyl phosphate In a 50 mL round bottomed flask 7-({2-[5-fluoro-3-(trifluoromethyl)phenyl](1,3-oxazol-4-yl)}methoxy)-3-(4-hydroxyphenyl)chromen-4-one (150.0 mg, 0.302 mmol) was treated with di-tert-butyl chloromethyl phosphate (156.2 mg, 0.604 mmol, 1.0 equiv) in the presence of potassium t-butoxide (67.8 mg, 0.604 mmol, 1.0 equiv) and sodium iodide (89.9 mg, 0.604 mmol, 1.0 equiv) in N,N-dimethylformamide (2 ml), and the mixture stirred at room temperature for 15 hours. To the mixture was added water (30 ml), and the whole was extracted with ethyl acetate (30 ml×3). The combined organic layers were washed with brine (30 ml), dried with $Na_2SO_4$, and solvent removed under reduced pressure, to give a crude mixture (345.1 mg). This mixture was purified by column-chromatography ($SiO_2$=80 g, hexane/EtOAc=1:1) to give di-tert-butyl {4-[7-({2-[5-fluoro-3-(trifluoromethyl)phenyl](1,3-oxazol-4-yl)}methoxy)-4-oxochromen-3-yl]phenoxy}methyl phosphate as a colorless oil.

Step 3—Preparation of (4-(7-((2-(3-fluoro-5-(trifluoromethyl)phenyl)oxazol-4-yl)methoxy)-4-oxo-4H-chromen-3-yl)phenoxy)methyl dihydrogen phosphate In a 50 mL round bottomed flask ditert-butyl {4-[7-({2-[5-fluoro-3-(trifluoromethyl)phenyl](1,3-oxazol-4-yl)}methoxy)-4-oxochromen-3-yl]phenoxy}methyl phosphate (119.1 mg, 0.166 mmol) was treated with trifluoroacetic acid (37.9 mg, 0.332 mmol, 2.0 equiv) in methylene chloride (2 ml). The mixture was stirred at room temperature for 18 hours, methylene chloride (10 ml) added, and the suspension thus obtained was filtered through a glass filter. The residue on the filter was collected to give {4-[7-({2-[5-fluoro-3-(trifluoromethyl)phenyl](1,3-oxazol-4-yl)}methoxy)-4-oxochromen-3-yl]phenoxy}methyl dihydrogen phosphate.

EXAMPLE 21

Hard gelatin capsules containing the following ingredients are prepared:

| Ingredient | Quantity (mg/capsule) |
| --- | --- |
| Active Ingredient | 30.0 |
| Starch | 305.0 |
| Magnesium stearate | 5.0 |

The above ingredients are mixed and filled into hard gelatin capsules.

EXAMPLE 22

A tablet formula is prepared using the ingredients below:

| Ingredient | Quantity (mg/tablet) |
| --- | --- |
| Active Ingredient | 25.0 |
| Cellulose, microcrystalline | 200.0 |
| Colloidal silicon dioxide | 10.0 |
| Stearic acid | 5.0 |

The components are blended and compressed to form tablets.

EXAMPLE 23

A dry powder inhaler formulation is prepared containing the following components:

| Ingredient | Weight % |
| --- | --- |
| Active Ingredient | 5 |
| Lactose | 95 |

The active ingredient is mixed with the lactose and the mixture is added to a dry powder inhaling appliance.

EXAMPLE 24

Tablets, each containing 30 mg of active ingredient, are prepared as follows:

| Ingredient | Quantity (mg/tablet) |
| --- | --- |
| Active Ingredient | 30.0 mg |
| Starch | 45.0 mg |
| Microcrystalline cellulose | 35.0 mg |
| Polyvinylpyrrolidone (as 10% solution in sterile water) | 4.0 mg |
| Sodium carboxymethyl starch | 4.5 mg |
| Magnesium stearate | 0.5 mg |
| Talc | 1.0 mg |
| Total | 120 mg |

The active ingredient, starch and cellulose are passed through a No. 20 mesh U.S. sieve and mixed thoroughly. The solution of polyvinylpyrrolidone is mixed with the resultant powders, which are then passed through a 16 mesh U.S. sieve. The granules so produced are dried at 50° C. to 60° C. and passed through a 16 mesh U.S. sieve. The sodium carboxymethyl starch, magnesium stearate, and talc, previously passed through a No. 30 mesh U.S. sieve, are then added to the granules which, after mixing, are compressed on a tablet machine to yield tablets each weighing 120 mg.

EXAMPLE 25

Suppositories, each containing 25 mg of active ingredient are made as follows:

| Ingredient | Amount |
| --- | --- |
| Active Ingredient | 25 mg |
| Saturated fatty acid glycerides to | 2,000 mg |

The active ingredient is passed through a No. 60 mesh U.S. sieve and suspended in the saturated fatty acid glycerides previously melted using the minimum heat necessary. The mixture is then poured into a suppository mold of nominal 2.0 g capacity and allowed to cool.

EXAMPLE 26

Suspensions, each containing 50 mg of active ingredient per 5.0 mL dose are made as follows:

| Ingredient | Amount |
| --- | --- |
| Active Ingredient | 50.0 mg |
| Xanthan gum | 4.0 mg |
| Sodium carboxymethyl cellulose (11%) Microcrystalline cellulose (89%) | 50.0 mg |
| Sucrose | 1.75 g |
| Sodium benzoate | 10.0 mg |
| Flavor and Color | q.v. |
| Purified water to | 5.0 mL |

The active ingredient, sucrose and xanthan gum are blended, passed through a No. 10 mesh U.S. sieve, and then mixed with a previously made solution of the microcrystalline cellulose and sodium carboxymethyl cellulose in water. The sodium benzoate, flavor, and color are diluted with some of the water and added with stirring. Sufficient water is then added to produce the required volume.

EXAMPLE 27

A subcutaneous formulation may be prepared as follows:

| Ingredient | Quantity |
| --- | --- |
| Active Ingredient | 5.0 mg |
| Corn Oil | 1.0 mL |

EXAMPLE 28

An injectable preparation is prepared having the following composition.

| Ingredients | Amount |
| --- | --- |
| Active ingredient | 2.0 mg/ml |
| Mannitol, USP | 50 mg/ml |
| Gluconic acid, USP | q.s. (pH 5-6) |
| water (distilled, sterile) | q.s. to 1.0 ml |
| Nitrogen Gas, NF | q.s. |

EXAMPLE 29

A topical preparation is prepared having the following composition:

| Ingredients | grams |
| --- | --- |
| Active ingredient | 0.2-10 |
| Span 60 | 2.0 |
| Tween 60 | 2.0 |
| Mineral oil | 5.0 |
| Petrolatum | 0.10 |
| Methyl paraben | 0.15 |
| Propyl paraben | 0.05 |
| BHA (butylated hydroxy anisole) | 0.01 |
| Water | q.s. to 100 |

All of the above ingredients, except water, are combined and heated to 60° C. with stirring. A sufficient quantity of water at 60° C. is then added with vigorous stirring to emulsify the ingredients, and water then added q.s. 100 g.

EXAMPLE 30

Sustained Release Composition

| Ingredient | Weight Range (%) | Preferred Range (%) | Most Preferred |
| --- | --- | --- | --- |
| Active ingredient | 50-95 | 70-90 | 75 |
| Microcrystalline cellulose (filler) | 1-35 | 5-15 | 10.6 |
| Methacrylic acid copolymer | 1-35 | 5-12.5 | 10.0 |
| Sodium hydroxide | 0.1-1.0 | 0.2-0.6 | 0.4 |
| Hydroxypropyl methylcellulose | 0.5-5.0 | 1-3 | 2.0 |
| Magnesium stearate | 0.5-5.0 | 1-3 | 2.0 |

The sustained release formulations of this invention are prepared as follows: compound and pH-dependent binder and any optional excipients are intimately mixed (dry-blended). The dry-blended mixture is then granulated in the presence of an aqueous solution of a strong base which is sprayed into the blended powder. The granulate is dried, screened, mixed with optional lubricants (such as talc or magnesium stearate), and compressed into tablets. Preferred aqueous solutions of strong bases are solutions of alkali metal hydroxides, such as sodium or potassium hydroxide, preferably sodium hydroxide, in water (optionally containing up to 25% of water-miscible solvents such as lower alcohols).

The resulting tablets may be coated with an optional film-forming agent, for identification, taste-masking purposes and to improve ease of swallowing. The film forming agent will typically be present in an amount ranging from between 2% and 4% of the tablet weight. Suitable film-forming agents are well known to the art and include hydroxypropyl, methylcellulose, cationic methacrylate copolymers (dimethylaminoethyl methacrylate/methyl-butyl methacrylate copolymers—Eudragit® E—Röhm. Pharma), and the like. These film-forming agents may optionally contain colorants, plasticizers, and other supplemental ingredients.

The compressed tablets preferably have a hardness sufficient to withstand 8 Kp compression. The tablet size will depend primarily upon the amount of compound in the tablet. The tablets will include from 300 to 1100 mg of compound free base. Preferably, the tablets will include amounts of compound free base ranging from 400-600 mg, 650-850 mg, and 900-1100 mg.

In order to influence the dissolution rate, the time during which the compound containing powder is wet mixed is controlled. Preferably the total powder mix time, i.e. the time during which the powder is exposed to sodium hydroxide solution, will range from 1 to 10 minutes and preferably from 2 to 5 minutes. Following granulation, the particles are removed from the granulator and placed in a fluid bed dryer for drying at about 60° C.

EXAMPLE 31

MAO-A, MAO-B, and ALDH-2 Inhibition Assays

ALDH2 inhibition assays were performed in sodium phosphate buffer (50 mM, pH 7.4) containing 1.2 mM $NAD^+$ (Sigma N7004), 1 nM hALDH2 (recombinant human mitochondria ALDH), various concentrations of test compounds (from 0.03 nM to 1000 DM), and 0.15 mM freshly prepared formaldehyde solution (Ladd Research 20295). Reactions were initiated by the addition of formaldehyde and rates were recorded by monitoring NADH formation in a temperature controlled (25° C.) FluoroMax-2 Fluorimeter with excitation and emission wavelengths set at 340 and 460 nm, respectively. Slow binding or irreversible inhibitors (inhibitors that exhibit time-dependent inhibition kinetics) were pre-incubated with enzyme in the presence of NAD for 5-15 min before the addition of aldehyde substrate. Normally, $IC_{50}$ values were determined by fitting concentration-inhibition data to sigmoidal dose-response curves with two-floating parameters: $IC_{50}$ and Hill coefficient. When tight binding situation was suspected, apparent Ki values were estimated by fitting dose-response data to Morrison's equation [*Methods in Enzymology* 63, 437-467, 1979].

MAO-A (Sigma M7316) and MAO-B (Sigma M7441) inhibition assays were conducted in 96-well micro-plates according to the method described by Zhou et al. [*Analytical Biochemistry* 253, 169-174, 1997]. Both assays were performed in potassium phosphate buffer (0.1 M, pH 7.5) containing 0.5 mM tyramine (Sigma T2879), 0.12 mM N-acetyl-3,7-dihydrophenoxazine (Amplex Red, Invitrogen A12222), 1.2 unit/ml horseradish peroxidase (Sigma P2088), 0.6 unit/ml MAO-A or 2.5 unit/ml MAO-B, and various concentrations of test compounds (0.1 nM to 10 uM). Reactions were initiated by the addition of a pre-mixed solution of tyramine, horseradish peroxidase and Amplex Red, and were allowed to proceed at 37° C. for 30 min. Enzyme activities were determined by measuring absorbance at 570 nm (SpectralMax Plate reader), absorbance of oxidized Amplex Red generated by this horseradish peroxidase-coupled reaction. Nonspecifically formed products were determined in the presence of 2 and 10 □M clorgyline and deprenyl for MAO-A and MAO-B, respectively. $IC_{50}$ values were determined by fitting concentration-inhibition data to sigmoidal dose-response curves with two-floating parameters: $IC_{50}$ and Hill coefficient.

Representative data for several compounds of the invention are presented in Table 1 below.

TABLE 1

ALDH-2 AND MAO INHIBITION

| | COMPOUND | IC$_{50}$ hALDH2 | IC$_{50}$ hMAO-A | IC$_{50}$ hMAO-B |
|---|---|---|---|---|
| PT-1. | 4-[7-({5-[3-fluoro-5-(trifluoromethyl)phenyl](1,2,4-oxadiazol-3-yl)}methoxy)-4-oxochromen-3-yl]benzenecarbonitrile; | 17% inhibition at 1 μM | | |
| PT-2. | 7-({3-[5-fluoro-3-(trifluoromethyl)phenyl](1,2,4-oxadiazol-5-yl)}ethoxy)-3-(4-hydroxyphenyl)chromen-4-one; | 43% inhibition at 1 μM | No inhibition up to 10 μM | 8% inhibition at 10 μM |
| PT-3. | ethyl 3-[7-({5-[3-fluoro-5-(trifluoromethyl)phenyl](1,2,4-oxadiazol-3-yl)}methoxy)-4-oxochromen-3-yl]benzoate; | 22% inhibition at 1 μM | | |
| PT-4. | 3-(4-hydroxyphenyl)-7-({4-methyl-2-[4-(trifluoromethyl)phenyl](1,3-thiazol-5-yl)}methoxy)chromen-4-one; | 0.20 μM | | |
| PT-5. | 3-(4-{[(4-methylphenyl)sulfonyl]amino}phenyl)-7-({4-methyl-2-[4-(trifluoromethyl)phenyl](1,3-thiazol-5-yl)}methoxy)chromen-4-one; | 0.19% inhibition at 1 μM | | |
| PT-6. | methyl 3-{[3-(6-methoxy(3-pyridyl))-4-oxochromen-7-yloxy]methyl}benzoate; | 16% inhibition at 1 μM | | |
| PT-7. | methyl 3-({3-[4-(hydroxymethyl)phenyl]-4-oxochromen-7-yloxy}methyl)benzoate; | 75% inhibition at 1 μM | | |
| PT-8. | 7-({3-[5-fluoro-3-(trifluoromethyl)phenyl](1,2,4-oxadiazol-5-yl)}methoxy)-3-{4-[(methylsulfonyl)amino]phenyl}chromen-4-one; | 57% inhibition at 1 μM | | |
| PT-9. | 2-fluoro-5-[7-({5-[3-fluoro-3-(trifluoromethyl)phenyl](1,2,4-oxadiazol-3-yl)}methoxy)-4-oxochromen-3-yl]benzenecarbonitrile; | 25% inhibition at 1 μM | | |
| PT-10. | ethyl 2-(3-{4-[(ethoxycarbonyl)methoxy]phenyl}-4-oxochromen-7-yloxy)acetate; | 60% inhibition at 1 μM | | |
| PT-11. | 7-{[5-(4-fluorophenyl)(1,2,4-oxadiazol-3-yl)]methoxy}-3-(4-hydroxyphenyl)chromen-4-one; | 0.02 μM | No inhibition up to 10 μM | 35% inhibition at 10 μM |
| PT-12. | 3-(4-hydroxyphenyl)-7-({2-[3-(trifluoromethyl)phenyl](1,3-oxazol-4-yl)}methoxy)chromen-4-one; | 0.003 μM | No inhibition up to 10 μM | No inhibition at 10 μM |
| PT-13. | 7-({2-[5-fluoro-3-(trifluoromethyl)phenyl](1,3-oxazol-4-yl)}methoxy)-3-(4-hydroxyphenyl)chromen-4-one; | 0.02 μM | No inhibition up to 10 μM | No inhibition at 10 μM |
| PT-14. | 7-{[2-(3,5-difluorophenyl)(1,3-oxazol-4-yl)]methoxy}-3-(4-hydroxyphenyl)chromen-4-one; | 0.06 μM | No inhibition up to 10 μM | No inhibition at 10 μM |
| PT-15. | 7-{[2-(3,4-difluorophenyl)(1,3-oxazol-4-yl)]methoxy}-3-(4-hydroxyphenyl)chromen-4-one; | 0.12 μM | | |
| PT-16. | 7-{[2-(4-fluorophenyl)(1,3-oxazol-4-yl)]methoxy}-3-(4-hydroxyphenyl)chromen-4-one; and | 0.047 μM | No inhibition up to 10 μM | No inhibition at 10 μM |
| PT-17. | 7-{[2-(4-chlorophenyl)(1,3-oxazol-4-yl)]methoxy}-3-(4-hydroxyphenyl)chromen-4-one. | 0.573 μM | | |
| PT-18. | 3-(4-hydroxyphenyl)-7-({2-[3-(trifluoromethyl)phenyl](1,3-oxazol-4-yl)}methoxy)chromen-4-one; | 0.003 μM | No inhibition up to 10 μM | No inhibition at 10 μM |
| PT-19. | 7-({2-[5-fluoro-3-(trifluoromethyl)phenyl](1,3-oxazol-4-yl)}methoxy)-3-(4-hydroxyphenyl)chromen-4-one; | 0.02 μM | No inhibition up to 10 μM | No inhibition at 10 μM |
| PT-20. | 7-{[2-(3,5-difluorophenyl)(1,3-oxazol-4-yl)]methoxy}-3-(4-hydroxyphenyl)chromen-4-one; | 0.06 μM | No inhibition up to 10 μM | No inhibition at 10 μM |
| PT-21. | 7-{[2-(3,4-difluorophenyl)(1,3-oxazol-4-yl)]methoxy}-3-(4-hydroxyphenyl)chromen-4-one; | 0.12 μM | | |
| PT-22. | 7-{[2-(4-fluorophenyl)(1,3-oxazol-4-yl)]methoxy}-3-(4-hydroxyphenyl)chromen-4-one; and | 0.047 μM | No inhibition up to 10 μM | No inhibition at 10 μM |
| PT-23. | 7-{[2-(4-chlorophenyl)(1,3-oxazol-4-yl)]methoxy}-3-(4-hydroxyphenyl)chromen-4-one. | 0.573 μM | | |

TABLE 1-continued

ALDH-2 AND MAO INHIBITION

| | COMPOUND | IC$_{50}$ hALDH2 | IC$_{50}$ hMAO-A | IC$_{50}$ hMAO-B |
|---|---|---|---|---|
| PT-24. | 3-(4-hydroxyphenyl)-7-[(5-phenyl(1,2,4-oxadiazol-3-yl))methoxy]chromen-4-one | 0.16 μM | No inhibition up to 40 μM | No inhibition up to 40 μM |
| PT-25. | 3-{[3-(4-hydroxyphenyl)-4-oxochromen-7-yloxy]methyl}benzenecarbonitrile; | 0.004 μM | No inhibition up to 10 μM | No inhibition up to 10 μM |
| PT-26. | 3-(4-hydroxyphenyl)-7-{[3-(trifluoromethyl)phenyl]methoxy}chromen-4-one; | 0.034 μM | | |
| PT-27. | 3-(4-hydroxyphenyl)-7-{[4-methoxy-3-(trifluoromethyl)phenyl]methoxy}chromen-4-one; | 0.02 μM | No inhibition up to 10 μM | No inhibition up to 10 μM |
| PT-28. | 7-{[3-fluoro-5-(trifluoromethyl)phenyl]methoxy}-3-(4-hydroxyphenyl)chromen-4-one; | 0.058 μM | | |
| PT-29. | 7-({5-[3-fluoro-5-(trifluoromethyl)phenyl](1,2,4-oxadiazol-3-yl)}methoxy)-3-(4-hydroxyphenyl)chromen-4-one; | 0.01 μM | No inhibition up to 30 μM | No inhibition up to 30 μM |
| PT-30. | 7-({5-[4-fluoro-3-(trifluoromethyl)phenyl](1,2,4-oxadiazol-3-yl)}methoxy)-3-(4-hydroxyphenyl)chromen-4-one; | 0.10 μM | No inhibition up to 10 μM | No inhibition up to 10 μM |
| PT-31. | 7-({5-[2,5-bis(trifluoromethyl)phenyl](1,2,4-oxadiazol-3-yl)}methoxy)-3-(4-hydroxyphenyl)chromen-4-one; | 0.02 μM | No inhibition up to 10 μM | No inhibition up to 10 μM |
| PT-32. | prop-2-enyl 3-(3-{[3-(4-hydroxyphenyl)-4-oxochromen-7-yloxy]methyl}-1,2,4-oxadiazol-5-yl)benzoate; (ESI) m/z 497 (M + H)+. | 1.15 μM | No inhibition up to 10 μM | No inhibition up to 10 μM |
| PT-33. | methyl 3-{[3-(4-hydroxyphenyl)-4-oxochromen-7-yloxy]methyl}benzoate; | 0.15 μM | No inhibition up to 30 μM | 0.3 μM |
| PT-34. | ethyl 4-{[3-(4-hydroxyphenyl)-4-oxochromen-7-yloxy]methyl}benzoate; | 0.13 μM | 24 μM | 2.3 μM |
| PT-35. | methylethyl 3-{[3-(4-hydroxyphenyl)-4-oxochromen-7-yloxy]methyl}benzoate; | 0.02 μM | No inhibition up to 10 μM | No inhibition up to 10 μM |
| PT-36. | 4-{[3-(4-hydroxyphenyl)-4-oxochromen-7-yloxy]methyl}benzoic acid; (ESI) m/z 389 (M + H)+. | 0.17 μM | No inhibition up to 40 μM | No inhibition up to 30 μM |
| PT-37. | 4-{[3-(4-hydroxyphenyl)-4-oxochromen-7-yloxy]methyl}benzamide; | 0.38 μM | No inhibition up to 30 μM | No inhibition up to 30 μM |
| PT-38. | 3-(4-hydroxyphenyl)-7-({5-[4-(trifluoromethyl)phenyl](1,2,4-oxadiazol-3-yl)}methoxy)chromen-4-one; | 0.6 μM | No inhibition up to 30 μM | No inhibition up to 30 μM |
| PT-39. | 7-({5-[3,5-bis(trifluoromethyl)phenyl](1,2,4-oxadiazol-3-yl)}methoxy)-3-(4-hydroxyphenyl)chromen-4-one; | 0.13 μM | No inhibition up to 10 μM | No inhibition up to 10 μM |
| PT-40. | 3-(3-{[3-(4-hydroxyphenyl)-4-oxochromen-7-yloxy]methyl}-1,2,4-oxadiazol-5-yl)benzenecarbonitrile; | 0.022 μM | No inhibition up to 10 μM | No inhibition up to 10 μM |
| PT-41. | 3-(3-{[3-(4-hydroxyphenyl)-4-oxochromen-7-yloxy]methyl}-1,2,4-oxadiazol-5-yl)benzoic acid; | 0.01 μM | No inhibition up to 10 μM | No inhibition up to 10 μM |
| PT-42. | 7-{[5-(3-fluorophenyl)(1,2,4-oxadiazol-3-yl)]methoxy}-3-(4-hydroxyphenyl)chromen-4-one. | 0.062 μM | No inhibition up to 10 μM | No inhibition up to 10 μM |
| PT-43. | 3-(4-hydroxyphenyl)-7-[(3-phenyl(1,2,4-oxadiazol-5-yl))methoxy]chromen-4-one; | 0.47 μM | No inhibition up to 30 μM | No inhibition up to 30 μM |
| PT-44. | 3-(4-hydroxyphenyl)-7-({3-[4-chlorophenyl](1,2,4-oxadiazol-5-yl)}methoxy)chromen-4-one; | 0.27 μM | No inhibition up to 30 μM | No inhibition up to 30 μM |
| PT-45. | 3-(4-hydroxyphenyl)-7-({5-[3-(trifluoromethyl)phenyl]isoxazol-3-yl}methoxy)chromen-4-one; | 0.098 μM | No inhibition up to 10 μM | 7% inhibition at 10 μM |
| PT-46. | 7-{[5-(trifluoromethyl)(3-pyridyl)]methoxy}-3-(4-{[6-(trifluoromethyl)(3-pyridyl)]methoxy}phenyl)chromen-4-one; | 10% inhibition at 1 μM | | |
| PT-47. | methyl 2-{[3-(4-hydroxyphenyl)-4-oxochromen-7-yloxy]methyl}-1,3-oxazole-5-carboxylate; | 0.005 μM | No inhibition up to 10 μM | 34% inhibition at 10 μM |

TABLE 1-continued

ALDH-2 AND MAO INHIBITION

| | COMPOUND | IC$_{50}$ hALDH2 | IC$_{50}$ hMAO-A | IC$_{50}$ hMAO-B |
|---|---|---|---|---|
| PT-48. | 7-{[5-(4-fluorophenyl)(1,2,4-oxadiazol-3-yl)]methoxy}-3-{4-[(methylsulfonyl)amino]phenyl}chromen-4-one; | 0.14 μM | | |
| PT-49. | 2-{[3-(4-hydroxyphenyl)-4-oxochromen-7-yloxy]methyl}-1,3-oxazole-5-carboxylic acid; | 0.016 μM | No inhibition up to 10 μM | |
| PT-50. | methyl 3-({3-[4-((1Z)-1-amino-2-methoxy-2-azavinyl)phenyl]-4-oxochromen-7-yloxy}methyl)benzoate; | 47% inhibition at 1 μM | | |
| PT-51. | 7-{2-[4-(4-chlorophenyl)pyrazolyl]ethoxy}-3-(4-hydroxyphenyl)chromen-4-one; | 0.11 μM | | |
| PT-52. | 3-(4-hydroxyphenyl)-7-[(6-pyrazolyl(3-pyridyl))methoxy]chromen-4-one; | 0.01 μM | No inhibition up to 10 μM | |
| PT-53. | 7-[(2R)-2-hydroxy-3-({[3-(trifluoromethyl)phenyl]methyl}amino)propoxy]-3-(4-hydroxyphenyl)chromen-4-one; | 0.016 μM | No inhibition up to 10 μM | 19% inhibition at 10 μM |
| PT-54. | 3-(4-hydroxyphenyl)-7-[({[3-(trifluoromethyl)phenyl]methyl}amino)methoxy]chromen-4-one; | 0.005 μM | No inhibition up to 10 μM | |
| PT-55. | 7-((2R)-3-{[(3,5-difluorophenyl)methyl]amino}-2-hydroxypropoxy)-3-(4-hydroxyphenyl)chromen-4-one; | 0.008 μM | No inhibition up to 10 μM | 14% inhibition at 10 μM |
| PT-56. | 7-(3-{[(1R)-1-(4-fluorophenyl)ethyl]amino}-2-oxopropoxy)-3-(4-hydroxyphenyl)chromen-4-one; | 0.008 μM | 36% inhibition up to 10 μM | 29% inhibition at 10 μM |
| PT-57. | 3-(4-hydroxyphenyl)-7-(3-phenylpropoxy)chromen-4-one; | 0.02 μM | No inhibition up to 10 μM | 27% inhibition at 10 μM |
| PT-58. | 7-{[5-(3-fluorophenyl)(1,3,4-oxadiazol-2-yl)]methoxy}-3-(4-hydroxyphenyl)chromen-4-one; | 0.011 μM | No inhibition up to 10 μM | 25% inhibition at 10 μM |
| PT-59. | 3-(4-hydroxyphenyl)-7-{3-(trifluoromethyl)phenyl]ethoxy}chromen-4-one; | 0.67 μM | No inhibition up to 10 μM | 24% inhibition at 10 μM |
| PT-60. | 3-(4-hydroxyphenyl)-7-({5-[3-(trifluoromethyl)phenyl](1,3,4-oxadiazol-2-yl)}methoxy)chromen-4-one; | 0.042 μM | No inhibition up to 10 μM | 13% inhibition at 10 μM |
| PT-61. | 3-(4-hydroxyphenyl)-7-[(2-phenyl(1,3-oxazol-5-yl))methoxy]chromen-4-one; | 0.096 μM | No inhibition up to 10 μM | 17% inhibition at 10 μM |
| PT-62. | 7-({5-[3,5-bis(trifluoromethyl)phenyl]isoxazol-3-yl}methoxy)-3-(4-hydroxyphenyl)chromen-4-one; | 0.072 μM | No inhibition up to 10 μM | no inhibition at 10 μM |
| PT-63. | 3-(4-hydroxyphenyl)-7-({5-[3-(trifluoromethyl)phenyl]isoxazol-3-yl}methoxy)chromen-4-one; | 0.098 μM | No inhibition up to 10 μM | 7% inhibition at 10 μM |
| PT-64. | 7-{[5-(2-chlorophenyl)(1,3,4-thiadiazol-2-yl)]methoxy}-3-(4-hydroxyphenyl)chromen-4-one; | 43% inhibition at 1 μM | No inhibition up to 10 μM | 8% inhibition at 10 μM |
| PT-65. | 4-[7-({4-methyl-2-[4-(trifluoromethyl)phenyl](1,3-thiazol-5-yl)}methoxy)-4-oxochromen-3-yl]benzenecarbonitrile; | 30% inhibition at 1 μM | No inhibition up to 10 μM | 25% inhibition at 10 μM |
| PT-66. | 3-{4-[(methylsulfonyl)amino]phenyl}-7-({4-methyl-2-[4-(trifluoromethyl)phenyl](1,3-thiazol-5-yl)}methoxy)chromen-4-one; | 48% inhibition at 1 μM | No inhibition up to 10 μM | 25% inhibition at 10 μM |
| PT-67. | 3-(6-methoxy(3-pyridyl))-7-({4-methyl-2-[4-(trifluoromethyl)phenyl](1,3-thiazol-5-yl)}methoxy)chromen-4-one; | 25% inhibition at 1 μM | No inhibition up to 10 μM | 16% inhibition at 10 μM |
| PT-68. | 4-[7-({5-[5-fluoro-3-(trifluoromethyl)phenyl](1,3,4-oxadiazol-2-yl)}methoxy)-4-oxochromen-3-yl]benzenecarbonitrile; | 33% inhibition at 1 μM | No inhibition up to 10 μM | 14% inhibition at 10 μM |
| PT-69. | 4-[4-oxo-7-({3-[3-(trifluoromethyl)phenyl]isoxazol-5-yl}methoxy)chromen-3-yl]benzenecarbonitrile; | 0.18 μM | No inhibition up to 10 μM | |
| PT-70. | 7-({5-[3-fluoro-5-(trifluoromethyl)phenyl](1,2,4-oxadiazol-3-yl)}methoxy)-3-{4-[(methylsulfonyl)amino]phenyl}chromen-4-one; | 20% inhibition at 1 μM | No inhibition up to 10 μM | 11% inhibition at 10 μM |

TABLE 1-continued

ALDH-2 AND MAO INHIBITION

| | COMPOUND | IC$_{50}$ hALDH2 | IC$_{50}$ hMAO-A | IC$_{50}$ hMAO-B |
|---|---|---|---|---|
| PT-71. | 7-({5-[3-fluoro-5-(trifluoromethyl)phenyl](1,2,4-oxadiazol-3-yl)}methoxy)-3-[4-(methylsulfonyl)phenyl]chromen-4-one; | 8% inhibition at 1 μM | No inhibition up to 10 μM | 11% inhibition at 10 μM |
| PT-72. | 4-[7-({5-[3-fluoro-5-(trifluoromethyl)phenyl](1,2,4-oxadiazol-3-yl)}methoxy)-4-oxochromen-3-yl]benzamide; | 14% inhibition at 1 μM | No inhibition up to 10 μM | No inhibition at 10 μM |
| PT-73. | 3-(3-acetylphenyl)-7-({5-[3-fluoro-5-(trifluoromethyl)phenyl](1,2,4-oxadiazol-3-yl)}methoxy)chromen-4-one; | 18% inhibition at 1 μM | No inhibition up to 10 μM | 10% inhibition at 10 μM |
| PT-74. | 7-({5-[3-fluoro-5-(trifluoromethyl)phenyl](1,3,4-oxadiazol-2-yl)}methoxy)-3-(4-hydroxyphenyl)chromen-4-one; | 0.005 μM | No inhibition up to 10 μM | 22% inhibition at 10 μM |
| PT-75. | 7-({5-[3-fluoro-5-(trifluoromethyl)phenyl](1,2,4-oxadiazol-3-yl)}methoxy)-3-(5-hydropyrazol-4-yl)chromen-4-one; | 14% inhibition at 1 μM | No inhibition up to 10 μM | No inhibition at 10 μM |
| PT-76. | ethyl 3-[7-({3-[3-fluoro-5-(trifluoromethyl)phenyl](1,2,4-oxadiazol-5-yl)}ethoxy)-4-oxochromen-3-yl]benzoate; | 0.063 μM | No inhibition up to 10 μM | 21% inhibition at 10 μM |
| PT-77. | 3-(4-hydroxyphenyl)-7-({2-[4-(trifluoromethyl)phenyl](1,3-thiazol-5-yl)}methoxy)chromen-4-one; | 0.122 μM | | |
| PT-78. | 7-[2-(3-fluorophenyl)-2-oxoethoxy]-3-(4-hydroxyphenyl)chromen-4-one; | 0.139 μM | | |
| PT-79. | 7-({5-[3-fluoro-5-(trifluoromethyl)phenyl](1,2,4-oxadiazol-3-yl)}ethoxy)-3-(4-hydroxyphenyl)chromen-4-one; | 0.048 μM | No inhibition up to 10 μM | 18% inhibition at 10 μM |
| PT-80. | 7-{[5-(2-chlorophenyl)(1,3,4-oxadiazol-2-yl)]methoxy}-3-(4-hydroxyphenyl)chromen-4-one; | 0.004 μM | No inhibition up to 10 μM | No inhibition at 10 μM |
| PT-81. | 7-{[5-(4-fluorophenyl)(1,3,4-oxadiazol-2-yl)]methoxy}-3-(4-hydroxyphenyl)chromen-4-one; | 0.0004 μM | No inhibition up to 10 μM | 12% inhibition at 10 μM |
| PT-82. | 3-(4-hydxoxyphenyl)-7-(4-pyridylmethoxy)chromen-4-one; | 0.005 μM | No inhibition up to 10 μM | 15% inhibition at 10 μM |
| PT-83. | 3-{4-[(methylsulfonyl)amino]phenyl}-7-({2-[4-(trifluoromethyl)phenyl](1,3-thiazol-5-yl)}methoxy)chromen-4-one; | 0.025 μM | | |
| PT-84. | 2-[3-(4-hydroxyphenyl)-4-oxochromen-7-yloxy]-N-[2-(trifluoromethyl)phenyl]-acetamide; | 0.015 μM | No inhibition up to 10 μM | 20% inhibition at 10 μM |
| PT-85. | 3(4-hydroxyphenyl)-7-{2-oxo-2-[2-(trifluoromethyl)phenyl]ethoxy}chromen-4-one; | 0.07 μM | No inhibition up to 10 μM | No inhibition at 10 μM |
| PT-86. | 3-(1H-indazol-5-yl)-7-({5-[5-fluoro-3-(trifluoromethyl)phenyl](1,2,4-oxadiazol-3-yl)}methoxy)chromen-4-one; | 68% inhibition at 1 μM | | |
| PT-87. | 3-(4-hydroxyphenyl)-7-(2-phenylethoxy)chromen-4-one; | 0.040% inhibition at 1 μM | No inhibition up to 10 μM | 21% inhibition at 10 μM |
| PT-88. | 2-[3-(4-hydroxyphenyl)-4-oxochromen-7-yloxy]ethanenitrile; | 0.023 μM | 6.2 μM | 35% inhibition at 10 μM |
| PT-89. | 7-[2-(4-chlorophenoxy)ethoxy]-3-(4-hydroxyphenyl)chromen-4-one; | 0.022 μM | 34% inhibition up to 10 μM | 32% inhibition at 10 μM |
| PT-90. | N-[(1R)-1-(4-fluorophenyl)ethyl]-2-[3-(4-hydroxyphenyl)-4-oxochromen-7-yloxy]acetamide; | 0.006 μM | No inhibition up to 10 μM | 12% inhibition at 10 μM |
| PT-91. | 3-(4-hydroxyphenyl)-7-(2-pyridylmethoxy)chromen-4-one; | 0.007 μM | No inhibition up to 10 μM | 11% inhibition at 10 μM |
| PT-92. | 2-fluoro-5-[7-({5-[5-fluoro-3-(trifluoromethyl)phenyl](1,2,4-oxadiazol-3-yl)}methoxy)-4-oxochromen-3-yl]benzenecarbonitrile; | 24% inhibition at 1 μM | | |
| PT-93. | 7-(2-pyridylmethoxy)-3-[4-(2-pyridylmethoxy)phenyl]chromen-4-one; | 0.017 μM | | |
| PT-94. | 3-(4-hydroxyphenyl)-7-{5-(trifluoromethyl)(3-pyridyl)]methoxy}chromen-4-one; | 0.02 μM | No inhibition up to 10 μM | No inhibition at 10 μM |

TABLE 1-continued

ALDH-2 AND MAO INHIBITION

| | COMPOUND | IC$_{50}$ hALDH2 | IC$_{50}$ hMAO-A | IC$_{50}$ hMAO-B |
|---|---|---|---|---|
| PT-95. | 7-{[5-(4-chlorophenyl)isoxazol-3-yl]methoxy}-3-(4-hydroxyphenyl)chromen-4-one; | 57% inhibition at 1 μM | | |
| PT-96. | 7-{[5-(3,4-dichlorophenyl)isoxazol-3-yl]methoxy}-3-(4-hydroxyphenyl)chromen-4-one; | 47% inhibition at 1 μM | | |
| PT-97. | 7-{[5-(4-chlorophenyl)isoxazol-3-yl]methoxy}-3-(4-hydroxyphenyl)chromen-4-one; | 57% inhibition at 1 μM | | |
| PT-98. | 7-[(2R)-2-hydroxy-3-({[3-(trifluoromethyl)phenyl]methyl}amino)propoxy]-3-(4-hydroxyphenyl)chromen-4-one; | 0.016 μM | No inhibition up to 10 μM | 19% inhibition at 10 μM |
| PT-99. | 3-(4-hydroxyphenyl)-7-[2-({[3-(trifluoromethyl)phenyl]methyl}amino)ethoxy]chromen-4-one; | 0.005 μM | No inhibition up to 10 μM | |
| PT-100. | 7-((2R)-3-{[(3,5-difluorophenyl)methyl]amino}-2-hydroxypropoxy)-3-(4-hydroxyphenyl)chromen-4-one; | 0.008 μM | No inhibition up to 10 μM | 14% inhibition at 10 μM |
| PT-101. | methyl 2-{[3-(4-hydroxyphenyl)-4-oxochromen-7-yloxy]methyl}-1,3-oxazole-4-carboxylate; | 0.005 μM | No inhibition up to 10 μM | 34% inhibition at 10 μM |
| PT-102. | 2-{[3-(4-hydroxyphenyl)-4-oxochromen-7-yloxy]methyl}-1,3-oxazole-4-carboxylic acid; | 0.016 μM | No inhibition up to 10 μM | |
| PT-103. | N-[(1S)-1-(4-fluorophenyl)ethyl]-2-[3-(4-hydroxyphenyl)-4-oxochromen-7-yloxy]acetamide; | 0.008 μM | 36% inhibition up to 10 μM | 29% inhibition at 10 μM |
| PT-104. | 7-{[5-(4-fluorophenyl)(1,2,4-oxadiazol-3-yl)]methoxy}-3-(4-hydroxyphenyl)chromen-4-one; | 0.016 μM | No inhibition up to 10 μM | No inhibition at 10 μM |
| PT-105. | 7-{[5-(4-fluorophenyl)(1,2,4-oxadiazol-3-yl)]methoxy}-3-{4-[(methylsulfonyl)amino]phenyl}chromen-4-one; | 0.14 μM | | |
| PT-106. | 7-{3-[4-(4-chlorophenyl)pyrazolyl]propoxy}-3-(4-hydroxyphenyl)chromen-4-one; | 0.11 μM | | |
| PT-107. | 3-(4-hydroxyphenyl)-7-(3-phenylpropoxy)chromen-4-one; | 0.02 μM | No inhibition up to 10 μM | 27% inhibition at 10 μM |
| PT-108. | 3-(4-hydroxyphenyl)-7-[(6-pyrazolyl(3-pyridyl))methoxy]chromen-4-one; | 0.010 μM | No inhibition up to 10 μM | |
| PT-109. | 7-((2R)-2-hydroxy-3-phenylpropoxy)-3-(4-hydroxyphenyl)chromen-4-one; | 0.014 μM | 26% inhibition up to 10 μM | 26% inhibition at 10 μM |
| PT-110. | 3-(4-hydroxyphenyl)-7-[(5-(3-pyridyl)(1,3,4-oxadiazol-2-yl))methoxy]chromen-4-one; | 0.007 μM | No inhibition up to 10 μM | No inhibition at 10 μM |
| PT-111. | 3-[(2-hydroxy-3-{4-[(methylsulfonyl)amino]phenyl}-4-oxochromen-7-yloxy)methyl]-benzoic acid; | 0.003 μM | No inhibition up to 10 μM | 30% inhibition at 10 μM |
| PT-112. | 7-{[5-(4-fluorophenyl)(1,3,4-oxadiazol-2-yl)]ethoxy}-3-(4-hydroxyphenyl)chromen-4-one; | 0.005 μM | No inhibition up to 10 μM | No inhibition at 10 μM |
| PT-113. | 3-(4-hydroxyphenyl)-7-[(5-(3-pyridyl)(1,3,4-oxadiazol-2-yl))ethoxy]chromen-4-one; | 0.017 μM | No inhibition up to 10 μM | 30% inhibition at 10 μM |
| PT-114. | 3-(4-hydroxyphenyl)-7-[(3-(3-pyridyl)(1,2,4-oxadiazol-5-yl))methoxy]chromen-4-one; | 0.032 μM | No inhibition up to 10 μM | No inhibition at 10 μM |
| PT-115. | 3-(4-hydroxyphenyl)-7-({3-[3-(trifluoromethyl)phenyl](1,2,4-oxadiazol-5-yl)}methoxy)chromen-4-one; | 0.038 μM | No inhibition up to 10 μM | No inhibition at 10 μM |
| PT-116. | 3-(4-hydroxyphenyl)-7-[(5-(3-pyridyl)(1,3,4-oxadiazol-2-yl))ethoxy]chromen-4-one; | 0.015 μM | No inhibition up to 10 μM | 33% inhibition at 10 μM |
| PT-117. | 3-(4-hydroxyphenyl)-7-[(5-(4-pyridyl)(1,2,4-oxadiazol-3-yl))ethoxy]chromen-4-one; | 0.098 μM | No inhibition up to 10 μM | No inhibition at 10 μM |
| PT-118. | (2-{[3-(4-hydroxyphenyl)-4-oxochromen-7-yloxy]methyl}(1,3-oxazol-4-yl))-N-methylcarboxamide; | 0.023 μM | No inhibition up to 10 μM | No inhibition at 10 μM |
| PT-119. | 4-{[3-(4-hydroxyphenyl)-4-oxochromen-7-yloxy]methyl}-7-methoxychromen-2-one; | 0.068 μM | No inhibition up to 10 μM | No inhibition at 10 μM |

TABLE 1-continued

ALDH-2 AND MAO INHIBITION

| | COMPOUND | IC$_{50}$ hALDH2 | IC$_{50}$ hMAO-A | IC$_{50}$ hMAO-B |
|---|---|---|---|---|
| PT-120. | 7-{[5-(4-fluorophenyl)(1,3,4-oxadiazol-2-yl)]methoxy}-3-{4-[(methylsulfonyl)amino]-phenyl}chromen-4-one; | 0.276 µM | | |
| PT-121. | 7-{[5-(3-aminophenyl)(1,3,4-oxadiazol-2-yl)]methoxy}-3-(4-hydroxyphenyl)chromen-4-one; | 0.011 µM | No inhibition up to 10 µM | No inhibition at 10 µM |
| PT-122. | ethyl 1-{2-[3-(4-hydroxyphenyl)-4-oxochromen-7-yloxy]ethyl}pyrazole-4-carboxylate; | 0.012 µM | No inhibition up to 10 µM | No inhibition at 10 µM |
| PT-123. | 7-{2-[4-(3-chlorophenyl)piperazinyl]ethoxy}-3-(4-hydroxyphenyl)chromen-4-one; | 0.011 µM | No inhibition up to 10 µM | |
| PT-124. | 3-(4-hydroxyphenyl)-7-(2-{4-[3-(trifluoromethyl)phenyl]piperazinyl}ethoxy)chromen-4-one; | 0.018 µM | No inhibition up to 10 µM | 21% inhibition at 10 µM |

EXAMPLE 32

Reduction of Alcohol Dependency

Animals

The strains of alcohol-preferring rats are housed individually in stainless-steel wire mesh cages (26' 34' 20 cm) under constant temperature of 21±1° C. and reversed 12 hour light-12 hour dark cycle (10:00-22:00 dark). These rats consume significantly more alcohol than their respective control strains: the selectively-bred alcohol non-preferring (NP), the low alcohol-drinking (LAD) rat, and the Wistar rat. The FH and P rats were derived from the Wistar rat. Water and food (Agway Prolab Rat/Mouse/Hamster 3000 formula, Agway, Syracuse, USA) were provided ad lib.

Establishment of Baseline

Following the standard method (Murphy et al., 1988; Rezvani and Grady, 1994; Rezvani et al., 1995), alcohol-preferring rats are given 1 day access to water in a Richter tube followed by 3 days of free access to a solution of 10% (v/v) ethanol given as the only source of fluid. Thereafter, the rats were given a choice between alcohol and water for the remainder of the study. All experiments involve 24 hour free access to food, water, and alcohol in a two-bottle choice paradigm.

Experimental Protocol

After establishment of a stable baseline for alcohol and water intakes, animals are maintained on a continuous access to alcohol and water via a two-bottle choice paradigm for about 2 months. Then, rats receive a single i.p. injection of the saline vehicle, or a test compound at 09:30 am. Alcohol and water intakes are measured at 6 and 24 hours after the injection. Food intake is measured 24 hours after the injection.

Chronic Systemic Administration

A chronic experiment is conducted with adult male P rats. After establishment of stable baselines for alcohol and water intakes, and following a cross-over design, the test drug or vehicle is given i.p. once a day for 10 consecutive days. Alcohol and water intakes are measured at 6 and 24 hours after the treatment, whereas food intake is measured 24 hours after the treatment. Each rat receives both treatments, and a washout period of 3 days is imposed between treatments.

Statistical Analysis

The results are expressed as means±standard error of means (SEM). Alcohol intake (g/kg) is calculated by multiplying the volume of alcohol consumed by 10% and 0.7893 (ethanol density)/animal body weight in kg. Alcohol preference, expressed as a percentage, is calculated as follows: (volume of alcohol consumed in ml/total fluid intake in ml)×100 (Rezvani et al., 1990; Rezvani and Grady, 1994). Statistical differences between different groups are determined using analysis of variance followed by Newman-Keuls protected t-test.

EXAMPLE 33

Reduction of Cocaine Dependency and Relapse

Intravenous cocaine (0.35 mg/kg/inj) was used in an operant self administration and reinstatement model in rats. In this model, rats addicted to cocaine repeatedly pressed a lever to obtain an intravenous dose (iv) of cocaine. When cocaine was removed, rats stopped pressing the lever. However, rats resumed lever pressing for cocaine (reinstatement) if subjected to a small intraperitoneal (ip) dose (10 mg/kg) of cocaine that normally has no effect in naïve animals. This is a valid animal model of relapse in cocaine addicted humans, and tests the ability of compounds of Formula I to block cocaine craving and relapse.

Male Sprague-Dawley rats with jugular vein catheterization were used. Rats were presented with a choice of two levers in the test/training chamber. Depression of the active lever resulted in delivery of a cocaine reinforcer, while depression of the inactive lever did not result in reinforcement. During the initial 15 hour fixed ratio (FR) 1 training session (FR1 stands for one lever press equals one reinforcement delivery), a food pellet was taped to the active lever to facilitate lever pressing, and each active lever press resulted in the delivery of a single 45 mg food pellet (Noyes, Lancaster, N.H.). The following day the reinforcer was switched to FR1 lever pressing for cocaine (0.35 mg/kg/inj, delivered in 0.27 sec). Cocaine reinforcement was delivered on a modified FR1 schedule such that each drug infusion was accompanied by illumination of a stimulus over the active lever and a 20 second timeout during which active lever presses were counted but did not result in reinforcer delivery. After 20 seconds the stimulus light turned off and the first lever press again resulted in drug delivery. Depression of the inactive lever did not have any consequence. Daily training sessions for each group lasted 2 hours, or until a subject earned 200 drug infusions, whichever came first. The subjects remained in drug self-administration training mode until acquisition criterion was met (average presses on the active lever varied by <10% over 3 consecutive training days). This typically takes 10-14 days.

Extinction and Reinstatement

For extinction and reinstatement experiments, rats were required to display stable responding (variability not higher than 15% in 2 consecutive sessions) on the FR1 schedule of reinforcement. After achieving this criteria, extinction procedures began such that lever presses no longer resulted in delivery of the reinforcer. When average responding across three consecutive extinction sessions fell to 15% of responding during maintenance, subjects were tested for reinstatement. In cocaine-experienced animals, reinstatement was primed with a non-contingent injection of cocaine (10 mg/kg ip) immediately before the reinstatement session. In order to increase statistical power and therefore decrease animal usage, a second extinction period was initiated 3-4 days after the first, which allowed for additional within-subjects comparisons. Experiments used a between-session-training and testing method in which animals were trained to self administer drug. Their behavior was then extinguished and then reinstatement was primed on different days.

Results

Effect of 3-[(3-{4-[(methylsulfonyl)amino]phenyl}-4-oxochromen-7-yloxy)methyl]-benzoic acid (Compound A) on Cocaine Induced Relapse Ip injections of the ALDH-2 inhibitor 3-[(3-{4-[(methylsulfonyl)amino]phenyl}-4-oxochromen-7-yloxy)methyl]benzoic acid dose dependently blocked relapse for cocaine. Animals were trained to self administer cocaine (0.35 mg/kg/inj) until they reached stable responding. They were then trained in the same chambers but cocaine was no longer available. Once they dropped their lever presses responding to a minimal level (extinction), they were then given a priming dose of cocaine (10 mg/kg) and consequently their responding lever presses significantly increased (relapse). Those same animals receiving 3-[(3-{4-[(methylsulfonyl)amino]phenyl}-4-oxochromen-7-yloxy)methyl]benzoic acid (7.5 and 10 mg/kg) prior to the priming injection of cocaine did not show an increase in their lever presses responding (did not relapse).

TABLE 2

| | Lever presses (Avg ± Std. error) | | |
|---|---|---|---|
| Extinction - no drug available N = 15 | Vehicle prior to cocaine priming dose (10 mg/kg) n = 15 | Cmpd A (7.5 mg/kg) prior to cocaine priming dose (10 mg/kg) N = 9 | Cmpd-A (10 mg/kg) prior to cocaine priming (10 mg/kg) dose N = 6 |
| 6.11 ± 0.58 | 59.75 ± 14.86# | 24.94 ± 7.92* | 19.83 ± 11.30* |

Significantly different from Extinction, p < 0.01
*Significantly different from Vehicle, p < 0.05

The following compounds of Formula I were similarly tested, and similar results were obtained:

7-({5-[3-fluoro-5-(trifluoromethyl)phenyl](1,2,4-oxadiazol-3-yl)}methoxy)-3-(4-hydroxyphenyl)chromen-4-one; and 3-(3-{[3-(4-hydroxyphenyl)-4-oxochromen-7-yloxy]methyl}-1,2,4-oxadiazol-5-yl)benzoic acid.

Similar results are obtained in testing other compounds of Formula I.

EXAMPLE 34

Reduction of Nicotine Dependency

Biological Material:

Wistar-derived male rats (250-300 g) were housed in groups of two and maintained in a temperature-controlled environment on a 12 hour: 12 hour light cycle (0600 h on-1800 h off), upon arrival in the laboratory. Animals were given free access to food and water during a one-week habituation period to the laboratory. Animals used in the research studies were handled, housed, and sacrificed in accord with the current NIH guidelines regarding the use and care of laboratory animals, and all applicable local, state, and federal regulations and guidelines. Animals were handled daily for several days to desensitize them to handling stress before experimental testing. The sample sizes (n=8) provided reliable estimates of drug effects.

Drug Treatments:

The Wistar-derived rats received several doses of 3-[(3-{4-[(methylsulfonyl)amino]phenyl}-4-oxochromen-7-yloxy)methyl]benzoic acid (0.00, 7.5, 10, and 15 mg/kg) administered intraperitonealy (i.p.), and a positive control compound, mecamylamine (1.5 mg/kg, subcutaneously (s.c.). The compounds were administered 30 minutes prior to SA sessions. 3-[(3-{4-[(methylsulfonyl)amino]phenyl}-4-oxochromen-7-yloxy)methyl]benzoic acid was administered at 2 ml/kg for the 7.5 mg/kg (3.75 mg/ml) and 10 mg/kg (5 mg/ml), doses, and at 3 ml/kg for the 15 mg/kg dose (5 mg/ml). The compound was dissolved in corn oil (VEH), and sonicated for at least 30-minutes, up to 2 hours prior to administration. Mecamylamine was dissolved in 0.09% isotonic saline and administered at a volume of 1 ml/kg.

Apparatus:

Food training and nicotine self-administration took place in 8 standard Coulbourn operant chambers. Each chamber was housed in a sound-attenuated box. Operant chambers were equipped with two levers, mounted 2 cm above the floor, and a cue light mounted 2 cm above the right lever on the back wall of the chamber. For food training, a food hopper was located 2-cm to the left/right of either lever, in the middle of the back wall. Intravenous infusions were delivered in a volume of 0.1 ml over a 1 second interval via an infusion pump (Razel, Conn.) housed outside of the sound attenuated chamber.

Food Training:

Lever pressing was established as demonstrated by the method of Hyytia et al., (1996). Initially, rats were restricted to 15 grams of food daily (approximately 85% of their free-feeding body weight). After the second day of food restriction, rats were trained to respond for food under a fixed-ratio 1 (FR1) schedule of reinforcement (1 food pellet for each lever press) with a 1 second time-out (TO-1s) after each reinforcement. Training sessions were given twice per day, and TO periods were gradually increased to 20 seconds. Once rats obtained a steady baseline responding at a FR1-TO20s schedule of reinforcement, they were returned to ad libitum food prior to preparation for intravenous jugular catheter implant surgery.

Surgery:

Rats were anesthetized with a ketamine/xylazine mixture and chronic silastic jugular catheters were inserted into the external jugular vein and passed subcutaneously to a polyethylene assembly mounted on the animal's back. The catheter assembly consisted of a 13-cm length of silastic tubing (inside diameter 0.31 mm; outside diameter 0.64 mm), attached to a guide cannula that was bent at a right angle. The cannula was embedded into a dental cement base and anchored with a 2×2 cm square of durable mesh. The catheter was passed subcutaneously from the rats back to the jugular vein where it was inserted and secured with a non-absorbable silk suture. Upon successful completion of surgery, rats were given 3-5 days to recover before self-administration sessions started. During the recovery period, rats remained ad libitum food access, and had catheter lines flushed daily with 30 units/ml of heparinized saline containing 66 mg/ml of Timentin to prevent blood coagulation and infection in the catheters.

Nicotine Self-Administration:

Following successful recovery from catheter implant surgery, rats were again food deprived to 85% of their free-feeding body weight. Once self-administration sessions began, subjects were trained to IV self-administer nicotine in 1-hour baseline sessions, 5 days per week, under a FR1-TO-20 schedule of reinforcement until stable responding was achieved. Stable responding is defined as less than 20% variability across 3 consecutive sessions. After acquisition of stable responding for nicotine, various doses of 3-[(3-{4-[(methylsulfonyl)amino]phenyl}-4-oxochromen-7-yloxy)methyl]benzoic acid were tested using a within-subjects Latin square design. Rats were allowed to self-administer nicotine after treatment with each dose of 3-[(3-{4-[(methylsulfonyl)amino]phenyl}-4-oxochromen-7-yloxy)methyl]benzoic acid for 1 test session, and subsequently "rebaselined" for 1-3 days before the next dose probe during one test self-administrations sessions. Following the testing of the first compound, rats received the positive control compound, mecamylamine (1.5 mg/kg), administered according to a crossover design.

During SA sessions, rats were flushed with saline before test session to ensure catheter patency, and again flushed after test sessions with 30 units/ml of heparinized saline containing 66 mg/ml of Timentin, to prevent blood coagulation and infection in the catheters. If catheter patency was in question, demonstrated by an unexpected shift in response rates, or inability to draw blood from the catheter, 0.1 ml of a short-acting anesthetic (Brevital) was infused. Animals with patent catheters exhibited rapid loss of muscle tone within 3-seconds. Rats with catheters no longer patent according to the Brevital test were removed from the experiment.

Data Analysis

Data was collected on-line from multiple operant chambers, and reported as mean cumulative number of bar presses for nicotine. The data was analyzed using the StatView statistical package on a PC-compatible computer.

Results

Effect of 3-[(3-{4-[(methylsulfonyl)amino]phenyl}-4-oxochromen-7-yloxy)methyl]-benzoic acid on Nicotine Self Administration Increasing doses of 3-[(3-{4-[(methylsulfonyl)amino]phenyl}-4-oxochromen-7-yloxy)methyl]benzoic administered as described in the above protocol reduced the number of bar presses (plotted as the number of infusions) for nicotine administration, as shown in the FIGURE.

Similar results are obtained in testing other compounds of Formula I.

What is claimed is:
1. A compound of the formula:

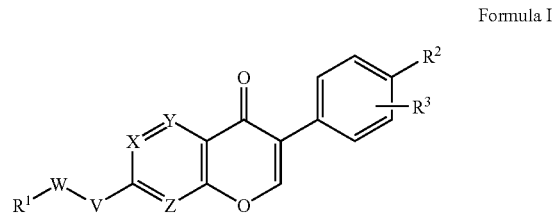

Formula I wherein:
R$^1$ is phenyl optionally substituted with CO$_2$CH$_2$CH$_3$, CN, CONH$_2$, CO$_2$H, haloalkyl, —O-haloalkyl, CO$_2$CH$_2$CH$_2$-heterocyclyl, where heterocyclyl is morpholinyl, piperazinyl, and CO$_2$-alkyl where alkyl is optionally substituted with N(CH3)2 or Si(CH3)3;
R$^2$ is —NHSO$_2$—CH$_3$, OH, NO$_2$, NH$_2$, CH$_2$OH, NHCONHCH$_3$, OCH$_2$CONH$_2$, OCOCH$_3$, B(OH)$_2$, CONH$_2$, CN, CH$_3$, CNHNHOH, SO$_2$NH$_2$, CNOCH$_3$NH$_2$, or NHCOCH$_3$ R$^3$ is hydrogen;
X Y and Z are chosen from —CR$^7$—, in which R$^7$ is hydrogen, lower alkyl, lower alkoxy, or halo;
V is oxygen, sulfur, or —NH—; and
W is -Q$^1$-T-Q$^2$-, wherein
Q$^1$ is a covalent bond or C$_{1-6}$ linear or branched alkylene optionally substituted with hydroxy, lower alkoxy, amino, cyano, or =O;
Q$^2$ is C$_{1-6}$ linear or branched alkylene optionally substituted with hydroxy, lower alkoxy, amino, cyano, or =O; and
T is a covalent bond, —O—, or —NH—, or
T and Q$^1$ may together form a covalent bond; or a pharmaceutically acceptable salt thereof.

2. The compound of claim 1 wherein,
R$^2$ is —NHSO$_2$—CH$_3$, OH, NO$_2$, NH$_2$, CH$_2$OH, NHCONHCH$_3$, OCH$_2$CONH$_2$, OCOCH$_3$, B(OH)$_2$, CONH$_2$, CN, CH$_3$, CNHNHOH, SO$_2$NH$_2$, CNOCH$_3$NH$_2$, or NHCOCH$_3$.

3. The compound of claim 2, wherein V is —O—.

4. The compound of claim 3, wherein Q$^1$ and Q$^2$ are branched alkylene.

5. The compound of claim 3, wherein Q$^1$ and Q$^2$ together form a covalent bond and Q$^2$ is methylene so that W is methylene.

6. The compound of claim 5, wherein R$^2$ is hydroxy or —NHSO$_2$CH$_3$.

7. The compound of claim 5, where-in R$^1$ is phenyl optionally substituted with one to three members selected from lower alkyl, B(OH)$_2$, C(O)NH$_2$, CO$_2$CH$_2$CH$_3$, CN, halogen, heteroaryl, OCF$_3$, and phenyl optionally substituted with 1 to 3 members selected from CF$_3$, halogen, OH, —OCH$_3$, CN, heteroaryl, C(O)OH, or lower alkyl.

8. A compound selected from the group consisting of
methyl 3-((3-(4-hydroxyphenyl)-4-oxo-4H-chromen-7-yloxy)methyl)benzoic acid;
methyl-3-((3-(4-hydroxyphenyl)-4-oxo-4H-chromen-7-yloxy)methyl)benzoate;
methyl 3-((3-(4-(methylsulfonamido)phenyl)-4-oxo-4H-chromen-7-yloxy)methyl)benzoate;
allyl 3-((3-(4-methylsulfonamido)phenyl)-4-oxo-4H-chromen-7-yloxy)methyl)benzoate;
3-((3-(4-(methylsulfonamido)phenyl)-4-oxo-4H-chromen-7-yloxy)methyl)benzoic acid;

methyl 3-((3-(4-(2-amino-2-oxoethoxy)phenyl)-4-oxo-4H-chromen-7-yloxy)methyl)benzoate;
methyl 3-((3-(4-acetoxyphenyl)-4-oxo-4H-chromen-7-yloxy)methyl)benzoate;
3-{[3-(4-aminophenyl)-4-oxochromen-7-yloxy]methyl}benzenecarbonitrile;
3-[3-{4-[(methylsulfonyl)amino]phenyl}-4-oxochromen-7-yloxy)methyl]benzamide;
3-[(3-{4-[(methylsulfonyl)amino]phenyl}-4-oxo-chromen-7-yloxy)methyl]benzenecarbonitrile;
methylethyl 3-[(3-{4-[(methylsulfonyl)amino]phenyl}-4-oxochromen-7-yloxy)methyl]benzoate;
3-{4-[(methasulfonyl)amino]phenyl}-7-{[3-(trifluoromethyl)phenyl]methoxy}chromen-4-one;
3-{[3-(4-aminophenyl)-4-oxochromen-7-yloxy]methyl}benzamide;
3-(4-aminophenyl)-7-{[3-(trifluoromethyl)phenyl]methoxy}chromen-4-one;
3-(4-aminophenyl)-7-{[3-(trifluoromethoxy)phenyl]methoxy}chromen-4-one;
3-{4-[(methylsulfonyl)amino]phenyl}-7-{[3-(trifluoromethoxy)phenyl]methoxy}chromen-4-one;
methylethyl 3-{[3-(4-aminophenyl)-4-oxochromen-7-yloxy]methyl}benzoate;
methyl 3({3-[4-(hydroxymethyl)phenyl]-4-oxochromen-7-yloxy}methyl)benzoate;
methyl 3-({3-[4-(dihydroxyboramethyl)phenyl]-4-oxochromen-7-yloxy}methyl)benzoate;
3,3-dimethyl-3-silabutyl 3-{[3(4-carbamoylphenyl)-4-oxochromen-7-yloxy]methyl}benzoate;
3,3-dimethyl-3-silabutyl 3-[(3-{3-[(methylsulfonyl)amino]phenyl}-4-oxochromen-7-yloxy)methyl]benzoate;
3,3-dimethyl-3-silabutyl 3-{[3-(3-cyanphenyl)-4-oxochromen-7-yloxy]methyl}benzoate;
methyl 3-{[3-(4-{[4-methylphenyl)sulfonyl]amino}phenyl)-4-oxochromen-7-yloxy]methyl}benzoate;
methyl 3-({3-[4-(amino(hydroxyimino)methyl)phenyl]-4-oxochromen-7-yloxy}methyl)benzoate;
3-{[3-(4-carbamoylphenyl)-4-oxochromen-7-yloxy]methyl}benzoic acid, methanol, methanol;
3-({3-[4-(methylsulfonyl)phenyl]-4-oxochromen-7-yloxy}methyl)benzoic acid;
4-((3-(4-hydroxyphenyl)-4-oxo-4H-chromen-7-yloxy)methyl)phenylboronic acid;
3-((3-(4-hydroxyphenyl)-4-oxo-4H-chromen-7-yloxy)methyl)phenylboronic acid;
N-{[4-chloro-3-(trifluoromethyl)phenyl]methyl}(3-{[3-(4-hydroxyphenyl)-4-oxochromen-7-yloxy]methyl}phenyl)carboxamide;
(3-{[3-(4-hydroxyphenyl)-4-oxochromen-7-yloxy]methyl}phenyl)-N-{[3-(trifluoromethyl)phenyl]methyl}carboxamide; and
methylethyl 3-{[3-(4-carbamoylphenyl)-4-oxochromen-7-yloxy]methyl}benzoate.

9. A compound selected from the group consisting of:
7-[2-(4-fluorophenyl)-2-oxoethoxy]-3-(4-methoxyphenyl)chromen-4-one;
7-[2-(4-fluorophenyl)-2-oxoethoxy]-3-(4-hydroxyphenyl)chromen-4-one;
3-(4-hydroxyphenyl)-7-{[3-(trifluoromethyl)phenyl]ethoxy}chromen-4-one;
7-[2-(3-fluorophenyl)-2-oxoethoxy]-3-(4-hydroxyphenyl)chromen-4-one;
3-(4-hydroxyphenyl)-7-{2-oxo-2-[4-(trifluoromethyl)phenyl]ethoxy}chromen-4-one;
3-(4-hydroxyphenyl)-7-{2-oxo-2-[2-(trifluoromethyl)phenyl]ethoxy}chromen-4-one; and
7-((2-S)-2-hydroxy-3-phenylpropoxy)-3-(4-hydroxyphenyl)chromen-4-one.

10. A compound selected from the group consisting of:
2-[3-(4-hydroxyphenyl)-4-oxochromen-7-yloxy]-n-[3-(trifluoromethyl)phenyl]acetamide;
7-(3-{[(3,5-difluorophenyl)methyl]amino}-2-hydroxypropoxy)-3-(4-methoxyphenyl)chromen-4-one;
7-[(2S)-2-hydroxy-3-({[3-(trifluoromethyl)phenyl]methyl}amino)propoxy]-3-(4-methoxyphenyl)chromen-4-one;
2-[3-(4-hydroxyphenyl)-4-oxochromen-7-yloxy]-N[2-(trifluoromethyl)phenyl]acetamide;
N-[(1S)-1-(4-fluorophenyl)ethyl]-2-[3-(4-hydroxyphenyl)-4-oxochromen-7-yloxy]acetamide;
N-(3-fluorophenyl)-2-[3-(4-hydroxyphenyl)-4-oxochromen-7-yloxy]acetamide;
7-[(2S)-2-hydroxy-3-({[3-(trifluoromethyl)phenyl]methyl}amino)propoxy]-3-(4-hydroxyphenyl)chromen-4-one;
3-(4-hydroxyphenyl)-7-[2-({[3-(trifluoromethyl)phenyl]methyl}amino)ethoxy]chromen-4-one;
7-((2S)-3-{[(3,5-difluorophenyl)methyl]amino}-2-hydroxypropoxy)-3-(4-hydroxyphenyl)chromen-4-one;
N-[(1R)-1-(4-fluorophenyl)ethyl]-2-[3-(4-hydroxyphenyl)-4-oxochromen-7-yloxy]acetamide;
7-(2-{[(4-fluorophenyl)ethyl]amino}ethoxy)-3-(4-hydroxyphenyl)chromen-4-one; and
7-[2-(4-chlorophenoxy)ethoxy]-3-(4-hydroxyphenyl)chromen-4-one.

11. A pharmaceutical composition comprising a therapeutically effective amount of the compound of claim 1 and a pharmaceutically acceptable carrier.

* * * * *